United States Patent
Labrie et al.

(10) Patent No.: US 9,284,345 B2
(45) Date of Patent: Mar. 15, 2016

(54) 17ALPHA-SUBSTITUTED STEROIDS AS SYSTEMIC ANTIANDROGENS AND SELECTIVE ANDROGEN RECEPTOR MODULATORS

(75) Inventors: Fernand Labrie, de la Promenade (CA); Sylvain Gauthier, St-Augustin-de-Desmaures (CA); Julie Cloutier, Lévis (CA); Josée Mailhot, Québec (CA); Steeves Potvin, Québec (CA); Sylvain Dion, St-Romuald (CA); Jean-Yves Sancéau, Québec (CA)

(73) Assignee: ENDORECHERCHE, INC. (CA)

( * ) Notice: Subject to any disclaimer, the term of this patent is extended or adjusted under 35 U.S.C. 154(b) by 1015 days.

(21) Appl. No.: 12/100,372

(22) Filed: Apr. 9, 2008

(65) Prior Publication Data

US 2009/0042844 A1 Feb. 12, 2009

Related U.S. Application Data

(60) Provisional application No. 60/911,434, filed on Apr. 12, 2007, provisional application No. 60/911,452, filed on Apr. 12, 2007.

(51) Int. Cl.
*A61K 31/58* (2006.01)
*C07J 3/00* (2006.01)
(Continued)

(52) U.S. Cl.
CPC ............ *C07J 41/0094* (2013.01); *C07J 43/003* (2013.01); *C07J 63/008* (2013.01)

(58) Field of Classification Search
USPC ............ 514/171, 176, 182; 540/112; 552/611
See application file for complete search history.

(56) References Cited

U.S. PATENT DOCUMENTS 2,938,030 A 5/1960 Hoffmann et al.
3,117,140 A 1/1964 Hecker
(Continued)

FOREIGN PATENT DOCUMENTS

CA 2001938 4/1990
CA 2062973 1/1991
(Continued)

OTHER PUBLICATIONS

Rosenkranz, G et al. (Journal of Organic Chemistry (1956), 21, 520-2).*
(Continued)

*Primary Examiner* — Sabiha N Qazi
(74) *Attorney, Agent, or Firm* — Ostrolenk Faber LLP

(57) ABSTRACT

Compounds having the structure, their salts or N-oxide derivatives:

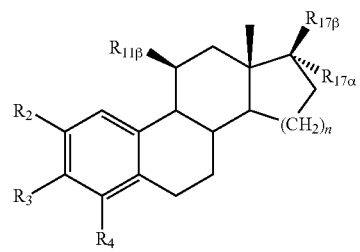

are used to treat or reduce le likelihood of acquiring androgen-dependent diseases, such as prostate cancer, benign prostatic hyperplasia, polycystic ovarian syndrome, acne, hirsutism, seborrhea, androgenic alopecia and male baldness. They can be formulated together with pharmaceutically acceptable diluent or carrier or otherwise made into any pharmaceutical dosage form. Combinations with other active pharmaceutical agents are also disclosed.

18 Claims, 18 Drawing Sheets

(51) Int. Cl.
  *C07J 41/00* (2006.01)
  *C07J 43/00* (2006.01)
  *C07J 63/00* (2006.01)

(56) References Cited

U.S. PATENT DOCUMENTS

| | | | |
|---|---|---|---|
| 3,742,951 A | 7/1973 | Zaffaroni | 128/268 |
| 3,797,494 A | 3/1974 | Zaffaroni | 128/268 |
| 4,568,343 A | 2/1986 | Leeper et al. | 604/896 |
| 5,064,654 A | 11/1991 | Berner et al. | 424/448 |
| 5,071,644 A | 12/1991 | Viegas et al. | 514/772.7 |
| 5,071,657 A | 12/1991 | Oloff et al. | 424/486 |
| 5,362,720 A * | 11/1994 | Labrie | 514/169 |
| 5,411,981 A | 5/1995 | Gaillard-Kelly et al. | 514/386 |
| 5,434,176 A | 7/1995 | Claussner et al. | 514/391 |
| 5,914,325 A | 6/1999 | Droescher et al. | |
| 6,071,957 A | 6/2000 | Miller et al. | 514/522 |
| 7,119,081 B2 * | 10/2006 | Potter et al. | 514/171 |
| 2003/0203855 A1 | 10/2003 | Potter et al. | |
| 2004/0077605 A1 | 4/2004 | Salvati et al. | 514/81 |
| 2004/0077606 A1 | 4/2004 | Salvati et al. | 514/81 |
| 2004/0082556 A1 * | 4/2004 | Labrie et al. | 514/174 |
| 2005/0033074 A1 | 2/2005 | Dalton et al. | 556/87 |
| 2005/0250741 A1 | 11/2005 | Lanter et al. | 514/63 |
| 2005/0250749 A1 | 11/2005 | Labrie et al. | 514/177 |
| 2006/0009529 A1 | 1/2006 | Dalton et al. | 514/620 |
| 2006/0014739 A1 | 1/2006 | Schlienger et al. | 514/231.2 |
| 2006/0287327 A1 | 12/2006 | Labrie et al. | 514/249 |
| 2012/0322778 A1 * | 12/2012 | Labrie | 514/171 |

FOREIGN PATENT DOCUMENTS

| | | |
|---|---|---|
| CA | 2323089 | 9/1999 |
| CA | 2339368 | 2/2002 |
| EP | 0002892 | 7/1979 |
| EP | 0100172 | 2/1984 |
| EP | 0279982 | 8/1988 |
| EP | 0494819 | 7/1992 |
| EP | 0578516 | 1/1994 |
| EP | 0580459 | 1/1994 |
| FR | 1473910 | 3/1967 |
| FR | 2671348 | 7/1992 |
| FR | 2693461 | 1/1994 |
| JP | 2002-88073 | 3/2002 |
| WO | WO 95/18794 | 7/1995 |
| WO | WO 97/00071 | 1/1997 |
| WO | WO 97/19064 | 5/1997 |
| WO | WO 97/23464 | 7/1997 |
| WO | WO 98/53826 | 12/1998 |
| WO | WO 99/46279 | 9/1999 |
| WO | WO 00/37430 | 6/2000 |
| WO | WO 01/16108 | 3/2001 |
| WO | WO 01/16133 | 3/2001 |
| WO | WO 01/98322 A1 | 12/2001 |
| WO | WO 02/00617 | 1/2002 |
| WO | WO 02/24702 | 3/2002 |
| WO | WO 02/068548 A1 | 9/2002 |
| WO | WO 2004/085457 A2 | 10/2004 |
| WO | WO 2004/089971 | 10/2004 |
| WO | WO 2004/089971 A1 | 10/2004 |
| WO | WO 2004/099188 | 11/2004 |
| WO | WO 2004/111012 | 12/2004 |
| WO | WO 2004/113309 | 12/2004 |
| WO | WO 2005/040136 | 5/2005 |
| WO | WO 2005/048956 A2 | 6/2005 |
| WO | WO 2005/066194 | 7/2005 |
| WO | WO 2005/120483 | 12/2005 |
| WO | WO 2006/133567 | 12/2006 |

OTHER PUBLICATIONS

Bolvin et al. (J. of Medicinal Chemistry, 2000, 43, (23), 4465-4478).*
Dorwald, F. A., Side Reactions in Organic Synthesis, 2005, Wiley: VCH, Weinheim p. IX of Preface.*
Roy, D. R. et al. (Euorpean J of Medicinal Chemistry (2007), 42(11-12), 1365-1369).*
Roy, D. R. et al. (AN 2007:1368057, DN 148:11368057, HCAPLUS, abstract of Euorpean J of Medicinal Chemistry (2007), 42(11-12), 1365-1369).*
Ciobanu et al. (J. Med. Chem. 1999, 42, 2280-2286).*
Poirier et. al. (Bioorganic & Medicinal Chemistry Letters (1998), 1891-1896.*
Boivin, Roch et al. (AN 2000:736379, HCAPLUS, DN 133:359332, abstract of Journal of Medicinal Chemistry (2000), 43(23), 4465-4478).*
International Search Report and Written Opinion dated Jul. 25, 2008 issued in corresponding PCT International Application No. PCT/CA2008/000672.
Ponsold, et al., "Anodic oxidation of ring A-aromatic steroids. Cyanation of the aromatic nucleus", Tetrahedron Letters, 1979, No. 46, pp. 4465-4466.
Holt, et al., "Steroidal A Ring Aryl Carboxylic Acids: A New Class of Steroid 5aReductase Inhibitors", J. Med. Chem., 1990, 33, pp. 937-942.
Shi, et al., "Functionally Orthogonal Ligand-Receptor Pairs for the Selective Regulation of Gene Expression Generated by Manipulation of Charged Residues at the Ligand-Receptor Interface of ERα and ERβ", J Am. Chem. Soc., 2002, 124, pp. 6921-6928.
Hecker, et al., "Neue Östranabkömmlinge mit verschiedenen Substituenten in 3 Stellung", Chemische Berichte, 1962, 95(4), pp. 977-984.
Dorfman, et al., "Uterotrophic Activity of Various Phenolic Steroids", Acta Endocrin., 1966, 52(4), pp. 619-626.
Ponsold, et al., "Electrochemical transformation of steroids", Chemical Abstracts, CAPLUS 91:201156h (1979).
Liu, et al., "Synthesis of 4-Formyl Estrone Using a Positional Protecting Group and Its Conversion to Other C-4-Substituted Estrogens", J. Org. Chem., 2007, 72(23), pp. 8824-8830.
Oppolzer, et al., "The Enantioselective Synthesis of (+)-Estradiol from 1,3-Dihydrobenzo[c]thiophene-2, 2-dioxide by Successive Thermal $SO_2$-Extrusion and Cycloaddition Reactions", Helvetica Chimica Acta, vol. 63, Fasc. 6 (1980), No. 177.
International Preliminary Report on Patentability dated Oct. 22, 2009, issued in corresponding International Application No. PCT/CA2008/000672.
Patent family search for JP 2002088073 (Dialog eLink 2/5/1 Dialog(R) File 351:Derwent WPI, New anti-androgen agent, containing cyanophenyl, derivative for prevention or treatment of prostatic cancer or prostatic hypertrophy, http://www.dialogclassic.com/mainframe.html, Nov. 25, 2009.
Labrie, F., Veilleux, R.: Maintenance of androgen responsiveness by glucocorticoids in Shionogi mammary carcinoma cells in culture. J. Natl. Cancer Inst., vol. 80, No. 12, pp. 966-970 (1988).
Labrie, F., Veilleux, R. Fournier, A.: Glucocorticoids stimulate the growth of mouse mammary carcinoma Shionogi cells in culture. Mol. Cell. Endocrinol., 58: 207-211 (Aug. 17, 1988).
Labrie, F. Veilleux, R., Fournier, A.: Low androgen levels induce the development of androgen-hypersensitive cells clones in Shionogi mouse mammary carcinoma cells in culture. J. Natl. Cancer Inst., vol. 80, No. 14, pp. 1138-1147 (1988).
Simard, J., Dauvois, S., Haagensen, D.E., Lévesque, C., Mérand, Y., Labrie, F.: Regulation of progesterone-binding breast cyst protein GCDFP-24 secretion by estrogens and androgens in human breast cancer cells: a new marker of steroid action in breast cancer, Endocrinology, vol. 126, No. 6, pp. 3223-3231 (1990).
Poortmans, A., Wyndaele, J.J.: M. levator ani in the rat: does it really lift the anus?, The Anatomical Record, 251: 20-27 (1998).
U.S. Appl. No. 11/030,850, filed Jan. 7, 2007 by Fernand Labrie et al., entitled Helix 12 Directed Pharmaceutical Products.
U.S. Appl. No. 11/452 545, filed Jun. 14, 2006 by Fernand Labrie et al., entitled Helix 12 Directed Non-Steroidal Antiandrogens.
SciFinder® Search dated Apr. 24, 2014, pp. 1-3, Copyright© 2014 American Chemical Society (ACS), search related to 17alpha-(4-picolyl)-1,3,5(10)-estratriene(2).
Singh, Shankar M., et al., "Androgen Receptor Antagonists (Antiandrogens): Structure-Activity Relationships," Current Medicinal Chemistry, 2000, pp. 211-247.

(56) References Cited

OTHER PUBLICATIONS

Negro-Vilar, Andres, "Selective Androgen Receptor Modulators (SARMs): A Novel Approach to Androgen Therapy for the New Millennium" The Journal of Clinical Endocrinology & Metabolism, 1999 The Endocrine Society, vol. 84, No. 10, pp. 3459-3462.
Liu, Peter Y. et al. "Androgens and Cardiovascular Disease", Endocrine Reviews 24(3), 2003, pp. 313-340.
Labrie, Fernand M.D., Ph.D., "Adrenal Androgens and Intracrinology", Seminars in Reproductive Medicine, vol. 22, No. 2, 2004, pp. 299-309.
Obiezu, Christina V., et al., "Prostate-Specific Androgen and Human Glandular Kallikrein 2 Are Markedly Elevated in Urine of Patients with Polycystic Ovary Syndrome", The Journal of Clinical Endocrinology, 2001, vol. 86, No. 4, pp. 1558-1561.
Scifinder® Search 1 dated Dec. 7, 2011, pp. 1-7, American Chemical Society (ACS), Copyright © 2011.
Scifinder® Search 2 dated Dec. 7, 2011, pp. 1-6, American Chemical Society (ACS), Copyright © 2011.
Scifinder® Search 3 dated Dec. 7, 2011, pp. 1-6, American Chemical Society (ACS), Copyright © 2011.
Scifinder® Search 4 dated Dec. 7, 2011, pp. 1-9, American Chemical Society (ACS), Copyright © 2011.
Scifinder® Search 5 dated Dec. 7, 2011, pp. 1-2, American Chemical Society (ACS), Copyright © 2011.
Scifinder® Search 6 dated Dec. 7, 2011, pp. 1-2, American Chemical Society (ACS), Copyright © 2011.
Scifinder® Search 7A dated Dec. 5, 2011, pp. 1-56, American Chemical Society (ACS), Copyright © 2011.
Scifinder® Search 7B dated Dec. 5, 2011, pp. 1-13, American Chemical Society (ACS), Copyright © 2011.
Scifinder® Search 8 dated Dec. 7, 2011, pp. 1-2, American Chemical Society (ACS), Copyright © 2011.
Scifinder® Search 9 dated Dec. 7, 2011, pp. 1-2, American Chemical Society (ACS), Copyright © 2011.
Scifinder® Search 10 dated Dec. 7, 2011, pp. 1-2, American Chemical Society (ACS), Copyright © 2011.
Scifinder® Search 11 dated Dec. 8, 2011, pp. 1-4, American Chemical Society (ACS), Copyright © 2011.
Scifinder® Search 12 dated Dec. 8, 2011, pp. 1-2, American Chemical Society (ACS), Copyright © 2011.
Scifinder® Search 13 dated Dec. 8, 2011, pp. 1-6, American Chemical Society (ACS), Copyright © 2011.
Scifinder® Search 14 dated Dec. 8, 2011, pp. 1-2, American Chemical Society (ACS), Copyright © 2011.
Scifinder® Search 15 dated Dec. 7, 2011, pp. 1-14, American Chemical Society (ACS), Copyright © 2011.
Scifinder® Search 16 dated Dec. 7, 2011, pp. 1-17, American Chemical Society (ACS), Copyright © 2011.
Scifinder® Search 17 dated Dec. 7, 2011, pp. 1-3, American Chemical Society (ACS), Copyright © 2011.
Scifinder® Search 18 dated Dec. 8, 2011, pp. 1-2, American Chemical Society (ACS), Copyright © 2011.
O. G. Mekenyan, et al. "A Computationally Based Identification Algorithm for Estrogen Receptor Ligands: Part 2. Evaluation of a hER$\alpha$ Binding Affinity Model," (2000) Toxicological Sciences, 58, pp. 270-281.
C. Liarakos, et al., "Estrogenic Activities of Some 3-Alkoxyestra-I,3,5(10)-trien-17$\beta$-ols," (1969) Endocrinology, 84(5), 1247 (2 pages) (Abstract).
Fernand Labrie, "GnRH Agonists and the Rapidly Increasing Use of Combined Androgen Blockade in Prostate Cancer," Endocrine-Related Cancer (2014) 21, pp. R301-R317.
Fernand Labrie, et al., "Can Combined Androgen Blockade Provide Long-Term Control or Possible Cure of Localized Prostate Cancer?" Urology (2002), 60(1), pp. 115-119.
R. Kauli, et al., "Treatment of Precocious Puberty With LHRH Analogue in Combination With Cyproterone Acetate-Further Experience," Clinical Endocrinology (1984), 20, pp. 377-387.
Extended European Search Report and European Search Opinion dated Oct. 5, 2012 in corresponding European Patent Application No. 08748116.4.
Wolfgang Römer et al., "Novel Estrogens and Their Radical Scavenging Effects, Iron-Chelating, and Total Antioxidative Activities: 17$\alpha$-substituted Analogs of $\Delta^{9(11)}$-dehydro-17-$\beta$- estradiol," Steroids, vol. 62(11), pp. 688-694 (Nov. 1, 1997).
Robert N. Hanson et al., "Synthesis and Evaluation of 17$\alpha$-20$E$-21-(4-Substituted phenyl)-19-norpregna-1,3,5(10),20-tetraene-3,17$\beta$-diols as Probes for the Estrogen Receptor $\alpha$ Hormone Binding Domain," J. Med. Chem., vol. 46(14), pp. 2865-2876 (Jul. 3, 2003).
Robert N. Hanson, et al., Synthesis and Evaluation of (17$\alpha$,20$Z$)-21-(4-Substituted-phenyl)-19-norpregna-1,3,5(10),20-tetraene-3, 17$\beta$-diols as Ligands for the Estrogen Receptor-$\alpha$ Hormone Binding Domain: Comparison with 20$E$-Isomers, J. Med. Chem., vol. 48(13), pp. 4300-4311 (Jun. 30, 2005).
Robert T. Blickenstaff, et al., "Conjugates of Steroids and Anti-Cancer Agents. III. The Synthesis of Estrynamine and Certain Derivatives," Steroids, vol. 48(3-4), pp. 223-231 (Sep.-Oct. 1986).
Kenneth Kam-Wing Lo, et al. "Luminescent Tricarbonylrhenium(I) Polypyridine Estradiol Conjugates: Synthesis, Crystal Structure, and Photophysical, Electrochemical, and Protein-Binding Properties," Organometallics, vol. 25(13), pp. 3220-3227 (2006).
Jeffrey B. Arterburn, et al., "Synthesis of 17-$\alpha$-Substituted Estradiol-Pyridin-2-yl Hydrazine Conjugates as Effective Ligands for Labeling with Alberto's Complex$fac$-[Re(OH$_2$)$_3$(CO)$_3$]+ in Water," J. Org. Chem., vol. 68(18), pp. 7063-7070 (Sep. 5, 2003).
Gillian M. Allan, et al., "Modification of Estrone at the 6, 16, and 17 Positions: Novel Potent Inhibitors of 17$\beta$-Hydroxysteroid Dehydrogenase Type 1," J. Med. Chem., vol. 49(4), pp. 1325-1345 (Feb. 23, 2006).
von J. Heer, et al., "215. On Pyridyl Steroids. II [1]. On Steroids, 142nd paper [2]," Helvetica Chimica Acta, vol. 39(6), pp. 1814-1820 (1956). (German reference with English language translation).

* cited by examiner

C= Control; EM= EM-5985

_US 9,284,345 B2_

17ALPHA-SUBSTITUTED STEROIDS AS SYSTEMIC ANTIANDROGENS AND SELECTIVE ANDROGEN RECEPTOR MODULATORS

CROSS-REFERENCE TO RELATED APPLICATION(S)

The present application claims priority of U.S. Provisional Application Ser. No. 60/911,434 filed Apr. 12, 2007 entitled THERAPEUTIC SELECTIVE ANDROGEN RECEPTOR MODULATORS and U.S. Provisional Application Ser. No. 60/911,452 filed Apr. 12, 2007 entitled EM-5854, EM-4350 AND RELATED COMPOUNDS AS SYSTEMIC ANTIANDROGENS, the disclosures of which are incorporated herein by reference.

BACKGROUND OF THE INVENTION

This invention relates to novel inhibitors of sex steroid activity, for example to steroidal compounds having antagonistic activity on sex steroid receptors. More particularly, the invention relates to certain steroidal compounds having specified side-chains in 17α-position which interact with the androgen receptor, and metabolites thereof which block androgen action by acting, among other mechanisms, through the androgen receptors, while not activating such receptors in some or all androgen-sensitive tissues. Some compounds of the invention are Selective Androgen Receptor Modulators (SARMs) which have desirable antagonist activity in some tissues (e.g. prostate) while exhibiting no activity or desirable agonist activity in other tissues

BRIEF DESCRIPTION OF THE PRIOR ART

During the treatment of certain androgen-dependent diseases, it is important to greatly reduce or, if possible, to eliminate androgen-induced effects. For this purpose, it is desirable to both block access to the androgen receptors with "antiandrogens", thus preventing androgens from binding and activating those receptors, and also to reduce the concentration of androgens available to activate the receptors. It is possible that, even in the absence of androgens, unoccupied androgen receptors may be biologically active. Hence, antiandrogens which bind and block the receptors may produce better therapeutic results than therapy which only inhibits androgen production.

Antiandrogens may have a significant therapeutic effect in slowing or stopping the progress of androgen-dependent diseases, e.g. diseases whose onset or progress is aided by androgen receptor or androgen receptor modulator activation.

It is desired that an antiandrogen used in therapy to reduce androgen receptor activation have both good affinity for the androgen receptor and a substantial lack of inherent androgenic activity in the tissue(s) of interest. The former refers to the ability of an antiandrogen to bind to the androgen receptor, and thus to block access to the receptor by androgens. The latter refers to the effect the antiandrogen has on the receptor once it binds thereto. Some antiandrogens may possess inherent androgenic activity ("agonistic activity") which undesirably activates the very androgen receptors whose activation they are intended to prevent the action. In other words, an antiandrogen with undesirable intrinsic androgenic activity may successfully bind to androgen receptors, desirably blocking access to those receptors by natural androgens, yet may undesirably itself activate the receptor in tissues where an exclusive antiandrogenic action is desired.

Known non-steroidal antiandrogens such as flutamide, casodex and anandron lack undesirable androgenic activity, but may have low receptor affinity compared to steroidal antiandrogens (i.e. androgen derivatives having a steroidal nucleus that is modified to provide antiandrogenic activity). Steroidal antiandrogens, however, are believed to more frequently possess undesirable agonistic characteristics, than non-steroidal antiandrogens. Recently, some new non-steroidal antiandrogens possessing long substituents and having a better activity than the above-mentioned non-steroidal antiandrogens were described (Kawaminami et al., 2005, Kinoyama et al., 2004, Tucker et al., 2004) disclosed (U.S. Pat. No. 5,411,981, U.S. Pat. No. 6,071,957, US 2004/0077605, US 2004/0077606, EP 0 100 172, FR 2671348 A1, FR 2693461 A1, EP 002 892, EP 0 494 819, EP 0 578 516, EP 0 580 459, WO 95/18794, WO 96/19458, WO 97/00071, WO 97/19064, WO 97/23464, WO 98/53826, JP2002088073A), WO 00/37430 WO 01/16108, WO 01/16133, WO 02/24702, WO 2004/099188, WO 2004/111012, WO 2004/113309, WO 2005/040136.

However, steroidal antiandrogens with very high affinity for the androgen receptor and lacking undesirable agonistic characteristic were disclosed in the U.S. patent application Ser. No. 11/030,850 and published in US-2005-0250749-A1, based upon the provisional application No. 60/535,121. These compounds possess specified side-chains positioned at position 18 and which interact with helix 12. Similarly non-steroidal antiandrogens with very high affinity for the androgen receptor and lacking undesirable agonistic characteristic were disclosed in the U.S. patent application Ser. No. 11/452,545 and published in US-2006-0287327-A1, based upon the provisional application No. 60/691,391.

There is thus a need in the Art for steroidal antiandrogens having high affinity for the androgen receptor, while substantially lacking undesirable agonistic characteristics and having a good parenteral or oral bioavailability for systemic uses.

We have synthezised a new series of steroidal anti-androgens possessing a side-chain able to modify the interaction of the steroidal backbone with the Androgen Receptor.

Selective Androgen Receptor Modulators (SARMs) is a new family of compounds having desirable antagonist activity in some tissues (e.g. prostate) while exhibiting no activity or desirable agonist activity in other tissues (e.g. bone or muscle). Some were recently reported in WO 02/00617, WO 2005/120483, US 2005/0033074, US 2005/0250741, US 2006/0014739, US 2006/0009529. Some of these SARMs are in clinical trials for building muscle and promoting bone (Ostarine developed by GTx in United States), hypogonadism, benign prostatic hyperplasia, osteoporosis and female sexual dysfunction (LGD 2226 2941 developed by Ligand in United States) or age-related decline (BMS 564929 developed by Bristol-Myers Squibb in United States).

SARMs are also potential drugs for the prevention and treatment of osteopenia, bone fractures, alveolar bone loss, bone reconstruction, osteotomy, wasting diseases (cancer), loss of lean mass, obesity, muscle damage, hot flashes, periodontal disease, periodontitis, mandibular bone loss, Sjogren syndrome, eye dryness, dry skin, breast cancer, and possibility prostate cancer when the selective androgen receptor modulators (SARM) is free of androgenic activity in the prostate.

During the course of our antiandrogen research development program, we have synthesized a series of steroidal compounds possessing the biological properties of selective androgen receptor modulators. Particularly, we have focused our research on compounds having biological characteristics suitable for the treatment of benign prostatic hyperplasia and the prevention of the prostate cancer. For that purpose, SARMs must have potent anti-androgenic activity in androgen-sensitive cells with no or negligible agonistic activity in these cells. The compounds must also have a good anabolic activity in the muscle to avoid atrophy of the skeletal muscles which naturally occur with aging and the use of the current available anti-androgens

SUMMARY OF THE INVENTION

It is an object of the present invention to provide antiandrogens, having good affinity for the androgen receptor, while substantially lacking androgenic activity. These antiandrogens may be useful in the treatment and prevention of androgen-dependent diseases as described in more detail infra.

It is an object of the present invention to provide a compound of the schematic molecular formula, a salt or an N-oxide of thereof:

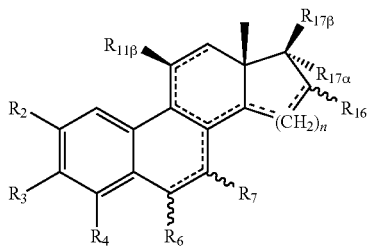

wherein n is an integer from 1 to 2;
Wherein dotted lines represent optional π-bonds;
Wherein $R_2$ and $R_4$, are independently selected from the group consisting of hydrogen, hydroxyl, hydroxymethyl, —S—$C_1$-$C_4$ alkyl, fluoro, chloro, bromo, iodo, cyano, nitro, amino, methoxy, ethoxy, acetyl, cyclopropyl, $C_1$-$C_4$ straight or branched alkyl, $C_2$-$C_4$ straight alkenyl, $C_2$-$C_4$ straight alkynyl, and fluoro, chloro, bromo, iodo, or cyano analogs of the foregoing;
Wherein $R_3$ is selected from the group consisting of hydrogen, cyano, chloro, fluoro, methoxy, ethoxy, nitro, ethynyl, propynyl, butynyl, and OR'$_3$ (R'$_3$ being selected from the group consisting of hydrogen, carbamoyl, thiocarbamoyl, amido, and acyl);
Wherein $R_6$, $R_7$, $R_{11\beta}$ are independently selected from the group consisting of hydrogen, fluoro, chloro, cyano, phenyl, $C_1$-$C_4$ straight or branched alkyl, $C_2$-$C_4$ alkenyl, $C_2$-$C_4$ alkynyl, and fluoro, chloro, bromo, iodo, or cyano analogs of the foregoing;
Wherein $R_{16}$ is selected from the group consisting of hydrogen, fluoro, chloro, cyano, pyridyl, indanyl, $C_1$-$C_4$ straight or branched alkyl, $C_2$-$C_4$ alkenyl, $C_2$-$C_4$ alkynyl, cyclopropyl, and fluoro, chloro, bromo, iodo, or cyano analogs of the foregoing;
Wherein $R_{17\alpha}$ and $R_{17\beta}$ are independently selected from the group consisting of hydrogen, dichloromethyl, OR'(wherein R' being selected from the group consisting of hydrogen, $C_1$-$C_{20}$ straight or branched alkyl, $C_2$-$C_{20}$ straight or branched alkenyl, $C_2$-$C_{20}$ straight, branched alkynyl, $C_2$-$C_{20}$ acyl and a group hydrolysed in the body), ethynyl, propynyl, butynyl, pentynyl, cyclopropylethynyl, and -A-A'-Ar
   A and A' being spacer group independently selected from the group consisting of absent, $C_1$-$C_6$ alkylene, $C_1$-$C_6$ alkenylene, $C_1$-$C_6$ alkynylene, —$SO_2$— and arylene and Ar being selected from the group consisting of substituted or un-substituted pyridyl, substituted or un-substituted pyrazinyl, substituted or un-substituted pyrimidyl, substituted or un-substituted quinolinyl, and

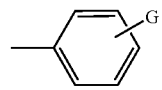

(G being selected from the group consisting of cyano, —CONR$^1$R$^2$ (R$^1$ and R$^2$ are independently selected from the group consisting of hydrogen and alkyl), hydroxyl, —S—$C_1$-$C_4$ alkyl, —CSNH$_2$, SO$_2$CH$_3$ and SOCH$_3$;
Wherein when $R_{17\alpha}$, is OR'; $R_{17\beta}$ is -A-A'-Ar, and when $R_{17\beta}$ is OR', $R_{17\alpha}$, is -A-A'-Ar;
$R_{17\alpha}$, and $R_{17\beta}$ together may form a keto group.

In one embodiment, the compound, a salt or an N-oxide derivative of thereof has the following molecular formula:

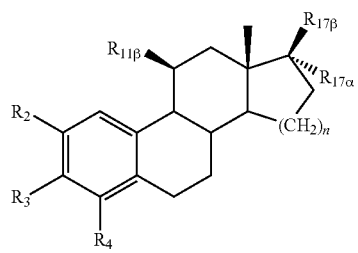

wherein n is an integer from 1 to 2;
Wherein $R_2$ is selected from the group consisting of hydrogen and fluoro;
Wherein $R_3$ is selected from the group consisting of hydrogen, cyano, chloro, methoxy, ethoxy, nitro, and propynyl;
Wherein $R_4$ is selected from the group consisting of hydrogen, fluoro, chloro, bromo, cyano, amino, cyclopropyl, $C_1$ alkyl, and fluoro analogs of the foregoing;
Wherein $R_{11\beta}$, is selected from the group consisting of hydrogen, fluoro, $C_1$-$C_2$ alkyl, and $C_2$ alkenyl;
Wherein $R_{17\alpha}$ and $R_{17\beta}$ are independently selected from the group consisting of hydroxyl, methoxy and -A-A'-Ar
   A and A' being spacer group independently selected from the group consisting of absent, —CH$_2$—, —CHF—, —CH(CH$_3$)—, propynylene, and

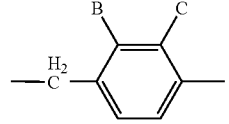

(B and C being independently selected from the group consisting of hydrogen, fluoro, and methyl), and Ar being selected from the group consisting of:

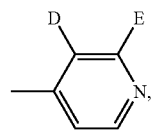

(D being selected from the group consisting of hydrogen, fluoro, chloro, bromo, methyl, ethyl and methoxy and E being selected from the group consisting of hydrogen, cyano and methyl);

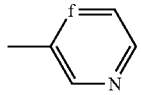

(f is CH or nitrogen);
and

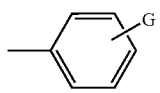

(G being selected from the group consisting of cyano, —CONR$^1$R$^2$ (R$^1$ and R$^2$ are independently selected from the group consisting of hydrogen and methyl) and —SOCH$_3$ Wherein when R$_{17\alpha}$ is hydroxyl or methoxy, R$_{17\beta}$ is -A-A'-Ar, and when R$_{17\beta}$ is hydroxyl or methoxy, R$_{17\alpha}$ is -A-A'-Ar. R$_{17\alpha}$ and R$_{17\beta}$ together may form a keto group In another embodiment a salt or an N-oxide derivative of thereof has the following molecular formula:

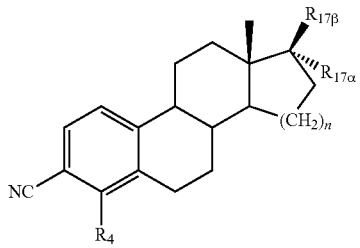

wherein n is an integer from 1 to 2;
Wherein R$_4$ is selected from the group consisting of fluoro, chloro, and methyl;
Wherein R$_{17\alpha}$ and R$_{17\beta}$ are independently selected from the group consisting of hydroxyl and —CH$_2$—Ar
Ar being selected from the group consisting of:

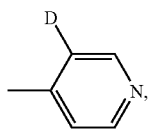

(D being selected from the group consisting of hydrogen, fluoro, and methyl);
Wherein when R$_{17\alpha}$ is hydroxyl or methoxy, R$_{17\beta}$ is —CH$_2$—Ar, and when R$_{17\beta}$ is hydroxyl or methoxy, R$_{17\alpha}$ is —CH$_2$—Ar.

In another embodiment, the invention provides a pharmaceutical composition comprising a pharmaceutically acceptable diluent or carrier and a therapeutically effective amount of at least one compound of the molecular formula, a salt or an N-oxide derivative of thereof:

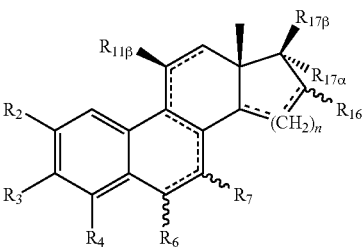

wherein n is an integer from 1 to 2;
Wherein dotted lines represent optional π-bonds;
Wherein R$_2$ and R$_4$, are independently selected from the group consisting of hydrogen, fluoro, chloro, bromo, iodo, cyano, amino, methoxy, ethoxy, cyclopropyl, C$_1$-C$_3$ straight or branched alkyl, C$_2$-C$_3$ straight alkenyl, C$_2$-C$_3$ straight alkynyl, and fluoro, chloro, bromo, iodo, or cyano analogs of the foregoing;
Wherein R$_3$ is selected from the group consisting of hydrogen, cyano, chloro, methoxy, ethoxy, nitro, and, —C≡C—CH$_3$;
Wherein R$_6$, R$_7$, R$_{11\beta}$ and R$_{16}$ are independently selected from the group consisting of hydrogen, fluoro, chloro, cyano, C$_1$-C$_3$ straight or branched alkyl, C$_2$-C$_3$ alkenyl, C$_2$-C$_3$ alkynyl, and fluoro, chloro, bromo, iodo, or cyano analogs of the foregoing;
Wherein R$_{17\alpha}$ and R$_{17\beta}$ are independently selected from the group consisting of OR' (wherein R' being selected from the group consisting of hydrogen, C$_1$-C$_{20}$ straight or branched alkyl, C$_2$-C$_{20}$ straight or branched alkenyl, C$_2$-C$_{20}$ straight, branched alkynyl, C$_2$-C$_{20}$ acyl and a group hydrolysed in the body) and -A-Ar
A being spacer group selected from the group consisting of C$_1$-C$_6$ alkyl, C$_1$-C$_6$ alkenyl, C$_1$-C$_6$ alkynyl and aryl and Ar being selected from the group consisting of substituted or un-substituted pyridyl and

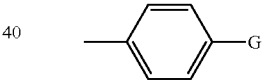

(G being selected from the group consisting of cyano, —CONR$^1$R$^2$ (R$^1$ and R$^2$ are independently selected from the group consisting of hydrogen and alkyl) and SOCH$_3$;
Wherein when R$_{17\alpha}$ is OR', R$_{17\beta}$ is -A-Ar, and when R$_{17\beta}$ is OR', R$_{17\alpha}$ is -A-Ar;
R$_{17\alpha}$ and R$_{17\beta}$ together may form a keto group.

In another embodiment, the invention provides a pharmaceutical composition comprising a pharmaceutically acceptable diluent or carrier and a therapeutically effective amount of at least one Selective Androgen Receptor Modulator of the molecular formula, a salt or an N-oxide derivative of thereof:

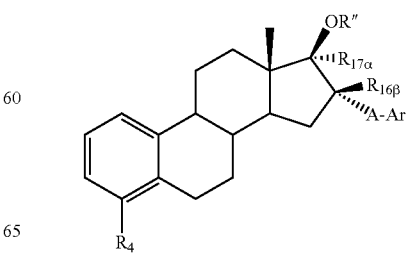

Wherein $R_4$ is selected from the group consisting of cyano, chloro, nitro, and propynyl;
Wherein $R_{16\beta}$ is selected from the group consisting of hydrogen, and $C_1$-$C_5$ alkyl, $C_1$-$C_5$ alkenyl, and $C_1$-$C_5$ alkynyl;
Wherein $R_{17\alpha}$ is selected from the group consisting of hydrogen, and $C_1$-$C_5$ alkyl, $C_1$-$C_5$ alkenyl, and $C_1$-$C_5$ alkynyl;
Wherein R" is selected from the group consisting of hydrogen, and $C_1$-$C_5$ alkyl, $C_1$-$C_5$ alkenyl, and $C_1$-$C_5$ alkynyl;
Wherein A is group selected from the group consisting of —$CH_2$—, —CHF—, —CH($CH_3$)—, propynylene, and

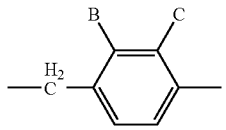

(B and C being independently selected from the group consisting of hydrogen, fluoro, and methyl),
Wherein Ar being selected from the group consisting of:

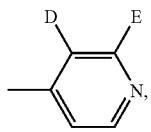

(D being selected from the group consisting of hydrogen, fluoro, chloro, bromo, methyl, ethyl and methoxy and E being selected from the group consisting of hydrogen, cyano and methyl);

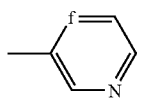

(f is CH or nitrogen);
and

(G being selected from the group consisting of cyano, —$CONR^1R^2$ ($R^1$ and $R^2$ are independently selected from the group consisting of hydrogen and methyl) and —$SOCH_3$.

In another embodiment, the invention provides topical or systemic pharmaceutical compositions containing the compounds of the invention together with pharmaceutically acceptable diluents or carriers.

In another aspect, compounds of the invention, or pharmaceutical compositions containing them, are used in the treatment or prevention of androgen-exacerbated skin related diseases such as acne, hirsutism, seborrhea, androgenic alopecia, male baldness and the like.

In another embodiment, compounds of the invention are used in the treatment or prevention of androgen-exacerbated systemic diseases such as prostate cancer or benign prostatic hyperplasia, precocious puberty, polycystic ovarian syndrome, hyperrandrogenic syndromes, and the like.

In another embodiment, treatment and prevention regimens for androgen-exacerbated diseases include use of the compounds disclosed herein, as part of a combination therapy which further utilizes other active compounds selected from the group consisting of 5alpha-reductase inhibitor, 17beta-hydroxysteroid dehydrogenase type 5 and type 13 inhibitors, and other inhibitors of androgen biosynthesis.

In another aspect, compounds of the present invention having tissue-specific antiandrogenic activity and tissue-specific androgenic activity can be used to treat or reduce the risk of developing diseases related to loss of androgenic stimulation.

It is another object to provide selective androgen receptor modulators for treatment (or reduction of the likelihood of acquiring) diseases related to loss of androgen stimulation such as muscle atrophy and weakness, benign prostatic hyperplasia skin atrophy, bone loss, anemia, arteriosclerosis, cardiovascular disease, loss of energy, loss of well-being, type 2 diabetes, abdominal fat accumulation and prostate cancer It is another object to provide treatment or reduction of the risk of developing muscle atrophy and weakness, benign prostatic hyperplasia skin atrophy, bone loss, anemia, arteriosclerosis, cardiovascular disease, loss of energy, loss of well-being, type 2 diabetes, abdominal fat accumulation and prostate cancer In another aspect, compounds of the invention are used in the manufacture of a medicament for treatment of diseases discussed herein.

It is another object to provide pharmaceutical compounds with good systemic bioavailability.

DETAILED DESCRIPTION OF THE PREFERRED EMBODIMENTS

Figure 1:
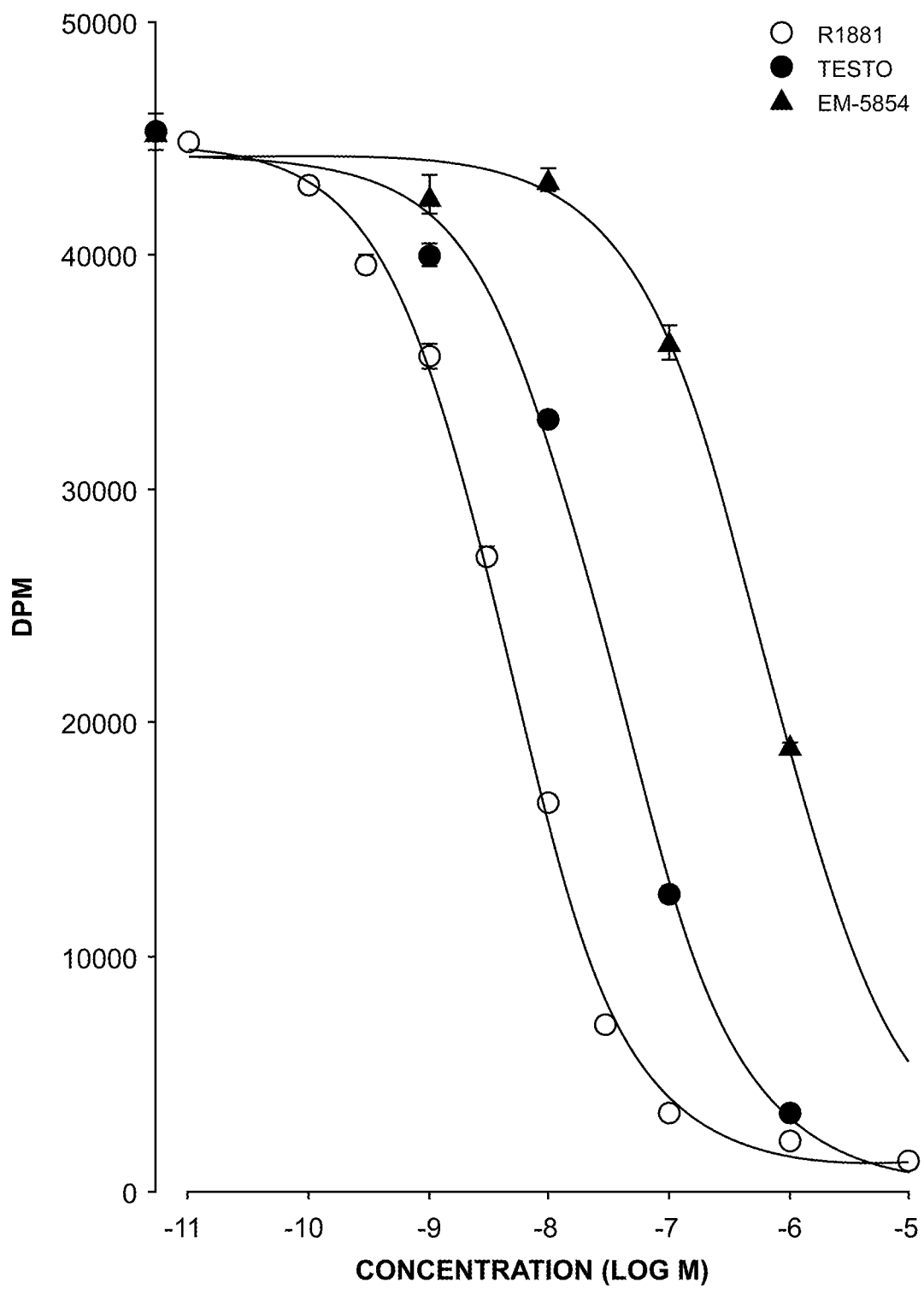
FIG. 1 shows the binding of EM-5854 to Human Androgen Receptor.
Figure 2:
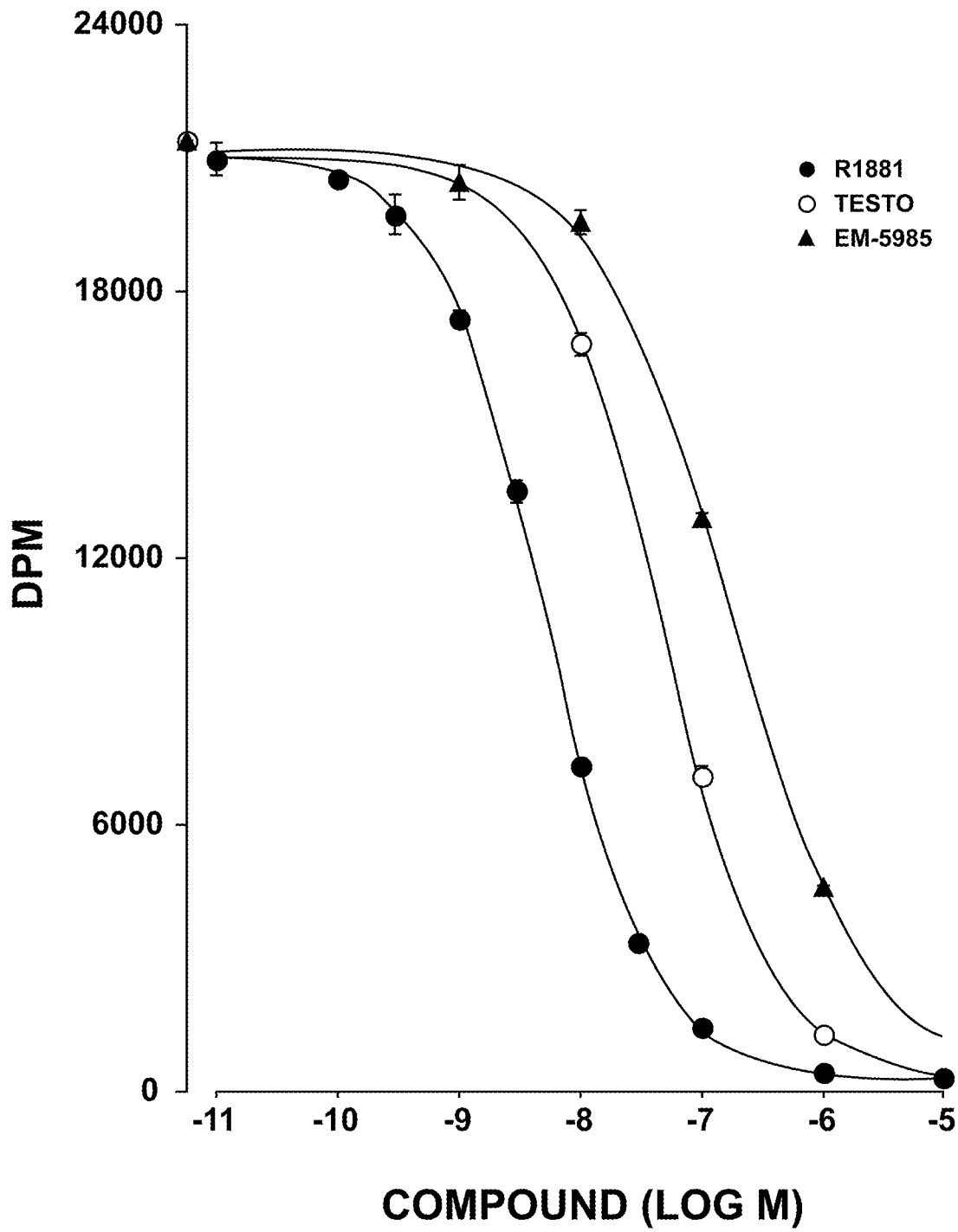
FIG. 2 shows the binding of EM-5985 to Human Androgen Receptor.
Figure 3:
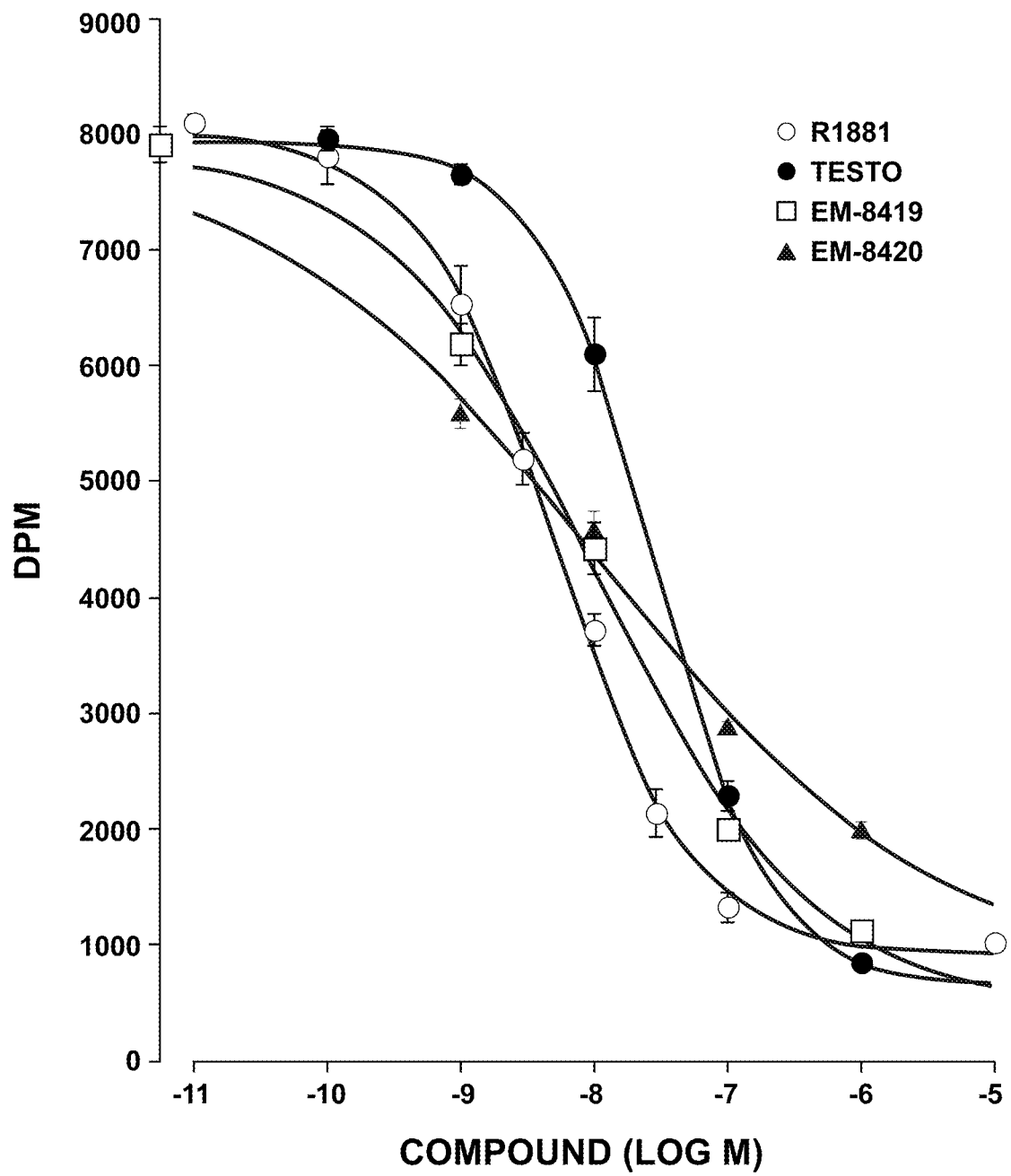
FIG. 3 shows the binding of EM-8419 and EM-8420 to Human Androgen Receptor.
Figure 4:
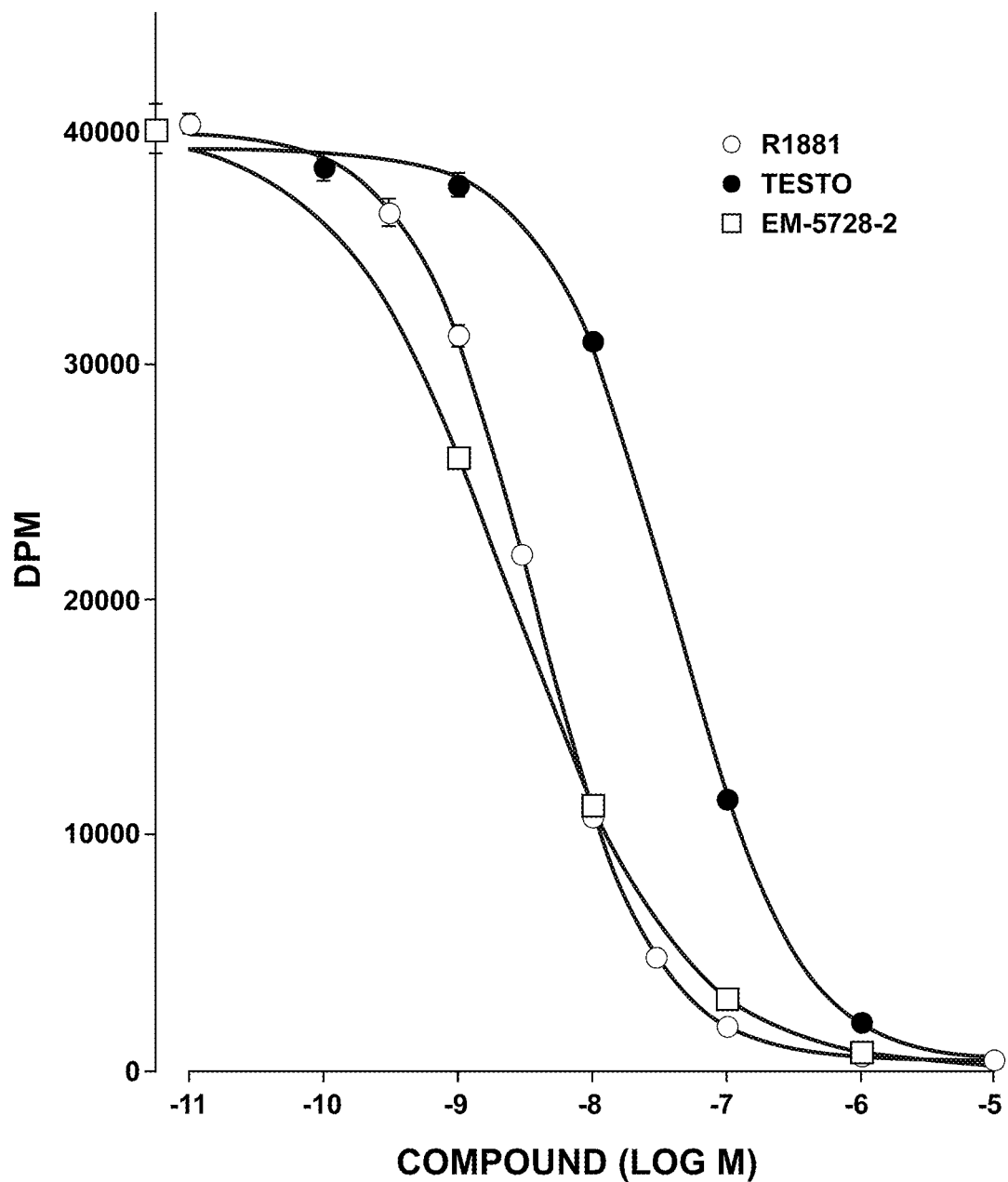
FIG. 4 shows the binding of EM-5728 to Human Androgen Receptor.
Figure 5:
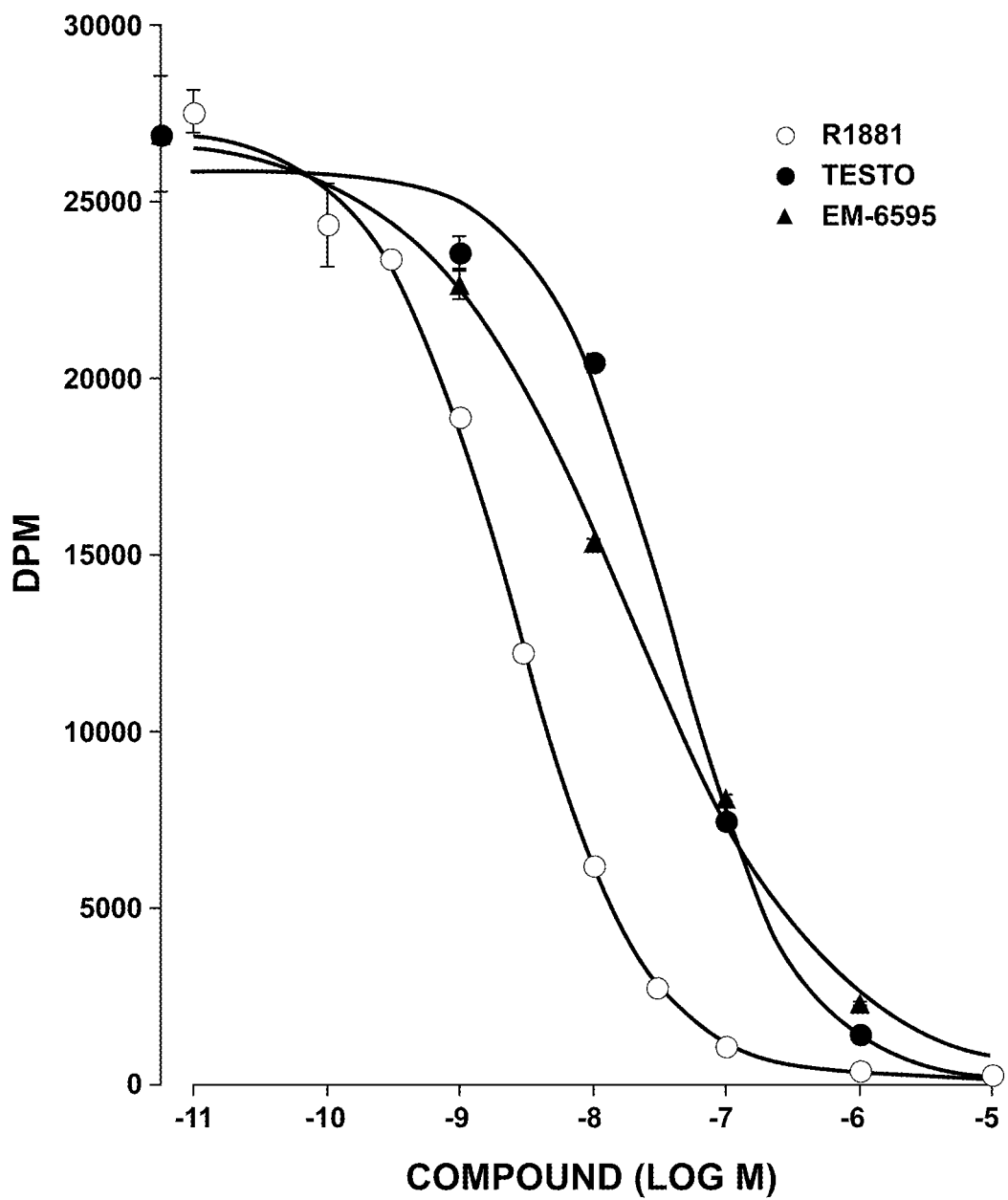
FIG. 5 shows the binding of EM-6595 to Human Androgen Receptor.
Figure 6:
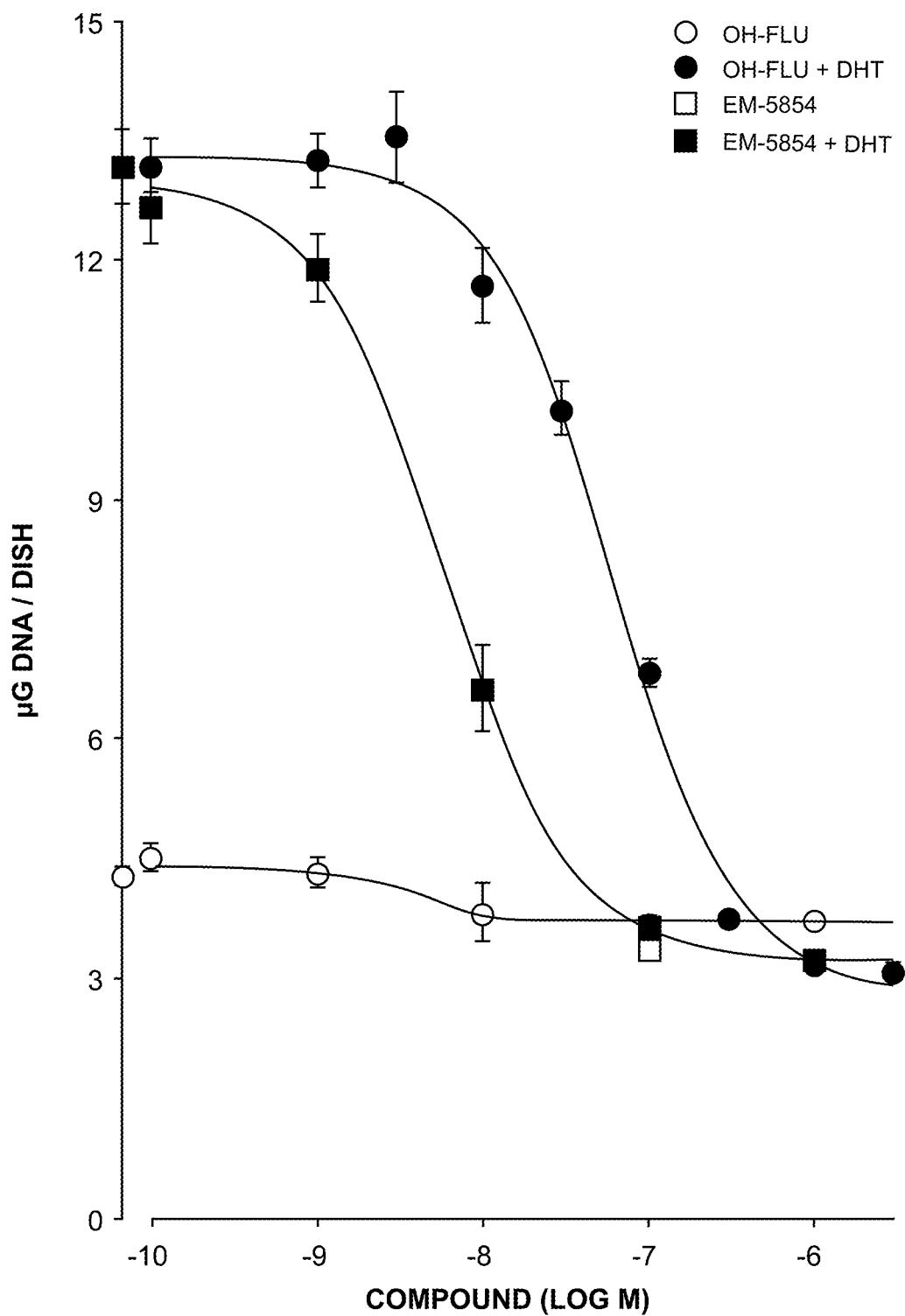
FIG. 6 illustrates the effect of EM-5854 on the proliferation of androgen-sensitive mammary carcinoma Shionogi cells in the presence or absence of DHT. OH-FLU is used as reference.

Antiandrogens having a molecular structure selected from the group consisting of, and pharmaceutical composition comprising these ones, are particularly preferred:

EM-5854

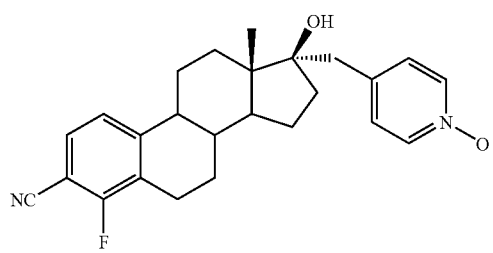

EM-5985

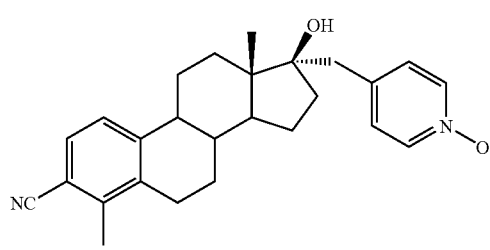

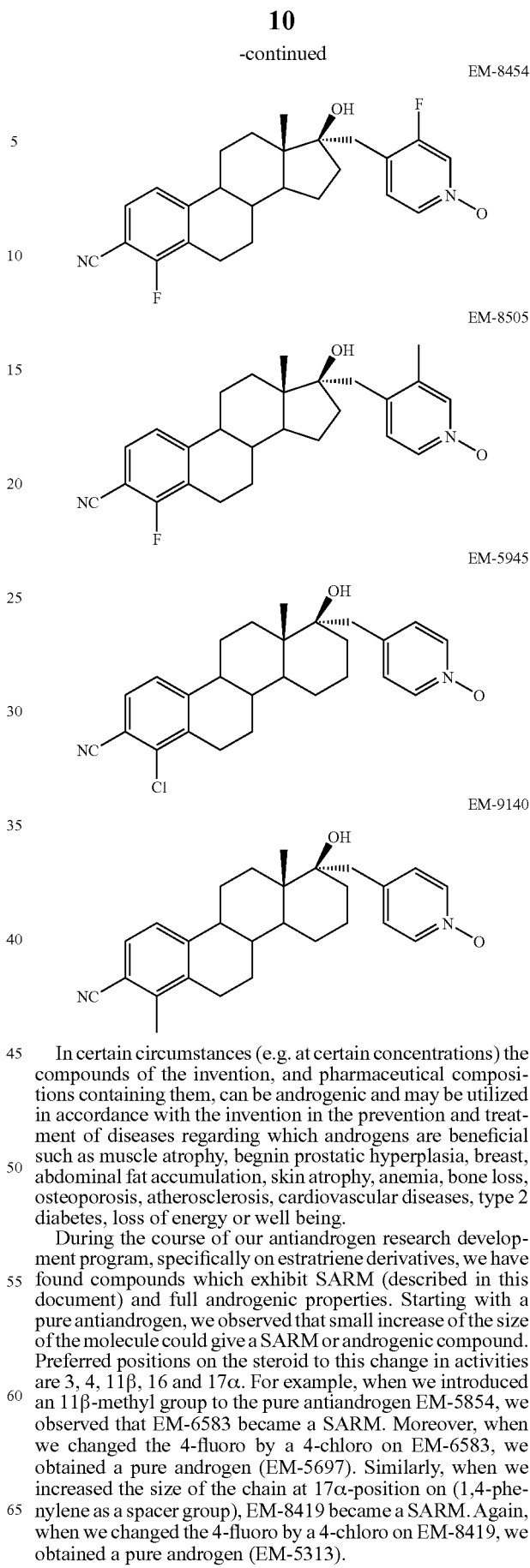

In certain circumstances (e.g. at certain concentrations) the compounds of the invention, and pharmaceutical compositions containing them, can be androgenic and may be utilized in accordance with the invention in the prevention and treatment of diseases regarding which androgens are beneficial such as muscle atrophy, begnin prostatic hyperplasia, breast, abdominal fat accumulation, skin atrophy, anemia, bone loss, osteoporosis, atherosclerosis, cardiovascular diseases, type 2 diabetes, loss of energy or well being.

During the course of our antiandrogen research development program, specifically on estratriene derivatives, we have found compounds which exhibit SARM (described in this document) and full androgenic properties. Starting with a pure antiandrogen, we observed that small increase of the size of the molecule could give a SARM or androgenic compound. Preferred positions on the steroid to this change in activities are 3, 4, 11β, 16 and 17α. For example, when we introduced an 11β-methyl group to the pure antiandrogen EM-5854, we observed that EM-6583 became a SARM. Moreover, when we changed the 4-fluoro by a 4-chloro on EM-6583, we obtained a pure androgen (EM-5697). Similarly, when we increased the size of the chain at 17α-position on (1,4-phenylene as a spacer group), EM-8419 became a SARM. Again, when we changed the 4-fluoro by a 4-chloro on EM-8419, we obtained a pure androgen (EM-5313).

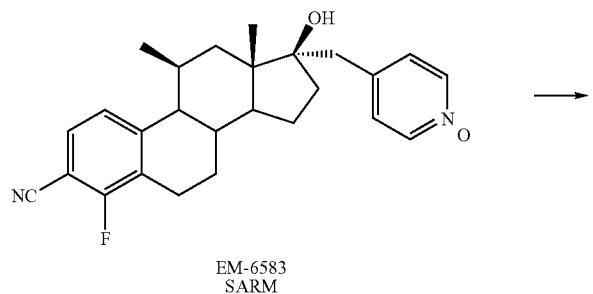
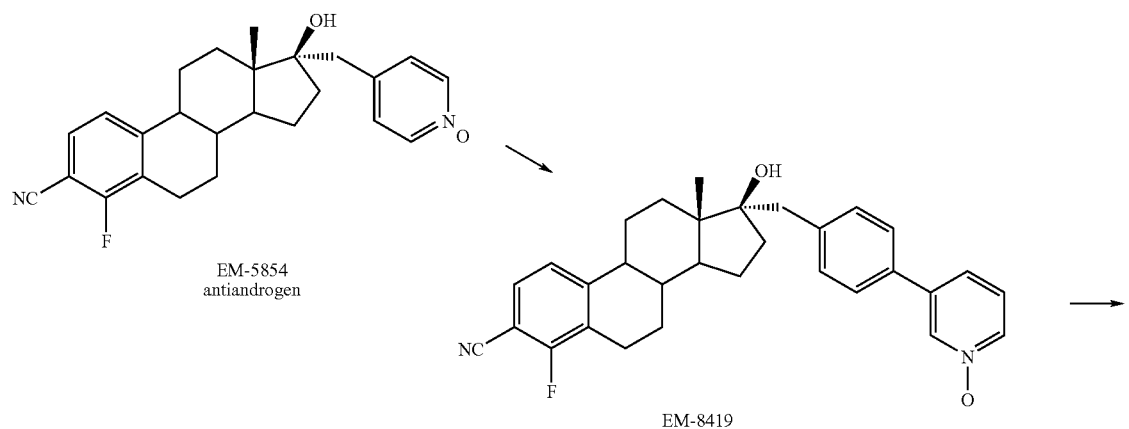
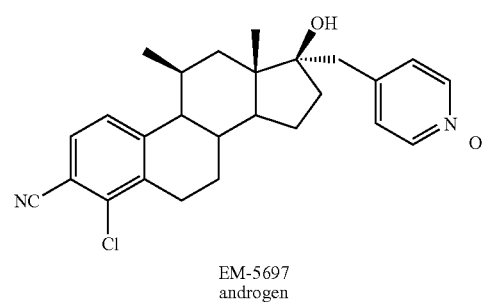
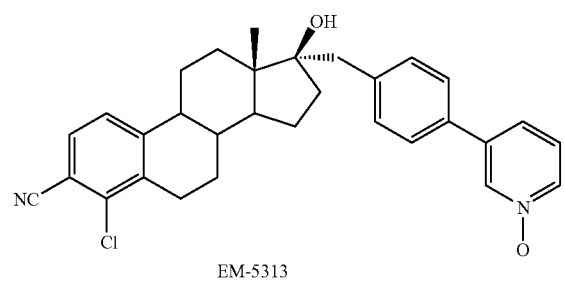

We did not quantify this phenomenon yet but we observed that the affinity to androgen receptor have generally increased when we reached pure androgenic compounds. We also believed that a larger size increase could reverse the observed tendency (androgen to SARM or antiandrogen). Thus, it is not obvious to make good predictions of the biological activity of this compound family but some trends are observable.

Selective Androgen Receptor Modulator having a molecular structure selected from the group consisting of, and pharmaceutical composition comprising these ones, are particularly preferred:

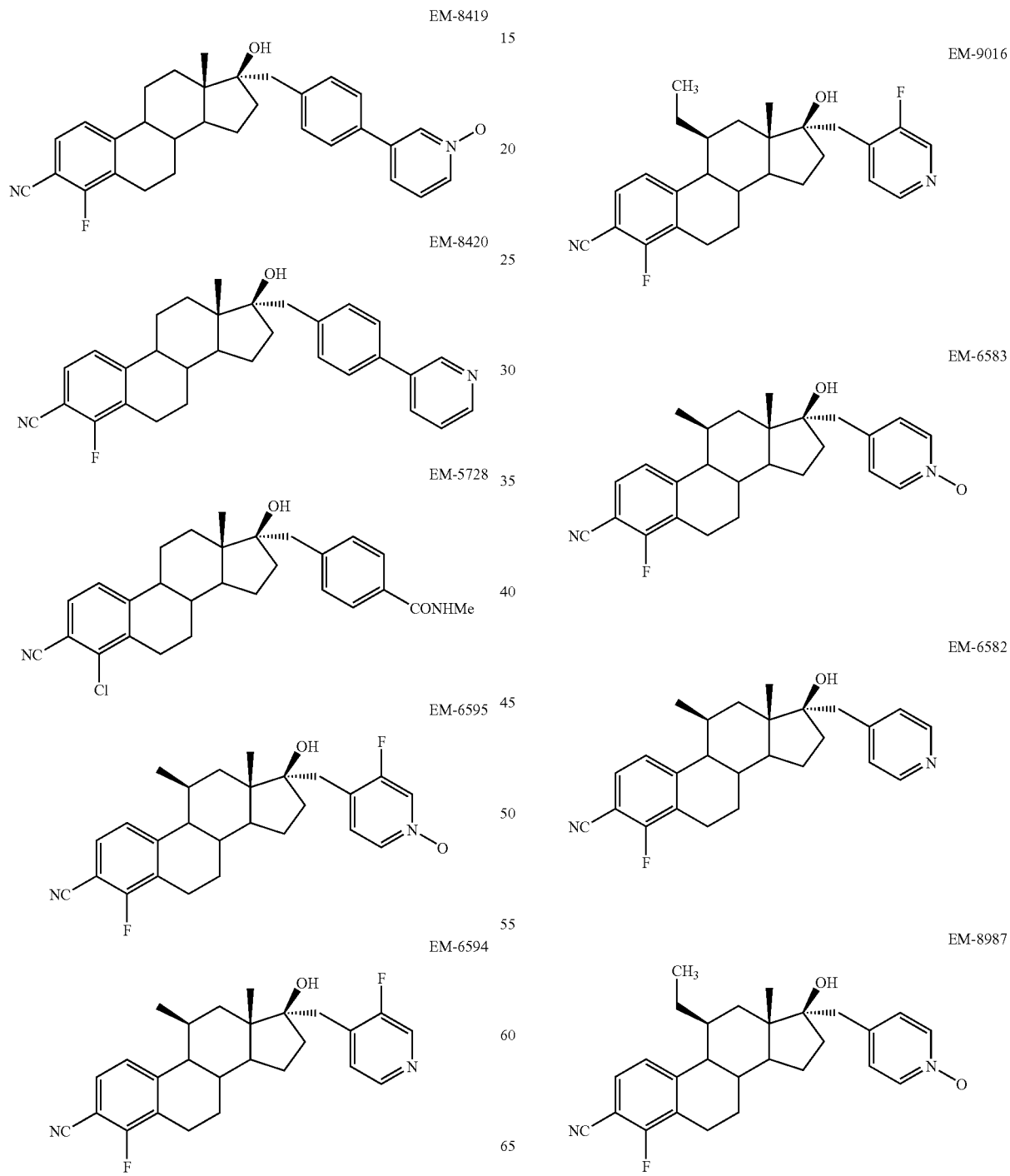

EM-3585

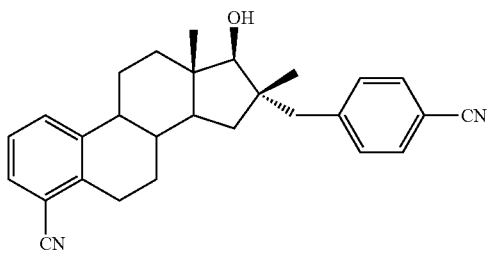

Antiandrogens or SARMs of the invention are preferably formulated together with pharmaceutically acceptable diluents, excipients or carriers (including capsules) into pharmaceutical compositions at conventional antiandrogen concentrations for antiandrogens used in the prior art. Taking into account the higher potency of the compounds of this invention, the attending clinician may elect to modify the concentration and/or dosage in order to adjust the dose to the particular response of each patient. Preferably, the attending clinician will, especially at the beginning of treatment, monitor an individual patient's overall response and serum levels of antiandrogen or SARM (in comparison to the preferred serum concentrations discussed below), and monitor the patient's overall response to treatment, adjusting dosages as necessary where a given patients' metabolism or reaction to treatment is atypical. As discussed in more detail below, carriers, excipients or diluents include solids and liquids. When a composition is prepared other than for immediate use, an art-recognized preservative is typically included (e.g. benzyl alcohol). The novel pharmaceutical compositions of the invention may be used in the treatment of androgen-related diseases, or to reduce the likelihood of acquiring such diseases. When administered systemically (e.g., for treatment of prostate cancer, benign prostatic hyperplasia, precocious puberty, polycystic ovarian syndrome and other diseases not primarily affecting the skin) conventional diluents or carriers which are known in the art to be pharmaceutically acceptable for systemic use are used, e.g., saline, water, aqueous ethanol, oil, etc. The carrier is often a mixture of ingredients.

When formulated for systemic use, the antiandrogens or SARMs may be prepared for administration in conventional ways such as orally or by injection. The antiandrogen can be administered, for example, by the oral route. The compounds of the present invention may be formulated with conventional pharmaceutical excipients, (e.g. spray dried lactose and magnesium stearate) into tablets or capsules for oral administration. Of course, taste-improving substances can be added in the case of oral administration forms. When capsules for oral ingestion are desired, any pharmaceutical capsules known in the art may be filled with the active ingredients of the invention, with or without additional diluents and other additives discussed herein.

The active substance can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol.

As further forms, one can use plug capsules, e.g. of hard gelatin, as well as closed soft-gelatin capsules comprising a softener or plasticizer, e.g. glycerine. The plug capsules contain the active substance preferably in the form of granulate, e.g. in mixture with fillers, such as lactose, saccharose, mannitol, starches, such as potato starch or amylopectin, cellulose derivatives or highly dispersed silicic acids. In soft-gelatin capsules, the active substance is preferably dissolved or suspended in suitable liquids, such as vegetable oils or liquid polyethylene glycols.

A dry delivery system, as described in U.S. Pat. Nos. 3,742, 951, 3,797,494 or 4,568,343 may be used.

Alternatively, the active ingredient may be placed into a transdermal patch having structures known in the art, for example, structures such as those set forth in E.P. Patent No. 0279982.

Solvents or devices as described in U.S. Pat. Nos. 5,064, 654, 5,071,644 or 5,071,657 can also be used to facilitate transdermal penetration when systemic effects are desired. When used to treat systemic diseases, the site of application on the skin should be changed in order to avoid excess local concentration of antiandrogens.

In some embodiments, the antiandrogens of the invention are utilized for the treatment of androgen-related diseases of the skin such as acne, seborrhea, hirsutism, androgenic alopecia and male baldness. When used for any of these purposes, the antiandrogens are preferably administered topically together with a conventional topical carrier or diluent. When used topically, it is preferred that the diluent or carrier does not promote transdermal penetration of the active ingredients into the blood stream or other tissues where they might cause unwanted systemic effects.

When the compound is administered in a cutaneous or topical carrier or diluent, the carrier or diluent may be chosen from any known in the cosmetic and medical arts, e.g. any gel, cream, lotion, ointment, liquid or non liquid carrier, emulsifier, solvent, liquid diluent or other similar vehicle which does not exert deleterious effect on the skin or other living animal tissue. The carrier or diluent is usually a mixture of several ingredients, including, but not limited to liquid alcohols, liquid glycols, liquid polyalkylene glycols, water, liquid amides, liquid esters, liquid lanolin, lanolin derivatives and similar materials. Alcohols include mono and polyhydric alcohols, including ethanol, glycerol, sorbitol, isopropanol, diethylene glycol, propylene glycol, ethylene glycol, hexylene glycol, mannitol and methoxyethanol. Typical carriers may also include ethers, e.g. diethyl and dipropyl ether, methoxypolyoxyethylenes, carbowaxes, polyethyleneglycerols, polyoxyethylenes and sorbitols. Usually, the topical carrier includes both water and alcohol in order to maximize the hydrophylic and lipophylic solubility, e.g. a mixture of ethanol or isopropanol with water.

A topical carrier may also include various other ingredients commonly used in ointments and lotions and well known in the cosmetic and medical arts. For example, fragrances, antioxidants, perfumes, gelling agents, thickening agents such as carboxymethylcellulose, surfactants, stabilizers, emollients, coloring agents and other similar agents may be present.

The concentration of active ingredient in the ointment, cream, gel or lotion is typically from about 0.1 to 20 percent preferably between 0.5 and 5 percent and most preferably 2 percent (by weight relative to the total weight of the lotion, cream, gel or ointment). Within the preferred ranges, higher concentrations allow a suitable dosage to be achieved while applying the lotion, ointment, gel or cream in a lesser amount or with less frequency.

Several non-limiting examples infra describe the preparation of a typical lotion and gel, respectively. In addition to vehicles, one skilled in the art may choose other vehicles in order to adapt to specific dermatologic needs.

When antiandrogens or SARMs are administered systemically, they are preferably administered orally or parenterally. Naturally, topical administration is preferred when the desired site of action is the skin.

Concentration of the active antiandrogen or SARMs varies in a known manner depending upon the method of administering the pharmaceutical composition. A composition suitable for oral administration may preferably include at least one antiandrogen wherein the total concentration of all such antiandrogens in said pharmaceutical composition is from about 1% to 95% of the composition (by weight), and preferably from about 5% to about 20%. Where a combination of antiandrogens is used, the total dosage of the sum of all antiandrogens should be equal to the dosage range recited above. Blood level of the antiandrogen is a preferred criteria of adequate dosage which takes into account individual variation in absorption and metabolism.

When prepared for parental injection, the antiandrogen or SARM is preferably added at a concentration between about 0.1 mg/ml and about 100 mg/ml (preferably about 2.5 mg/ml to about 25 mg/ml).

When systemic activity is desired, it is necessary only that the antiandrogen or SARM be administered in a manner and at a dosage sufficient to allow blood serum concentration to obtain desired levels. Serum antiandrogen concentration should typically be maintained between 0.1 and 1000 micrograms per liter, preferably between 50 and 1000 micrograms per liter and most preferably between 50 and 500 micrograms per liter. Adequate serum levels may also be assessed by a patient's response to therapy.

For typical patients, the appropriate dosage of the antiandrogen or SARM to achieve desired serum concentration is between 10 and 2000 milligrams of active ingredient per day per 50 kg of body weight when administered orally. When administered by injection, about 2 to 1500 mg per day per 50 kg of body weight is recommended, preferably from 5 to 100.

For topical use lotion, ointment, gel or cream should be thoroughly rubbed into the skin so that no excess is plainly visible, and the skin is preferably not washed in that region for at least 30 minutes. The amount applied should provide at least 0.02 milligrams of antiandrogen or SARM per square centimeter (preferably from 0.1 to 1 mg/cm$^2$) per application. It is desirable to apply the topical composition to the effected region from 1 to 6 times daily, e.g. 3 times daily at approximately regular intervals.

In some embodiments of the invention, the antiandrogen of the invention is used in combination with another active ingredient as part of a combination therapy. For example, the novel antiandrogen may be utilized together with a separate 5α-reductase inhibitor, a type 5 or type 3 17β-hydroxysteroid dehydrogenase inhibitor, or a Prostate Short-Chain Dehydrogenase Reductase 1 inhibitor which may be incorporated into the same pharmaceutical composition as is the antiandrogen, or which may be separately administered. Combination therapy could thus include treatment with one or more compounds which inhibit the production of dihydrotestosterone or its precursors. In some preferred embodiments of the invention, the topical pharmaceutical composition further includes an inhibitor of steroid 5α-reductase activity. One such inhibitor ("Propecia or Proscar") is commercially available form Merck Sharp and Dohme. Another inhibitor <<Dutasteride>> which inhibits both 5α-reductase co-enzymes is also commercially available from GlaxoSmithKline. Inhibitors of type 5 17β-hydroxysteroid dehydrogenase (more particularly compound EM-1404) are disclosed in the international publication WO 99/46279. EM-1791, one of inhibitors type 13 17β-hydroxysteroid dehydrogenase is described in WO 2005/066194.

When 5alpha-reductase inhibitors are used in combination therapies, in accordance with the invention described herein, oral dosage is preferably between 0.1 mg and 100 mg per day per 50 kg body weight, more preferably between 0.5 mg/day and 10 mg/day, for example 5.0 mg per day of finasteride or 0.5 mg per day of dutasteride.

When type 5 17beta-hydroxysteroid dehydrogenase inhibitors are used in combination therapies, in accordance with the invention described herein, oral dosage is preferably between 5 mg and 500 mg per day per 50 kg body weight, more preferably between 10 mg/day and 400 mg/day, for example 300 mg per day of EM-1404.

When 17β-hydroxysteroid dehydrogenease type 5 or type 13 inhibitors are used in combination therapies, in accordance with the invention described herein, oral dosage is preferably between 10 mg and 1000 mg per day per 50 kg body weight, more preferably between 25 mg/day and 1000 mg/day, for example 200 mg per day of EM-1404 or EM-2881.

A patient in need of treatment or reducing the risk of onset of a given disease is one who has either been diagnosed with such disease or one who is susceptible to acquiring such disease. The invention is especially useful for individuals who, due to heredity, environmental factors or other recognized risk factor, are at higher risk than the general population of acquiring the conditions to which the present invention relates.

Except where otherwise stated, the preferred dosage of the active compounds of the invention is identical for both therapeutic and prophylactic purposes. The dosage for each active component discussed herein is the same regardless of the disease being treated (or prevented).

Where two are more different active agents are discussed as part of a combination therapy herein (e.g. an enzyme inhibitor and an antiandrogen), a plurality of different compounds are administered rather than a single compound having multiple activities.

Except where otherwise indicated, the term "compound" and any associated molecular structure may include any possible stereoisomers thereof, in the form of a racemic mixture or in optically active form.

Except where otherwise noted or where apparent from context, dosages herein refer to weight of active compounds unaffected by pharmaceutical excipients, diluents, carriers or other ingredients, although such additional ingredients are desirably included, as shown in the examples herein. Any dosage form (capsule, tablet, injection or the like) commonly used in the pharmaceutical industry is appropriate for use herein, and the terms "excipient", "diluent" or "carrier" include such non-active ingredients as are typically included, together with active ingredients in such dosage forms in the industry.

All of the active ingredients used in any of the combination therapies discussed herein may be formulated in pharmaceutical compositions which also include one or more of the other active ingredients. Alternatively, they may each be administered separately but sufficiently simultaneous in time so that a patient eventually has elevated blood levels or otherwise enjoys the benefits of each of the active ingredients (or strategies) simultaneously. In some preferred embodiments of the invention, for example, one or more active ingredients are to be formulated in a single pharmaceutical composition. In other embodiments of the invention, a kit is provided which includes at least two separate containers wherein the contents of at least one other container with respect to active ingredients contained therein. Two or more different containers are used in the combination therapies of the invention. Combination therapies discussed herein also include use of one active ingredient of the combination in the manufacture of a medicament for the treatment (or prevention) of the disease in question where the treatment or prevention further includes another active ingredient or strategy of the combination. For example, in prostate cancer therapy an LHRH agonist or antagonist or an inhibitor of type 3 17β-hydroxysteroid dehydrogenase can be used.

PREFERRED COMPOUNDS

Set forth in the tables below are lists of preferred compounds and their properties and efficacy. The table 1 and 4 include in vitro determination of androgenic/antiandrogenic activity on mouse mammary carcinoma Shionogi cells and determination of the binding to Human Androgen. Receptors in transfected cells and in vivo data determination of antiandrogenic activity on rat. Detailed explanations of how the data were collected and reported follow the tables. The table II includes in vivo determination of androgenic/antiandrogenic activity on immature male rat and bioavailability data Column 3 represents the dose (expressed in nM) that inhibits by 50% ($IC_{50}$) the DHT-stimulated Shionogi mouse mammary carcinoma cell number. Lower values are preferable.
Column 4 represents the Relative Binding Affinity (RBA) of the antiandrogen expressed as percentage (%) on Rat Androgen Receptor relative to R1881 as calculated by the formula:

$$\% \text{RBA} = 100 \times IC_{50}R1881/IC_{50}(\text{compound})$$

TABLE 1

In vitro Results

| NAME 1 | Shionogi cells Antiandrogenic activity Ki OH-Flu/ Ki compound 2 | Ki (nM) 3 | Rat Androgen Receptor Binding RBA (%) R1881 = 100% 4 | Human Androgen Receptor Binding RBA (%) R1881 = 100% 5 |
|---|---|---|---|---|
| Hydroxyflutamide | 1 | 16.8 ± 0.5 (n = 312) | 0.1 | 0.21 ± 0.09 (n = 3) |
| bicalutamide | 0.23 ± 0.03 (n = 3) | 48 ± 9 (n = 3) | 0.2 | 0.3 |
| EM-5854 | 5.5 ± 1.2 (n = 7) | 2.5 ± 0.4 (n = 7) | 0.4 ± 0.1 (n = 2) | 0.63 ± 0.08 (n = 5) |
| EM-5987 | 22 ± 7 (n = 2) | 0.35 ± 0.15 (n = 2) | ND | 6.8 ± 1.7 (n = 2) |
| EM-5985 | 12 ± 4 (n = 4) | 0.9 ± 0.2 (n = 4) | 0.6 | 2.0 ± 0.3 (n = 4) |
| EM-5855 | 11 ± 1 (n = 2) | 1.0 ± 0.2 (n = 2) | ND | 8.2 ± 0.5 (n = 2) |
| EM-8454 | 2.7 | 2.2 | ~0.3 | ~1 |
| EM-8505 | 4.4 | 4.2 | ~0.3 | ~0.3 |
| EM-8455 | 3.1 | 1.9 | ND | 9.1 |
| EM-8504 | 7.5 | 2.5 | ND | 6.1 |
| EM-8632 | 2.1 | 4.1 | ND | 47 |
| EM-4350 | 20 | 0.9 | ND | 63 |
| EM-5988 | mixed | mixed | ND | 97 ± 19 (n = 2) |
| EM-5984 | 4.0 | 1.9 | ND | 29 |
| EM-8633 | 15 | 0.8 | ND | 2.3 |
| EM-4240 | 1.4 | 24 | ND | 110 |
| EM-5945 | 13 | 0.9 | 0.3 | 2.8 ± 0.4 (n = 2) |
| EM-5943 | 29 ± 26 (n = 2) | 2.1 ± 1.8 (n = 2) | ND | 26 |
| EM-9140 | 11 | 1.2 | ND | 1.4 |
| EM-9139 | 15 | 0.8 | ND | 1.6 |

Results were obtained from one experiment unless otherwise specified (n = number of experiments)

Legend of the table 1:
In Column 1, the laboratory names of the antiandrogens are reported.
In Column 2 represents the ratio in % of the $IC_{50}$ of the inhibition by hydroxyflutamide of the DHT-stimulated Shionogi mouse mammary carcinoma cell number versus the $IC_{50}$ of the inhibition by the antiandrogen. Higher values are preferable.

Higher values are preferable
Column 5 represents the Relative Binding Affinity (RBA) of the antiandrogen expressed as percentage (%) on Human Androgen Receptor in transfected cells relative to R1881 as calculated by the formula:

$$\% \text{RBA} = 100 \times IC_{50}R1881/IC_{50}(\text{compound})$$

Higher values are preferable

TABLE 2

In vivo Results

| NAME 1 | Plasma AUC 0.5 mg, po (Rat) (ng · h/mL) 2 | Prostate Conc, 7 h (Rat) (ng/g) 3 | In Vivo Agonist Immature Rat CX 0.1 mg/rat/po/ID [0.5 mg/rat/po/ID] % Change vs CX (DHT = +100%) VP 4 | SV 5 | In Vivo Antagonist Immature Rat CX + DHT 0.1 mg/rat/po/ID [0.5 mg/rat/po/ID] % Change vs DHT (CX = −100%) VP 6 | SV 7 |
|---|---|---|---|---|---|---|
| Casodex | 8497 ± 386 (24 h) | ND | (0; 0.2 mg, sc) | (0; 0.2 mg, sc) | [−51 ± 9] (n = 6) | [−86 ± 2] (n = 6) |

TABLE 2-continued

In vivo Results

| NAME | Plasma AUC 0.5 mg, po (Rat) (ng·h/mL) | Prostate Conc, 7 h (Rat) (ng/g) | In Vivo Agonist Immature Rat CX 0.1 mg/rat/po/ID [0.5 mg/rat/po/ID] % Change vs CX (DHT = +100%) | | In Vivo Antagonist Immature Rat CX + DHT 0.1 mg/rat/po/ID [0.5 mg/rat/po/ID] % Change vs DHT (CX = −100%) | |
|---|---|---|---|---|---|---|
| 1 | 2 | 3 | VP 4 | SV 5 | VP 6 | SV 7 |
| Flutamide (Flu) | 39 ± 4 (24 h) OH-Flu: 4059 ± 259 | ND | (1; 0.2 mg, sc) | (0; 0.2 mg, sc) | −26 ± 2 (n = 6) [−48 ± 1] (n = 131) | −62 ± 4 (n = 6) [−83 ± 1] (n = 131) |
| (OH-Flu) | 5378 ± 820 (24 h) | ND | | | | |
| EM-5854 | 2933 ± 233 (7 h) | ND | +1 ± 1 [+1 ± 1] | 0 [0] | −46 ± 2 (n = 13) [−76 ± 4] (n = 2) | −86 ± 2 (n = 13) [−85 ± 3] (n = 2) |
| EM-5987 | ND | ND | ND | ND | [−69 ± 1] (n = 2) | [−83 ± 8] (n = 2) |
| EM-5985 | 3709 ± 397 (7h) | ND | [0] | [0] | −42 ± 0 (n = 2) [−69 ± 3] (n = 2) | −85 ± 2 (n = 2) [−84 ± 3] (n = 2) |
| EM-5855 | ND | ND | [2 ± 1] | [1 ± 4] | −43 ± 10 (n = 2) [−65 ± 4] (n = 2) | −81 ± 1 (n = 2) [−84 ± 7] (n = 2) |
| EM-8454 | ND | ND | 0 | 0 | −50 ± 4 (n = 2) [−56 ± 4] | −88 ± 1 (n = 2) [−89 ± 1] |
| EM-8505 | ND | ND | ND | ND | −53 ± 4 (n = 3) [−66 ± 4] | −85 ± 2 (n = 3) [−90 ± 1] |
| EM-8455 | ND | ND | 0 | +1 ± 2 | −49 ± 3 | −85 ± 4 |
| EM-8504 | ND | ND | ND | ND | −51 ± 13 (n = 2) | −75 ± 2 (n = 2) |
| EM-8632 | ND | ND | ND | ND | −43 ± 6 | −74 ± 3 |
| EM-4350 | ND | ND | +3 ± 2 | +3 ± 4 | −27 ± 7 [−51 ± 7] | −59 ± 2 [−75 ± 6] |
| EM-5988 | ND | ND | +10 ± 0 | +10 ± 0 | [−71 ± 5] (n = 2) | [−83 ± 3] (n = 2) |
| EM-5984 | ND | ND | 0 | 0 | −43 ± 10 (n = 2) [−47 ± 8] (n = 2) | −77 ± 1 (n = 2) [−79 ± 5] (n = 2) |
| EM-8633 | ND | ND | 0 | 1 | −42 ± 5 (n = 2) | −83 ± 0 (n = 2) |
| EM-4240 | ND | ND | +12 ± 3 | +3 ± 1 | −46 ± 9 [−52 ± 4] | −58 ± 2 [−85 ± 2] |
| EM-5945 | 11377 ± 83 (24 h) | 1539 | +3 ± 1 [+4 ± 3] | +2 ± 2 [+4 ± 1] | −47 ± 2 (n = 4) [−56 ± 5] (n = 2) | −80 ± 2 (n = 4) [−87 ± 8] (n = 2) |
| EM-5943 | ND | ND | +2 ± 2 | +3 ± 4 | −44 ± 7 [−52 ± 7] (n = 2) | −71 ± 4 [−89 ± 8] (n = 2) |
| EM-9140 | ND | ND | 0 | 0 | −44 ± 1 (n = 2) [−59 ± 2] | −73 ± 0 (n = 2) [−89 ± 2] |
| EM-9139 | ND | ND | +2 ± 2 | 0 | −21 ± 7 | −48 ± 7 |

Results were obtained from one experiment unless otherwise specified (n = number of experiments)
VP = Ventral prostate; SV = Seminal vesicles; Conc = Concentration; ID = Once daily; po = Oral; Cx = Castrated.

Legend of the table 2:

In Column 1, the laboratory names of the antiandrogens are reported.

Column 2 represents the rat oral absorption of the compound expressed in plasma Area Under the Curve (AUC).

Column 3 represents the concentration at 7 hours of the compound in the prostate expressed in ng/g.

Column 4 represents the agonistic efficacy in rat prostate expressed in percentage of change calculated by the following formula:

$$\% \text{ change} = [W(\text{compound}) - W(\text{control } CX)/W(\text{control } DHT) - W(\text{control } CX)] \times 100.$$

W is the weight of the prostate.

Column 5, represents the agonistic efficacy in rat seminal vesicle expressed in percentage of change calculated by the following formula:

% change=[W(compound)−W(control CX)/W(control DHT)−W(control CX)]×100.

W is the weight of the seminal vesicles.

Column 6 represents the antiandrogenic efficacy in rat prostate, expressed in percentage of change (% change) calculated by the following formula:

% change=−100−[[W(compound)−W(control CX)/W(control DHT)−W(control CX)]×100].

W is the weight of the prostate.

Column 7 represents the antiandrogenic efficacy in rat seminal vesicles, expressed in percentage of change (% change) calculated by the following formula:

% change=−100−[[W(compound)−W(control CX)/W(control DHT)−W(control CX)]×100].

W is the weight of the seminal vesicles.

TABLE 3

In vivo Results
Mature Male Rats

Antagonistic Activity
CX+ 4-DIONE in Mature Rat

| NAME<br>1 | Dose<br>mg/rat/<br>per os/ID<br>2 | % change vs 4-DIONE Cont<br>(CX Cont = −100% inh) | |
|---|---|---|---|
| | | Ventral Prostate<br>3 | Seminal Vesicles<br>4 |
| Bicalutamide | 1 | −44 ± 7 | −82 ± 9 |
| (Casodex) | 5 | −64 ± 4 | −90 ± 6 |
| Flutamide | 1 | −47 ± 7 | −102 ± 8 |
| (Euflex) | 5 | −70 ± 3 | −106 ± 6 |
| EM-5854 | 0.2 | −34 ± 7 | −69 ± 7 |
| | 1 | −67 ± 2 | −109 ± 5 |

Legend of the table 3:

In Column 1, the laboratory names of the antiandrogens are reported.

Column 2 represents the oral dose of the antiandrogen given to mature rat.

Column 3 represents the antiandrogenic efficacy in rat prostate, expressed in percentage of change (% change) calculated by the following formula:

% change=−100−[[W(compound)−W(control CX)/W(control DHT)−W(control CX)]×100].

W is the weight of the prostate.

Column 4 represents the antiandrogenic efficacy in rat seminal vesicles, expressed in percentage of change (% change) calculated by the following formula:

% change=−100−[[W(compound)−W(control CX)/W(control DHT)−W(control CX)]−100].

W is the weight of the seminal vesicles.

TABLE 4

| | Shionogi cells<br>Androgenic/Antiandrogenic activity | | | Human<br>Androgen | |
|---|---|---|---|---|---|
| NAME<br>1 | % of stim of<br>basal at<br>$10^{-7}$M<br>(% over basal)<br>2 | % of stim of<br>basal at<br>$10^{-7}$M<br>(DHT$^a$ = 100%)<br>3 | % of inh of<br>DHT at<br>$10^{-7}$M<br>(Basal = 100%)<br>4 | Receptor<br>Binding<br>RBA (%)<br>R1881 = 100%<br>5 | AUC 24 h<br>0.5 mg/rat<br>oral<br>ng · h/mL<br>6 |
| EM-8419 | +94 ± 17<br>(n = 4) | +62 ± 11<br>(n = 4) | +21 ± 11<br>(n = 4) | 83 ± 35<br>(n = 2) | 5725 ± 595 |
| EM-8420 | +107 ± 37<br>(n = 3) | +59 ± 6<br>(n = 3) | +19 ± 11<br>(n = 3) | 46 | 236 ± 108<br>5008 ± 566 of EM-8419 |
| EM-5728 | +143 ± 27<br>(n = 3) | +79 ± 2<br>(n = 3) | +26 ± 4<br>(n = 3) | 190 ± 49<br>(n = 3) | 6387 ± 808<br>2111 ± 328 of EM-5459 |
| EM-6595 | +117 ± 11<br>(n = 2) | +43 ± 13<br>(n = 2) | −58 ± 13<br>(n = 2) | 13 | ND |
| EM-3585 | +279 | +63 | +41 | 55 | 2370 ± 253 |
| EM-6594 | +224 | +63 | +37 | 292 | ND |
| EM-9017 | +36 | +31 | +64 | 139 | ND |
| EM-9016 | +45 | +39 | +46 | 2250 ± 570<br>(n = 2) | ND |
| EM-6583 | +138 ± 49<br>(n = 2) | +52 ± 27<br>(n = 2) | +46 ± 27<br>(n = 2) | 21 | ND |
| EM-6582 | +145 ± 78<br>(n = 2) | +41 ± 22<br>(n = 2) | +59 ± 22<br>(n = 2) | 331 | ND |
| EM-8987 | +73 | +74 | +35 | 26 | ND |
| EM-8986 | +21 | +9 | +44 | 508 | ND |

$^a$DHT = 0.3 nM.

Legend of the table 4:
In Column 1, the laboratory names of the SARM are reported.
Column 2 represents the stimulation expressed in % over the basal of Shionogi mouse mammary carcinoma cell number by a $10^{-7}$ M concentration of the SARM.
Column 3 represents the stimulation of the basal, expressed in % of the difference between the DHT-stimulated and the basal of Shionogi mouse mammary carcinoma cell number by a $10^{-7}$ M concentration of the SARM.
Column 4 represents the inhibition expressed in % of the DHT-stimulated Shionogi mouse mammary carcinoma cell number by a $10^{-7}$ M concentration of the SARM.
Higher values are preferable.
Column 5 represents the Relative Binding Affinity (RBA) of the SARM expressed as percentage (%) on Human Androgen Receptor in transfected cells relative to R1881 as calculated by the formula:

% RBA=100×$IC_{50}$R1881/$IC_{50}$(compound)

Higher values are preferable
Column 6 represents the rat oral absorption of the SARM expressed in plasma Area Under the Curve (AUC).
Higher values are preferable Column 4 represents the change of bulbocavernosus muscles of intact rat expressed in percentage of change calculated by the following formula:

% change=[W(compound)−W(control CX)/W(control intact)−W(control CX)]×100.

W is the weight of the bulbocavernosus muscles.
Column 5 represents the agonist effect on prostate in castrated rat expressed in percentage of change calculated by the following formula:

% change=[W(compound)−W(control CX)/W(control DHT)−W(control CX)]×100.

W is the weight of the prostate.
Column 6 represents the agonist effect on seminal vesicle in castrated rat expressed in percentage of change calculated by the following formula:

% change=[W(compound)−W(control CX)/W(control DHT)−W(control CX)]×100.

W is the weight of the seminal vesicles.

TABLE 5

| | In Vivo Intact Rat 0.1 mg/rat/os/ID % change vs Intact CONT (Intact CONT = +100%; CX CONT = 0%) | | | In Vivo Agonist Rat CX 0.1 mg/rat/os/ID % change vs CX (DHT CONT = +100%) | | | In Vivo Anti-A Rat CX + DHT 0.1 mg/rat/po/ID [0.5 mg/rat/po/ID] % change vs DHT (CX CONT = −100%) | | |
|---|---|---|---|---|---|---|---|---|---|
| NAME 1 | VP 2 | SZ 3 | Bulbo 4 | VP 5 | SV 6 | Bulbo 7 | VP 8 | SV 9 | Bulbo 10 |
| FLU | +75 ± 4 (n = 6) (0.5 mg) | +33 ± 3 (n = 6) (0.5 mg) | +42 ± 6 (n = 6) (0.5 mg) | ND | ND | ND | [−48 ± 1] (n = 131) | [−83 ± 1] (n = 131) | [−68 ± 2] (n = 46) |
| EM-8419 | +89 ± 5 (n = 2) | +76 ± 2 (n = 2) | +238 ± 12 (n = 2) | +39 ± 6 (n = 2) | +26 ± 2 (n = 2) | +115 ± 4 (n = 2) | −36 ± 0 (n = 2) | −33 ± 7 (n = 2) | +36 ± 11 (n = 2) |
| EM-8420 | +85 ± 3 (n = 2) | +112 ± 9 (n = 2) | +489 ± 203 (n = 2) | +31 ± 1 | +30 ± 2 | +116 ± 11 | −34 ± 12 | −39 ± 11 | +27 ± 11 |
| EM-5728 | +90 ± 9 (n = 2) | +73 ± 3 (n = 2) | +227 ± 16 (n = 2) | +28 ± 1 (n = 2) | +15 ± 5 (n = 2) | +131 ± 32 (n = 2) | [−37 ± 1] (n = 2) | [−40 ± 1] (n = 2) | ND |
| EM-6595 | +67 ± 10 (n = 2) | +40 ± 3 (n = 2) | +162 ± 9 (n = 2) | +28 ± 3 | +14 ± 1 | +97 ± 9 | [−56 ± 5] | [−74 ± 3] | ND |
| EM-6594 | ND | ND | ND | +28 ± 7 | +13 ± 2 | +97 ± 19 | [−56 ± 4] | [−69 ± 4] | ND |
| EM-9017 | +47 ± 5 | +57 ± 6 | +154 ± 13 | +24 ± 5 | +22 ± 2 | +102 ± 12 | −42 ± 2 | −54 ± 2 | +3 ± 11 |
| EM-9016 | +53 ± 6 | +44 ± 6 | +108 ± 21 | +13 ± 2 | +17 ± 1 | +66 ± 25 | −44 ± 3 | −39 ± 5 | +10 ± 9 |
| EM-6583 | +90 ± 2 | +71 ± 16 | +145 ± 46 | +37 ± 7 | +17 ± 3 | +93 ± 15 | −46 ± 6 | −75 ± 5 | ND |
| EM-6582 | +72 ± 6 | +49 ± 5 | +197 ± 29 | +37 ± 3 | +18 ± 3 | +71 ± 15 | −60 ± 6 | −60 ± 6 | ND |
| EM-8987 | +84 ± 4 | +110 ± 13 | +292 ± 30 | +56 ± 11 | +25 ± 5 | +118 ± 10 | −32 ± 1 [−41 ± 8] | 47 ± 3 [−28 ± 7] | +43 ± 19 [+111 ± 35] |
| EM-8986 | +76 ± 11 | +98 ± 7 | +241 ± 27 | +35 ± 3 | +24 ± 3 | +149 ± 13 | −24 ± 3 | −25 ± 4 | +74 ± 13 |
| EM-3585 | +82 ± 17 | +114 ± 23 | +263 ± 64 | +20 ± 4 (n = 2) | +13 ± 4 (n = 2) | +74 ± 18 (n = 2) | [−26 ± 7] (n = 2) | [−2 ± 15] (n = 2) | [+67 ± 21] |

ND: Not Done

Legend of the table 5:
In Column 1, the laboratory names of the SARMs are reported.
Column 2 represents the change of the prostate of intact rat expressed in percentage of change calculated by the following formula:

% change=[W(compound)−W(control CX)/W(control intact)−W(control CX)]×100.

W is the weight of the prostate.
Column 3 represents the change of seminal vesicle of intact rat expressed in percentage of change calculated by the following formula:

% change=[W(compound)−W(control CX)/W(control intact)−W(control CX)]×100.

W is the weight of the seminal vesicle.

Column 7 represents the agonist effect on bulbocavernosus muscles in castrated rat expressed in percentage of change calculated by the following formula:

% change=[W(compound)−W(control CX)/W(control DHT)−W(control CX)]×100.

W is the weight of the seminal vesicles.
Column 8 represents the antiandrogenic effect on prostate in castrated rat, expressed in percentage of change (% change) calculated by the following formula:

% change=−100−[[W(compound)−W(control CX)/W (control DHT)−W(control CX)]×100].

W is the weight of the prostate.

Column 9 represents the antiandrogenic effect on seminal vesicles in castrated rat, expressed in percentage of change (% change) calculated by the following formula:

% change=−100−[[W(compound)−W(control CX)/W(control DHT)−W(control CX)]×100].

W is the weight of the seminal vesicles.

Column 10 represents the antiandrogenic effect on bulbocavernosus muscles in castrated rat, expressed in percentage of change (% change) calculated by the following formula:

% change=−100−[[W(compound)−W(control CX)/W(control DHT)−W(control CX)]×100].

W is the weight of the bulbocavernosus muscles.

The molecular structure of antiandrogens whose efficacy is reported in Tables 1, 2 and 3 is set forth below:

EM-5854

EM-5987

EM-5985

EM-5855

EM-8454

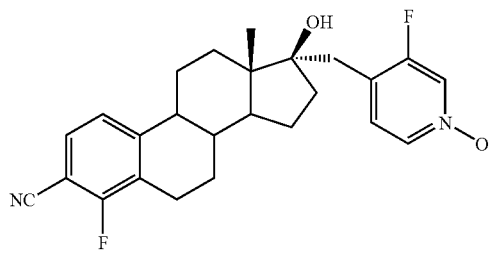

EM-8505

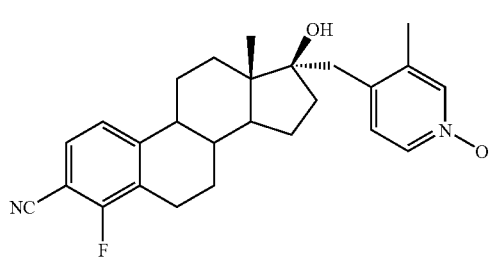

EM-8455

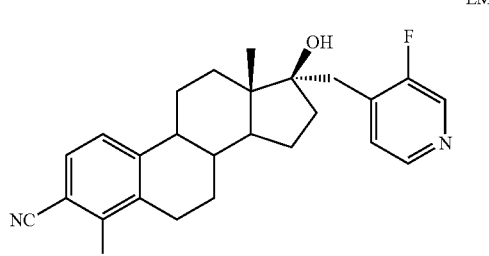

EM-8504

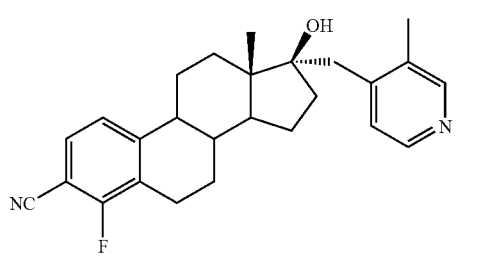

EM-8632

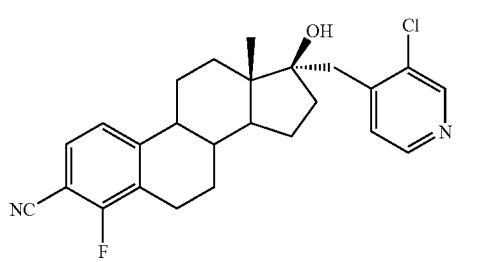

EM-4350

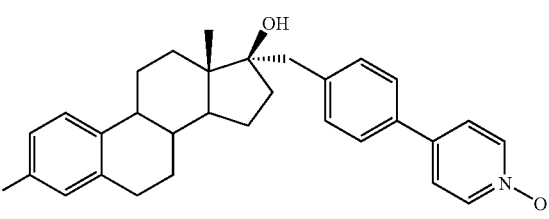

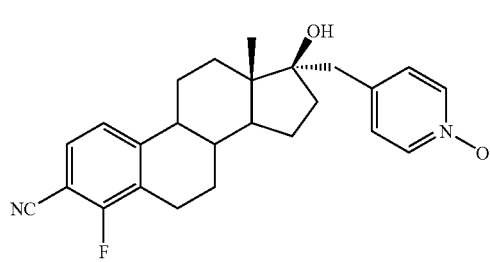

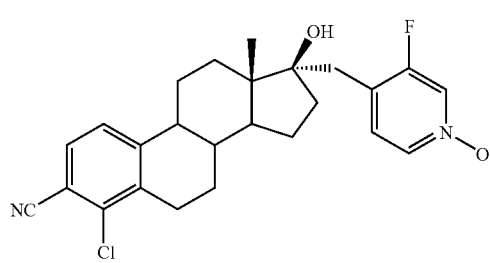

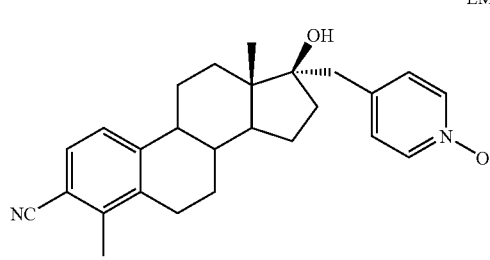

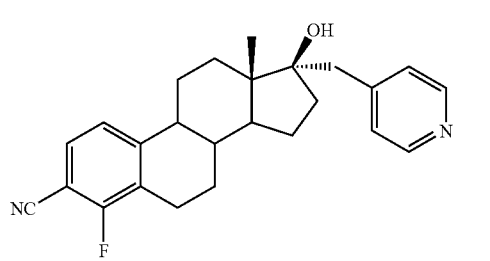

EM-5988
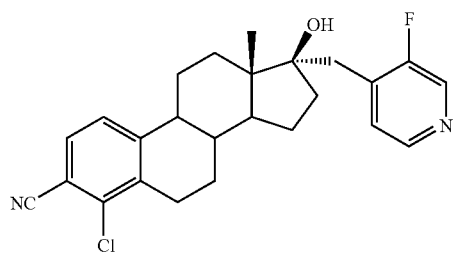
EM-5984
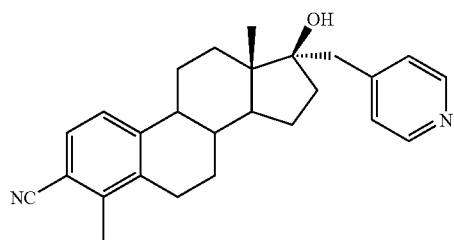
EM-8633
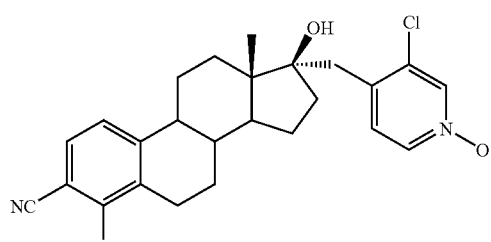
EM-4240
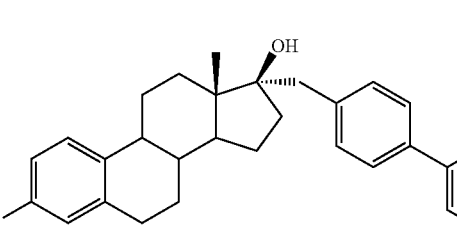
EM-5945
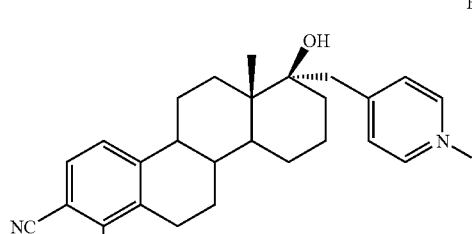
EM-5943
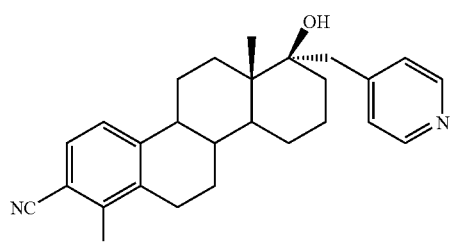
EM-9140
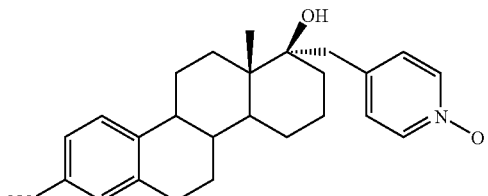
EM-9139
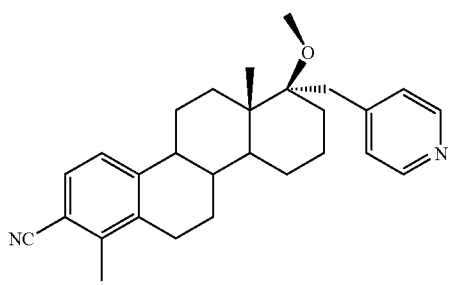
The molecular structure of SARMs whose efficacy is reported in Tables 4 and 5 is set forth below:
EM-8419
EM-8420
EM-5728

EM-6595
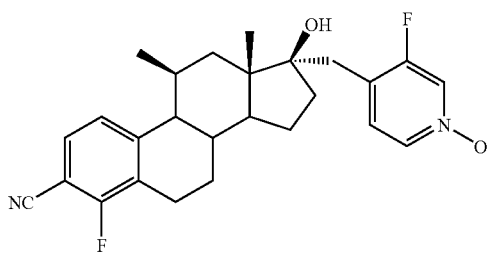

EM-6594
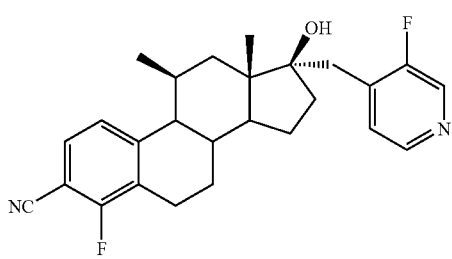

EM-9017
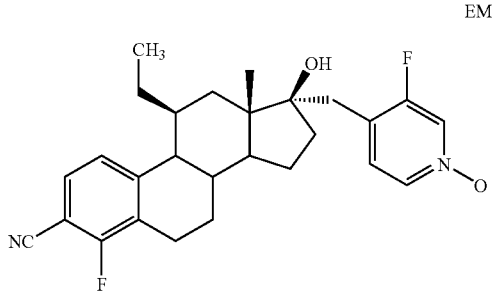

EM-9016
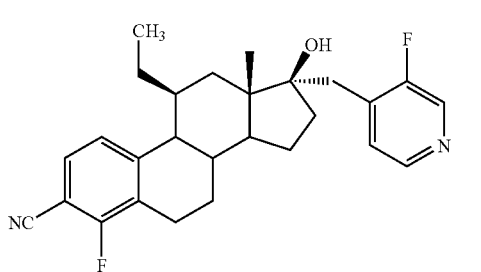

EM-6583
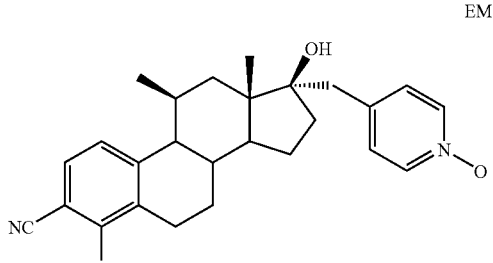

EM-6582

EM-8986
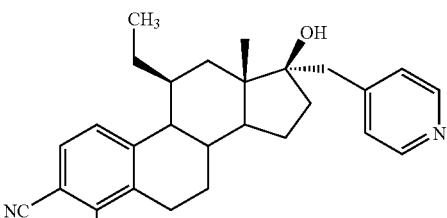

EM-8987
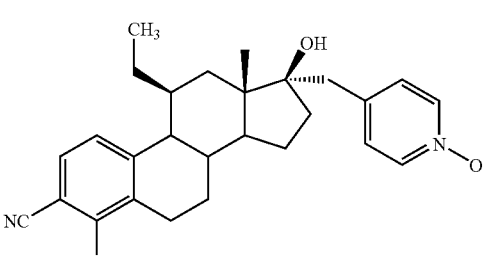

EM-3585
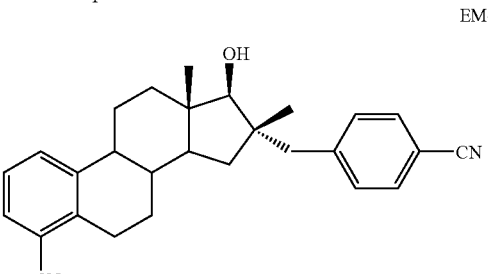

Efficacy of the Preferred Inhibitors

1) Materials and Methods
A—Androgen Receptor (AR) Assay
AR Transfection
Preparation of Human Embryonic Kidney (HEK-293) Cells Transfected with the Human Androgen Receptor (hAR):

Cells are cultured in 6-well Falcon flasks to approximately $3 \times 10^5$ cells/well in Dulbecco's modified Eagle's medium (DMEM) supplemented with 10% calf fetal serum at 37° C. under a 95% air, 5% $CO_2$ humidified atmosphere. Five µg of pCMVneo-hAR plasmid are transfected using the lipofectin transfection kit (Life Technologies, Ontario, Canada). After 6 h of incubation at 37° C., the transfection medium is removed and 2 ml of DMEM are added. Cells are further cultured for 48 h and then transferred into 10 cm petri dishes and cultured in DMEM containing 700 µg/ml of G-418 in order to inhibit the growth of non-transfected cells. Medium containing G-418 is changed every two days until resistant colonies are observed. Positive clones are selected by PCR. HEK 293 cells transfected with hAR are frozen until being used for the binding assay.

HEK-293 hAR Cell Cytosol Preparation:
On the morning of the binding assay, a pellet of HEK-293 hAR cells is thawed and suspended in buffer A (25 mM Tris-HCl, 1.5 mM EDTA disodium salt, 10 mM α-monothioglycerol, 10% glycerol, and 10 mM sodium molybdate, pH 7.4; 625 000 cells/0.1 ml). The cell suspension is sonicated for three periods of 30 sec (with intervals for cooling) and then centrifuged at 105 000×g for 90 min.

Rat Prostate Cytosol Preparation:

On the morning of the binding assay, ventral prostates collected from 24 h-gonadectomized rats were homogenized in buffer A (1 g of tissue in 5 mL) and the homogenate was centrifuged as described above.

Androgen Receptor Assay

Androgen binding is measured using the hydroxylapatite (HAP) assay. In brief, the radioactive steroid [$^3$H]R1881 solubilized in ethanol is diluted with buffer B (10 mM Tris-HCl, 1.5 mM EDTA disodium salt, 10 mM α-monothioglycerol, pH 7.4). Aliquots of the cell or prostate cytosol preparation (0.1 ml) are then incubated with 5 nM [$^3$H]R1881 (0.1 ml, ~100 000 cpm) in the presence or absence of the indicated concentrations of unlabeled compounds (0.1 ml, prepared in buffer B containing 30% ethanol) for 16-18 h at 0-4° C. Triamcinolone acetonide (TAC; 100 nM) is added to mask progesterone receptors. Unbound steroids are separated by incubation for 40 min at 0-4° C. with 0.3 ml HAP prepared in buffer P (50 mM Tris-HCl, 10 mM KH$_2$PO$_4$, pH 7.4). After incubation with HAP and 10 min of centrifugation at 1000×g, the pellet is washed 3 times with 1 ml of buffer P. Thereafter, the radioactivity is extracted from the pellet by incubation at room temperature for 60 min with 1 ml of ethanol. After centrifugation, the supernatant is decanted into a scintillation vial and the pellet is extracted again with ethanol. After the addition of scintillation liquid, the radioactivity is measured in a liquid scintillation counter.

Calculations

Dose-response curves as well as IC$_{50}$ values of the tested compounds (concentration of the compound causing a 50% displacing of [$^3$H](R1881) were calculated using a weighted iterative nonlinear least-square regression.

Relative binding affinity (RBA) was calculated by the following formula:

RBA (%) [IC$_{50}$(R1881)/IC$_{50}$(compound)]×100

B—In vitro Assay of Androgenic/Antiandrogenic Activity

The in vitro androgenic/antiandrogenic activity was measured using Shionogi mouse mammary carcinoma cells (clone 107) (Labrie and Veilleux, 1988; Labrie et al., 1988a; Labrie et al., 1988b).

Materials

Minimal essential culture medium (MEM) and non-essential amino acids were purchased from Gibco BRL (NY, USA) while charcoal-stripped fetal calf serum (FBS) was purchased from Wisent Inc. (Montreal, Canada). Dihydrotestosterone (DHT) was obtained from Steraloids (Wilton, N.H.) while the compounds to be tested were synthesized in our laboratory.

Maintenance of Stock Cell Cultures

Shionogi cells were routinely grown in MEM supplemented with 100 nM DHT, 5% (v/v) charcoal-stripped FBS, 100 IU penicillin/ml, 50 µg streptomycin sulfate/ml, and 1% (v/v) non-essential amino acids, as previously described (Labrie and Veilleux, 1988; Labrie et al., 1988a; Labrie et al., 1988b). Cells were incubated at 37° C. in a humidified atmosphere of 5% CO$_2$ and 95% air. Cells were subcultured at near-confluence by gentle digestion in a solution of 0.1% trypsin (Wisent Inc.) in Hepes buffer containing 3 mM ethylenediaminetetraacetic acid (EDTA) (pH 7.2). Cells were then pelleted by centrifugation, resuspended in culture medium, and replated.

Measurement of Cell Proliferation

Cells were plated in 24-well plates at a density of 18 000 cells/well and allowed to adhere to the surface of the plates for 24 h. Thereafter, medium was replaced with fresh medium containing 2% (v/v) charcoal-stripped FBS and the indicated concentrations of compounds diluted from stock solutions at a ×1000 concentration in 99% redistilled ethanol in the presence or absence of DHT (0.3 nM). Control cells received only the ethanolic vehicle (0.1% EtOH, v/v). Such a concentration of ethanol does not affect cell growth. The indicated increasing concentrations of agents were added to triplicate dishes, and cells were grown for 10 days with changes of medium every 2-3 days. Cell number was determined by measurement of DNA content as previously described (Simard et al., 1990).

Calculations

Dose-response curves as well as IC$_{50}$ values of the tested compounds are calculated using a weighted iterative nonlinear least-squares regression. All results are expressed as means±SEM, except when SEM overlaps with the symbol used in which instances only the symbol is illustrated. The apparent inhibition Ki values were calculated according to the following equation: Ki=IC$_{50}$/(1+S/K). In this equation, S represents the concentration of DHT (0.3 nM), K is the apparent KD of DHT action on cell proliferation in Shionogi cells (0.1 nM) and IC$_{50}$ is the concentration of the compound giving a 50% inhibition of DHT action on cell growth.

C—Determination of Oral Absorption of Compounds

Animals

Castrated male Sprague-Dawley rats (Crl:CD(SD)Br) weighing 275-375 g were used for pharmacokinetic studies. Animals were fasted (access to water only) from around 16 h00 the afternoon prior to the dosing day.

Dosing and Blood Collection

Tested compounds were administered orally by gavage (in the morning) at a dose of 0.5 mg/animal (1.0 ml/animal; 3 animals/compound). Compounds were dissolved in dimethylsulfoxide (DMSO, 10% final concentration) and administered as a solution/suspension in 0.9% NaCl-1% gelatin. Blood samples (~0.5 mL/timepoint) were collected by jugular venipuncture on animals under isoflurane anesthesia at 1, 2, 3, 4, 7 and 24 h post-dosing. Blood samples were put into tubes containing EDTA(K$_3$) as anticoagulant and centrifuged at 4° C. for 10 min at 1700-2400 g. The resulting plasma is frozen on dry ice and kept at −80° C. pending analysis. After the blood collection 7 h post-dosing, the ventral prostate was collected from one rat per group for determination of the intraprostatic concentration of the tested compound.

Plasma Analyses

Plasma concentrations of the tested compounds and/or metabolite(s) were determined using liquid chromatography with mass spectrometric detection assay (LC-MS/MS). The plasma concentration of each compound versus time was used to calculate the area under the plasma concentration curve from 0 to 24 hr post-dose [AUC$_{(0-24h)}$]. AUC$_{(0-24hr)}$ values were calculated using the linear trapezoidal method. Intraprostatic concentrations of the compounds were determined by LC-MS/MS.

D—Systemic Antiandrogenic/Androgenic Activity in Orchidectomized Immature Male Rats Animals Immature male rats (Crl:CD(SD)Br) 22 to 24-day old were obtained from Charles-River, Inc. (St-Constant, Quebec, Canada) and housed up to 5 per cage in plastic bins in a temperature (23±1° C.)—and light (12 h light/day, lights on at 7 h15)—controlled environment. The rats were fed rodent chow and tap water ad libitum. Compounds were tested in castrated rats supplemented (antagonistic activity) or not (agonistic activity) with an androgen. The day following their arrival, the designed animals were orchidectomized (CX) under Isoflurane anesthesia (Study Day 1) via the scrotal route and were then randomly assigned to groups of 3 to 5 animals. At the time of orchidectomy, one silastic implant of dihydrotestosterone (DHT; 1 cm length of pure DHT in silastic tubing having inner and outer diameter of 0.078 and 0.125 inches, respectively), was inserted subcutaneously in the dorsal area of animals assigned to the evaluation of antiandrogenic activity.

Treatments

Tested compounds were administered orally once daily for 7 days from Study Day 2 to Study Day 8 at doses ranging from 0.1 and 0.5 mg/animal. Compounds were solubilized in dimethylsulfoxide (DMSO, 10% final concentration) and administered as a solution/suspension in 0.9% NaCl-1% gelatin. Animals of the control groups received the vehicle alone during the 7-day period. Some animals were treated with the antiandrogen Flutamide or Casodex as reference. The animals under isoflurane anesthesia were killed by cervical dislocation on day 9 of the study, approximately 24 h after the last dosing. The ventral prostate and seminal vesicles were rapidly dissected and weighed.

E—Systemic Antiandrogenic Activity in Mature Male Rats

Animals

Mature male rats (Crl:CD(SD)Br) weighing 250-275 g were obtained from Charles-River, Inc. (St-Constant, Quebec, Canada) and housed up to 3 per cage as described above. The day following their arrival, the animals were orchidectomized (CX) under Isoflurane anesthesia (Study Day 1) via the scrotal route and were randomly assigned to groups of 5 animals. At the time of orchidectomy, two silastic implants of androstenedione (4-dione; length of pure 4-dione in implant: 1.5 cm, tubing inner and outer diameters: 0.062 and 0.125 inches) was inserted subcutaneously in the dorsal area of animals.

Treatment

The compound EM-5854 was administered orally once daily for 7 days from Study Day 2 to Study Day 8 at doses of 0.2 and 1 mg/animal while the reference compounds flutamide and bicalutamide (Casodex) were administered orally at doses of 1 and 5 mg/animal during the same period. Compounds were solubilized as described above. The animals under isoflurane anesthesia were killed by cervical dislocation on day 9 of the study, approximately 24 h after the last dosing. The ventral prostate and seminal vesicles were rapidly dissected and weighed.

Calculations

For antagonistic activity, the percentage of change is calculated using the following formula:

% change=−100−[[$W$(compound)−$W$(control $CX$)/$W$ (control $DHT$)−$W$(control $CX$)]×100].

For agonistic activity, the percentage of change is calculated by the following formula:

% change=[$W$(compound)−$W$(control $CX$)/$W$(control $DHT$)−$W$(control $CX$)]×100.

W is the weight of the prostate, seminal vesicles or bulbocavernosus muscles.

Discussion

A series of steroidal possessing a side-chain able to modify the interaction of the steroidal backbone with the Androgen Receptor were synthesized. As seen in tables 1 and 4 and FIGS. 1 to 5, these compounds show affinities for the Human Androgen Receptor with a Relative Binding Affinity (RBA) ranging from the modest value of about 0.3% to a high value of 2250% (for EM-9016) compared to a value of 100% for R1881, a well known synthetic and metabolism-resistant synthetic androgen having an affinity for the human androgen receptor similar to DHT (dihydrotestosterone), the most potent natural androgen.

Antiandrogens of the Invention

All antiandrogens of the invention show a potent and pure antiandrogenic activity in Shionogi mouse mammary carcinoma cells as well as in vivo on prostate and seminal vesicle weight in the rat. These compounds reverse the 0.3 nM DHT-induced cell proliferation with Ki values ranging from 0.35 nM to 24 nM while the Ki of hydroxyflutamide is 16.8±0.5 nM and the Ki of bicalutamide is 48±9 nM. Thus, the Ki values of the steroidal EM-5985 (0.9±0.2) and EM-5854 (2.5±0.4 nM) are respectively 12 and 5.5 times more potent than the Ki of hydroxyflutamide (table 1).

Figure 7:
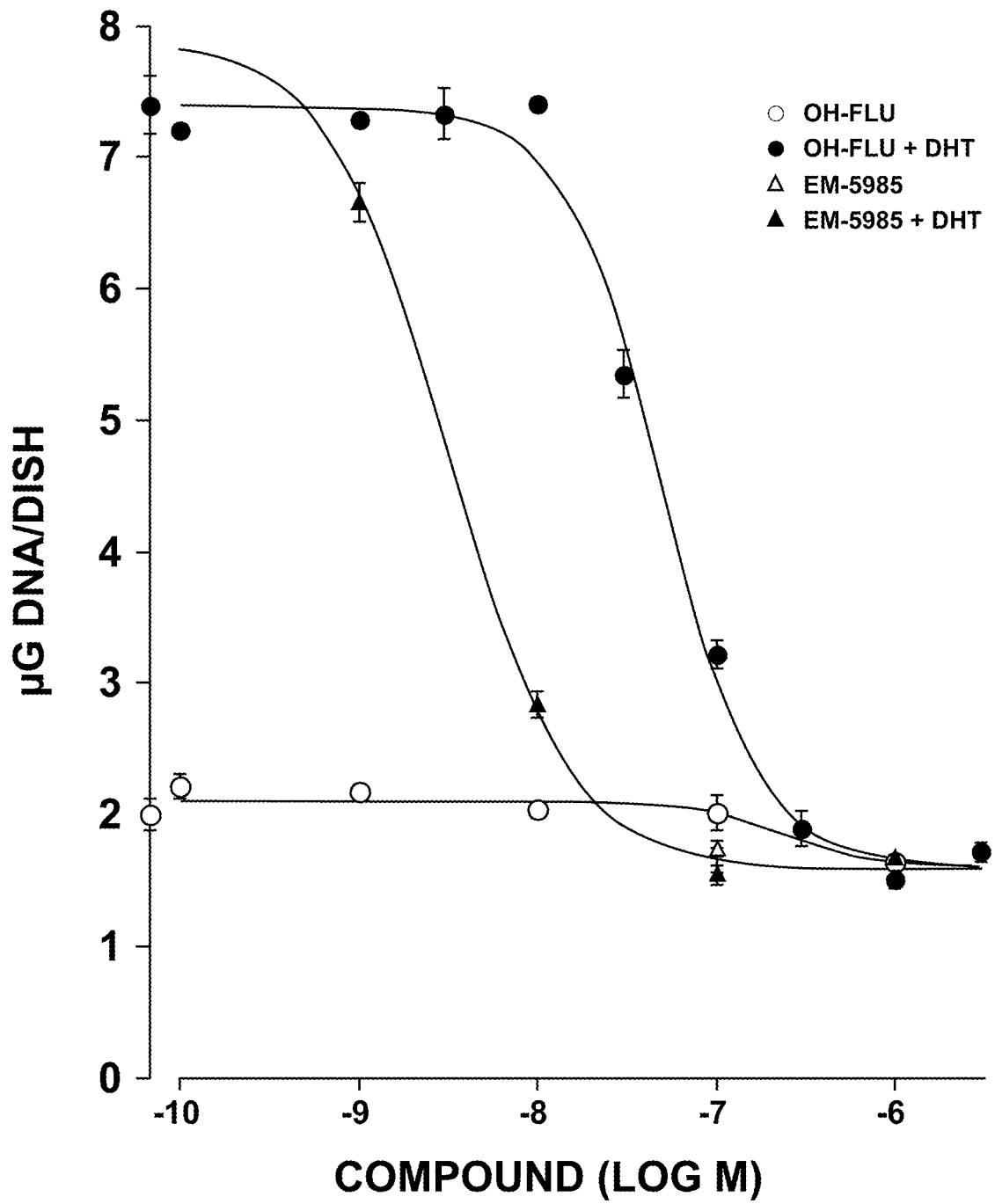
FIG. 7 illustrates the effect of EM-5985 on the proliferation of androgen-sensitive mammary carcinoma Shionogi cells in the presence or absence of DHT. OH-FLU is used as reference.
Figure 8:
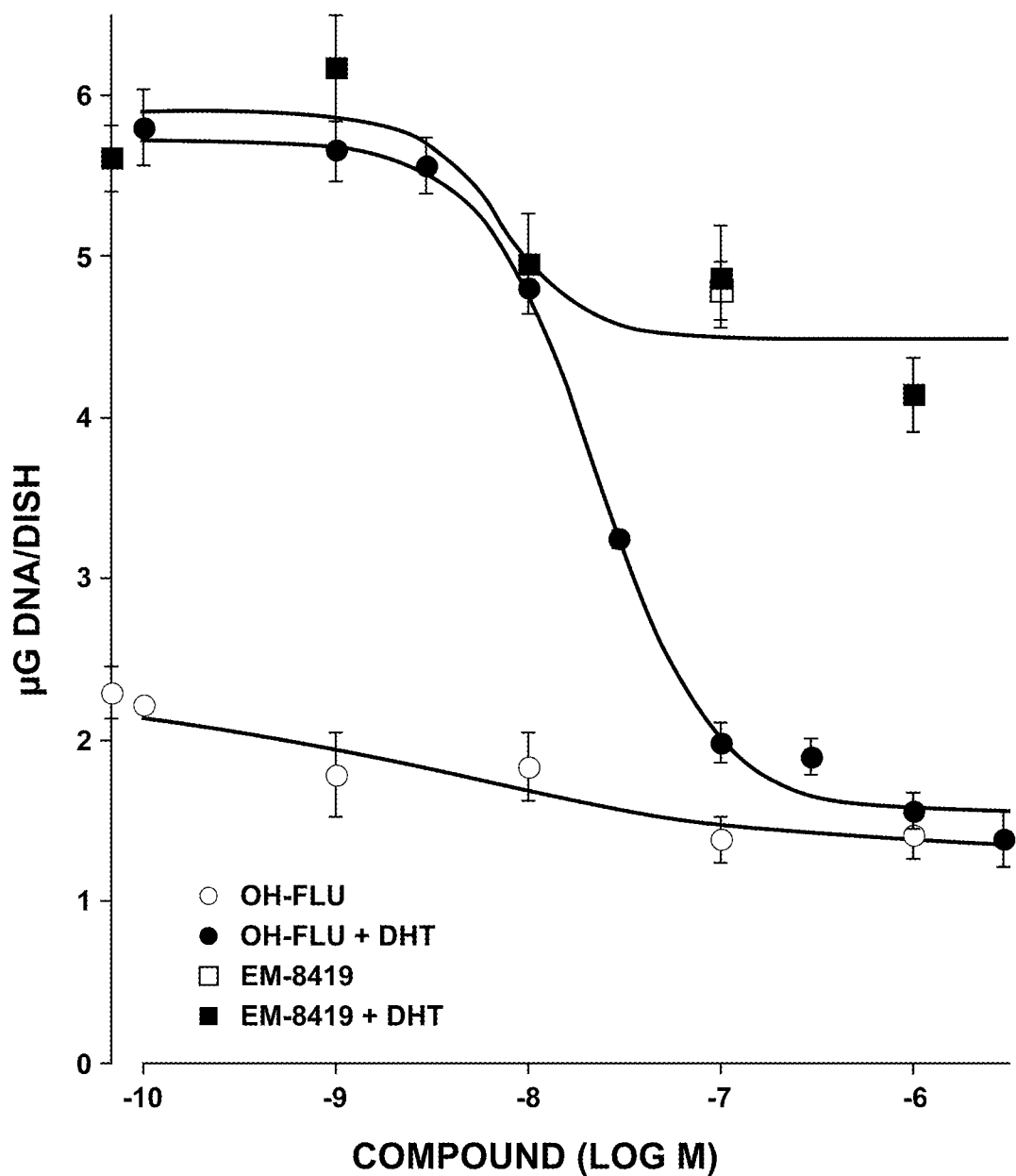
FIG. 8 illustrates the effect of EM-8419 on the proliferation of androgen-sensitive mammary carcinoma Shionogi cells in the presence or absence of DHT. OH-FLU is used as reference.
Figure 9:
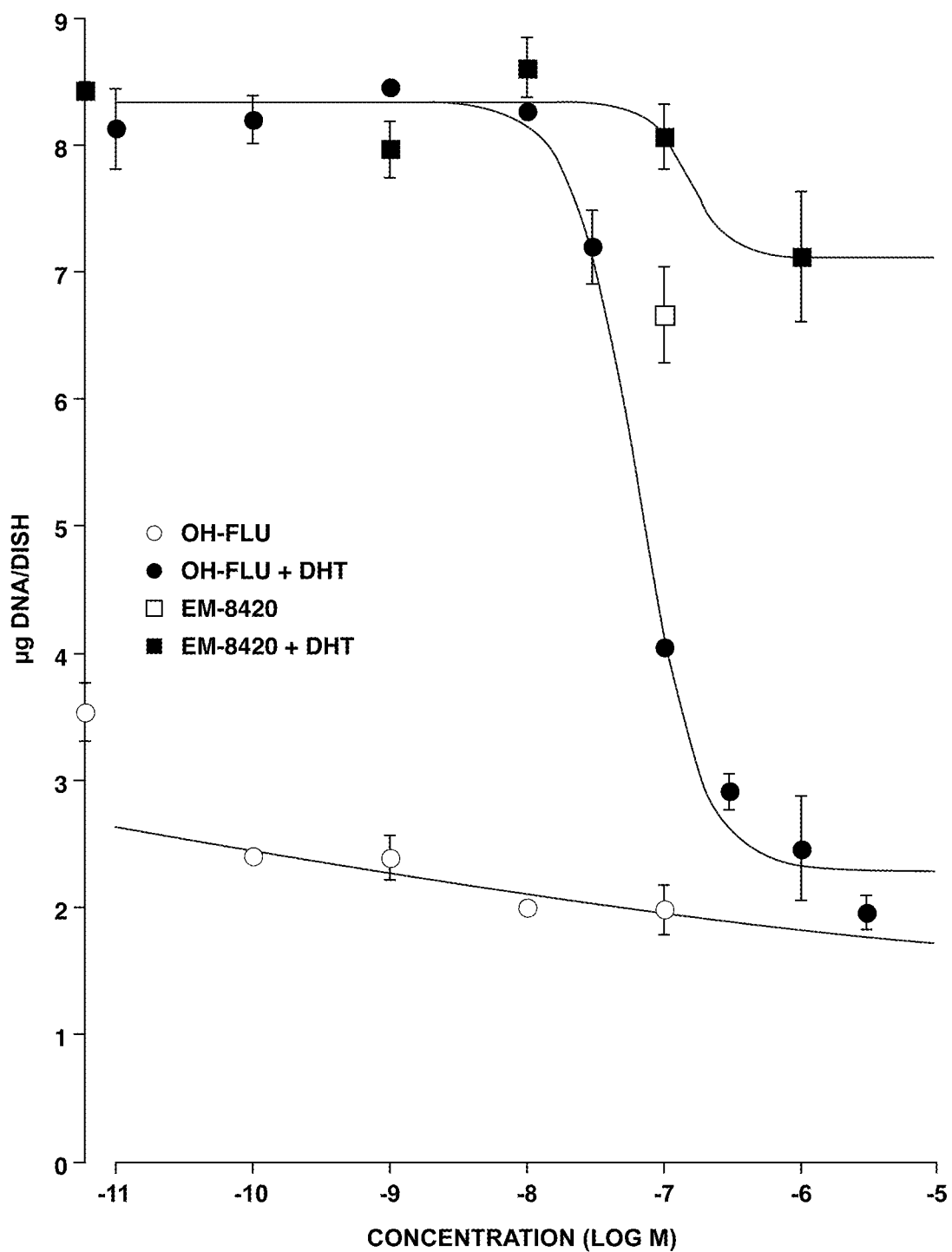
FIG. 9 illustrates the effect of EM-8420 on the proliferation of androgen-sensitive mammary carcinoma Shionogi cells in the presence or absence of DHT. OH-FLU is used as reference.
Figure 10:
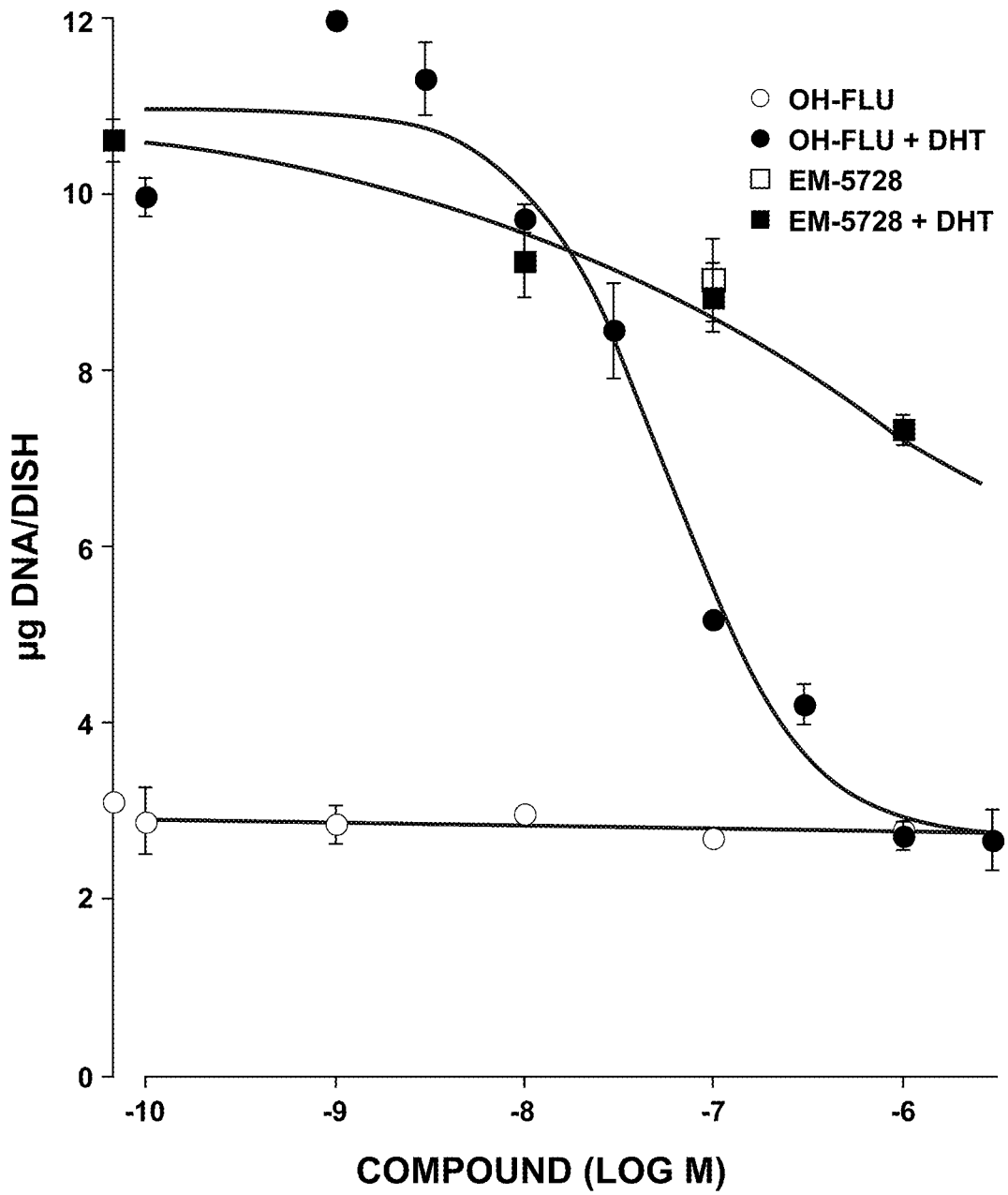
FIG. 10 illustrates the effect of EM-5728 on the proliferation of androgen-sensitive mammary carcinoma Shionogi cells in the presence or absence of DHT. OH-FLU is used as reference.
Figure 11:
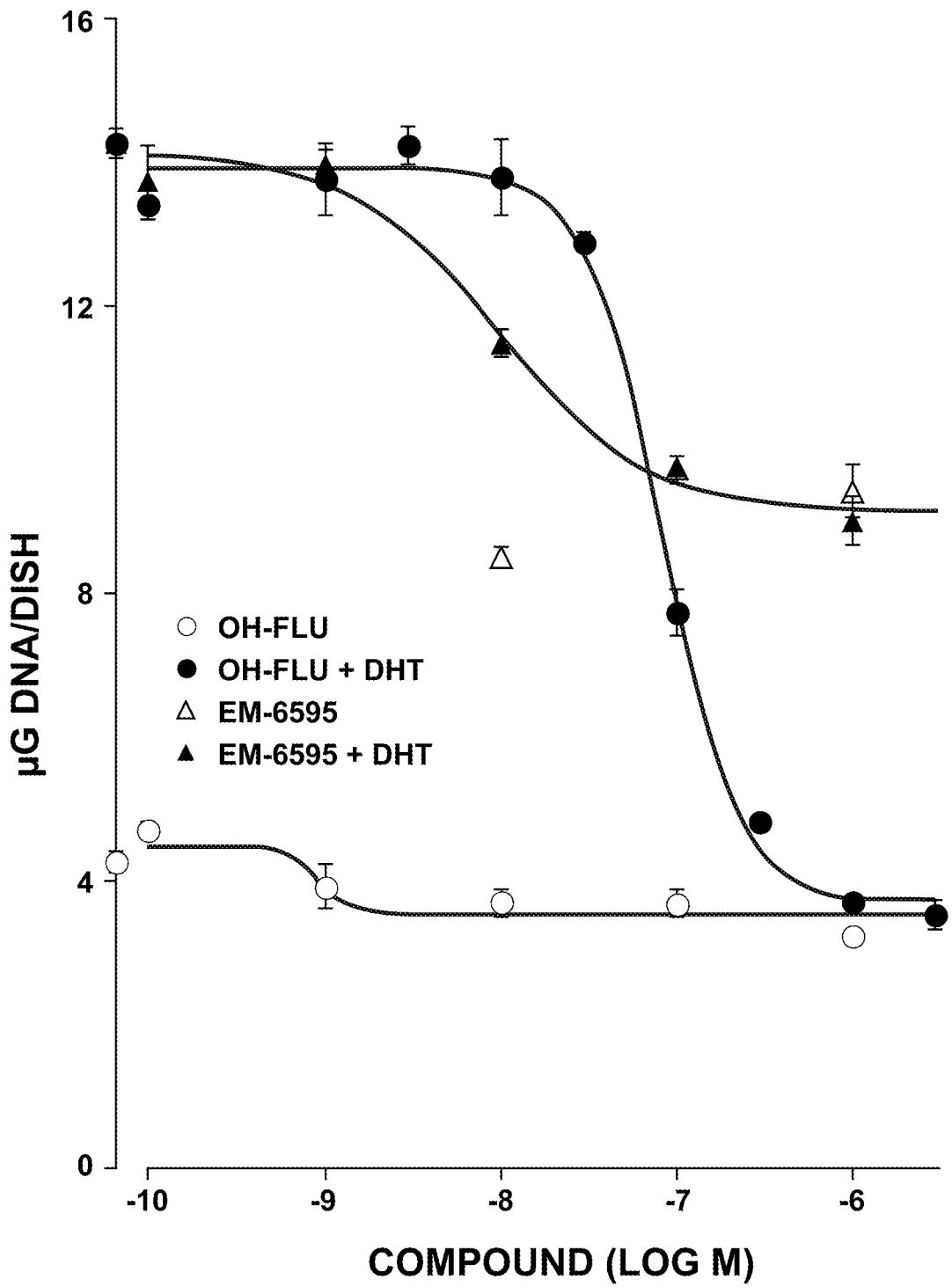
FIG. 11 illustrates the effect of EM-6595 on the proliferation of androgen-sensitive mammary carcinoma Shionogi cells in the presence or absence of DHT. OH-FLU is used as reference.

The most active antiandrogens of the invention on the DHT-induced proliferation of Shionogi cells, namely EM-5943, EM-5987, EM-4350, EM-8633, EM-9139, EM-5945 and EM-5985 (Ki=0.9 nM) are approximately 12 to 29 times more potent than hydroxyflutamide. Most importantly, none of these compounds has any activity on the basal level of Shionogi cell proliferation (EM-5985, FIG. 7), thus indicating their pure antiandrogenic activity.

These compounds show an excellent bioavailability as illustrated by the high AUC (Area Under the Curve) values after oral administration of 0.5 mg per rat. The AUC values of EM-5985, EM-5854 and EM-5945 are 3 709±397 ng·h/mL (7 h), 2 933±233 ng·h/mL (7 h), and 11 377±83 ng·h/mL (24 h), respectively, versus 4 059±259 ng·h/mL (24 h) for hydroxyflutamide when Flutamide is administered (table 2).

Figure 12:
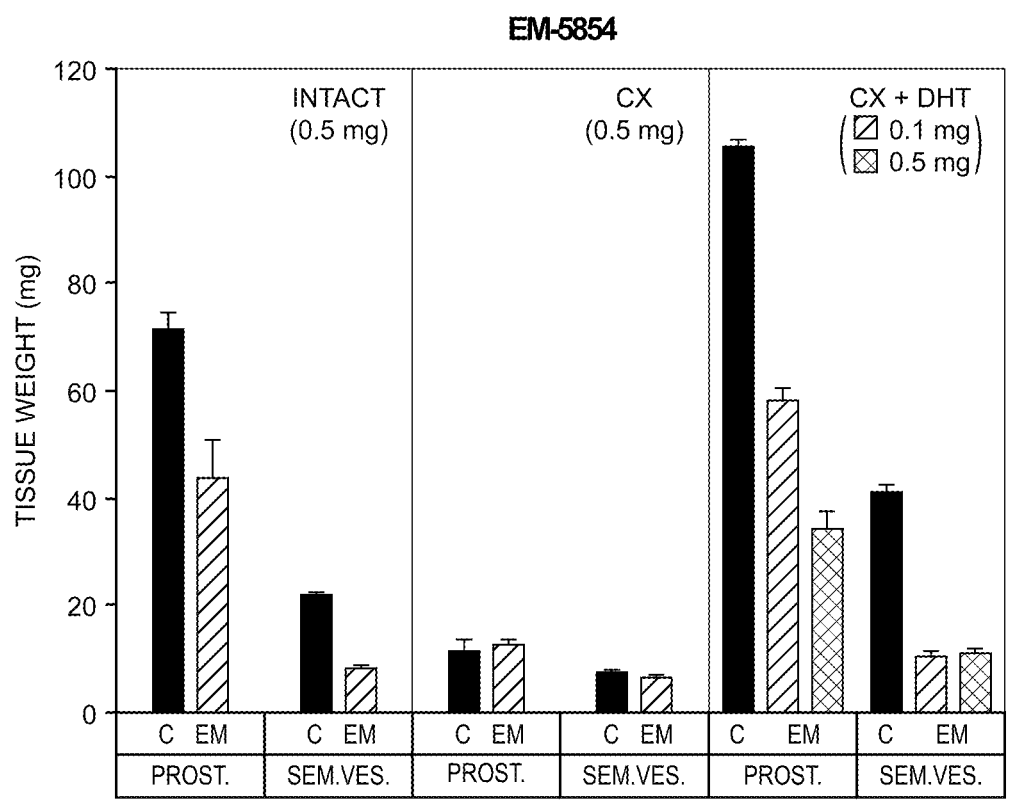
FIG. 12 shows the effect of EM-5854 on the weight of ventral prostate and seminal vesicles following 7-day treatment of immature male rats with these compounds.
Figure 13:
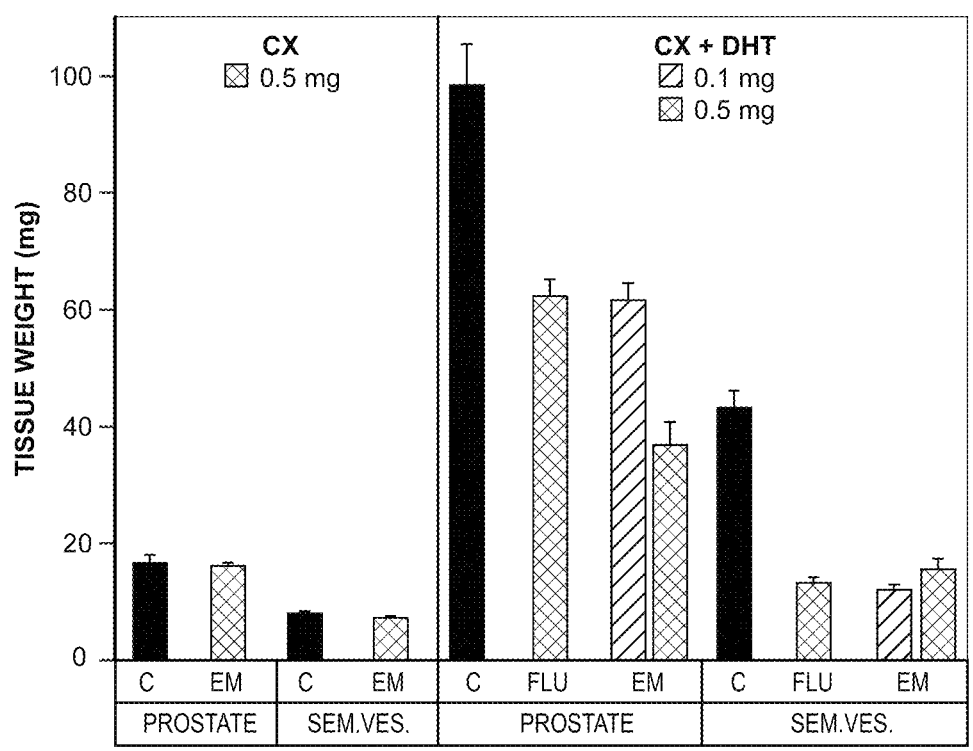
FIG. 13 shows the effect of EM-5985 on the weight of ventral prostate and seminal vesicles following 7-day treatment of immature male rats with these compounds.
Figure 14:
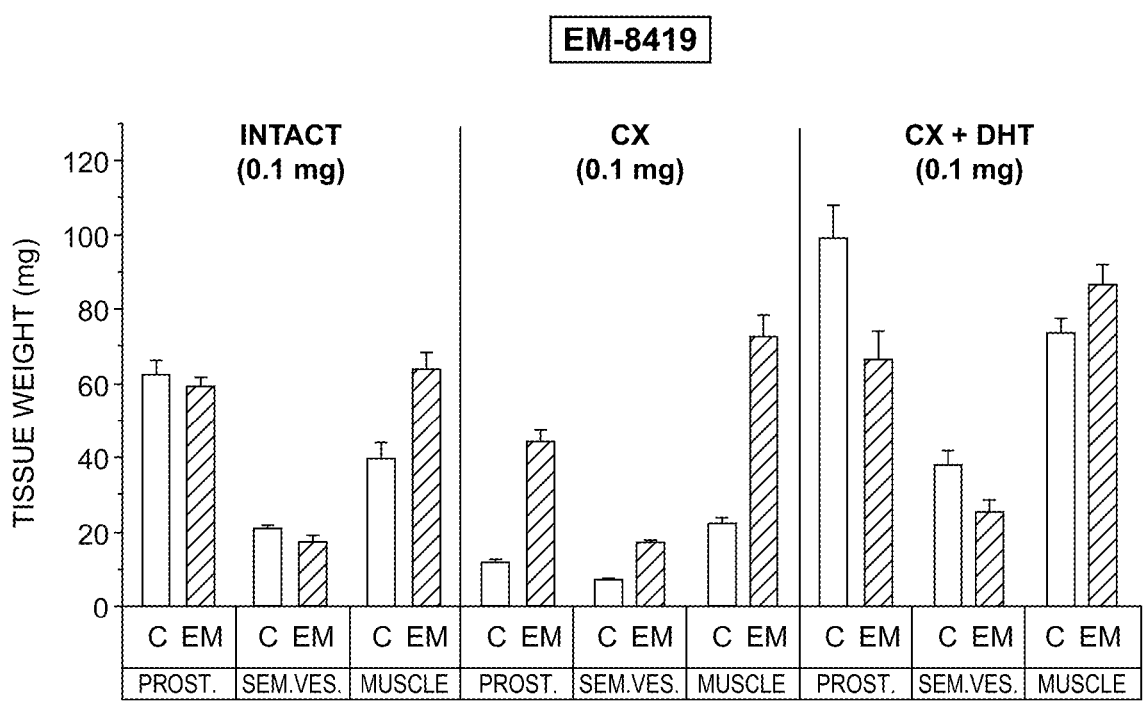
FIG. 14 shows the effect of EM-8419 on the weight of ventral prostate, seminal vesicles and bulbocavernosus muscles following 7-day treatment of immature male rats with these compounds.
Figure 15:
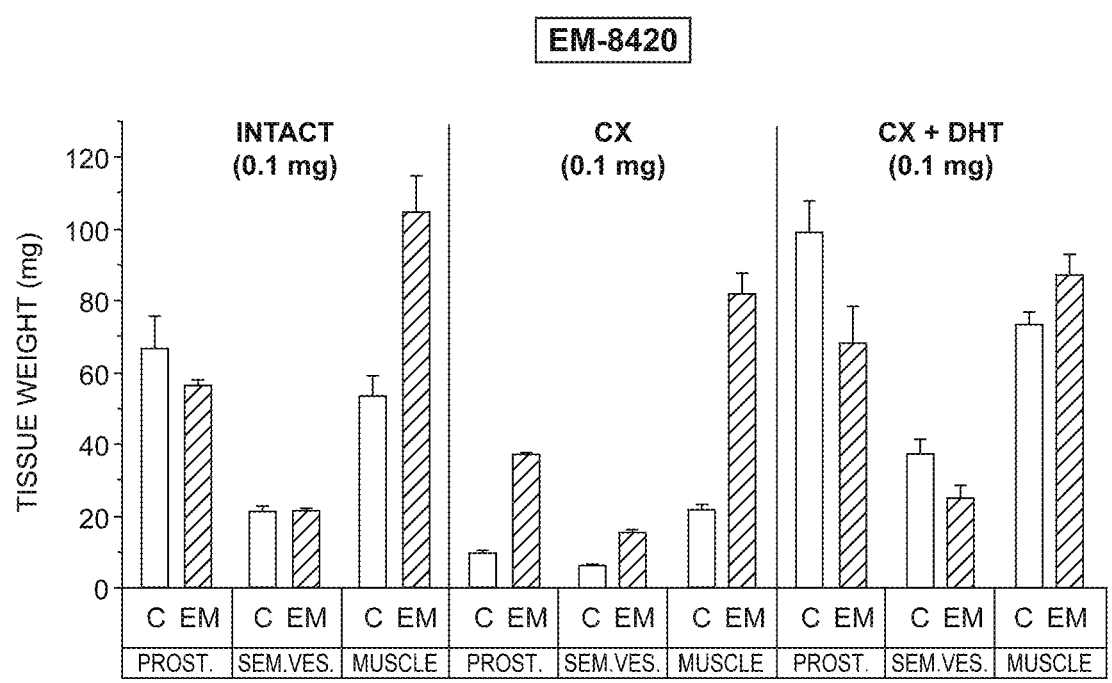
FIG. 15 shows the effect of EM-8420 on the weight of ventral prostate, seminal vesicles and bulbocavernosus muscles following 7-day treatment of immature male rats with these compounds.
Figure 16:
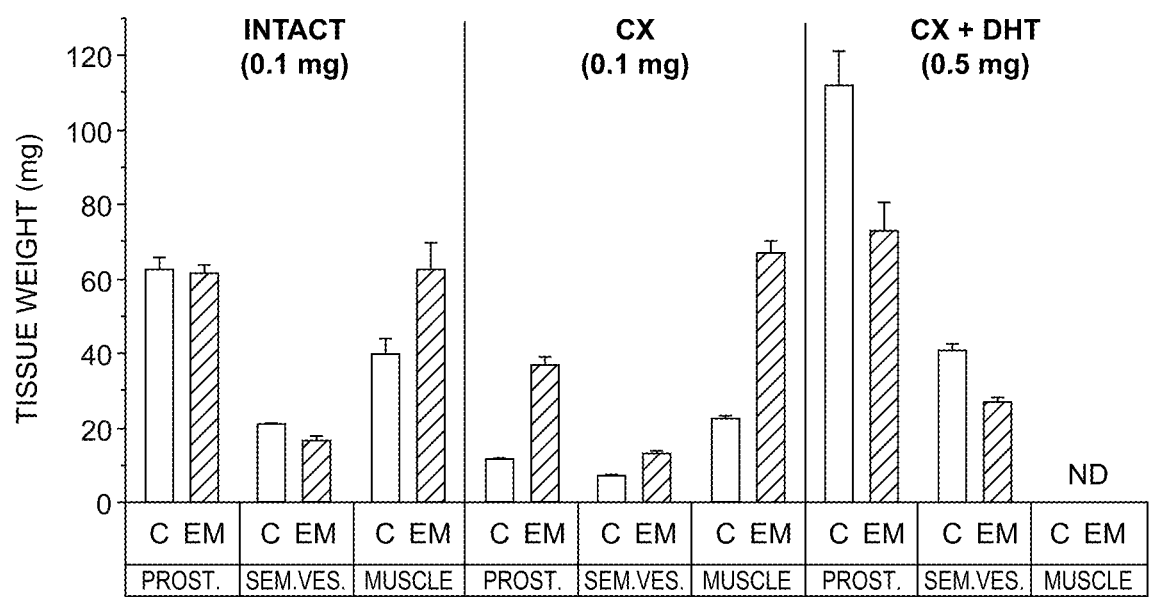
FIG. 16 shows the effect of EM-5728 on the weight of ventral prostate, seminal vesicles and bulbocavernosus muscles following 7-day treatment of immature male rats with these compounds.
Figure 17:
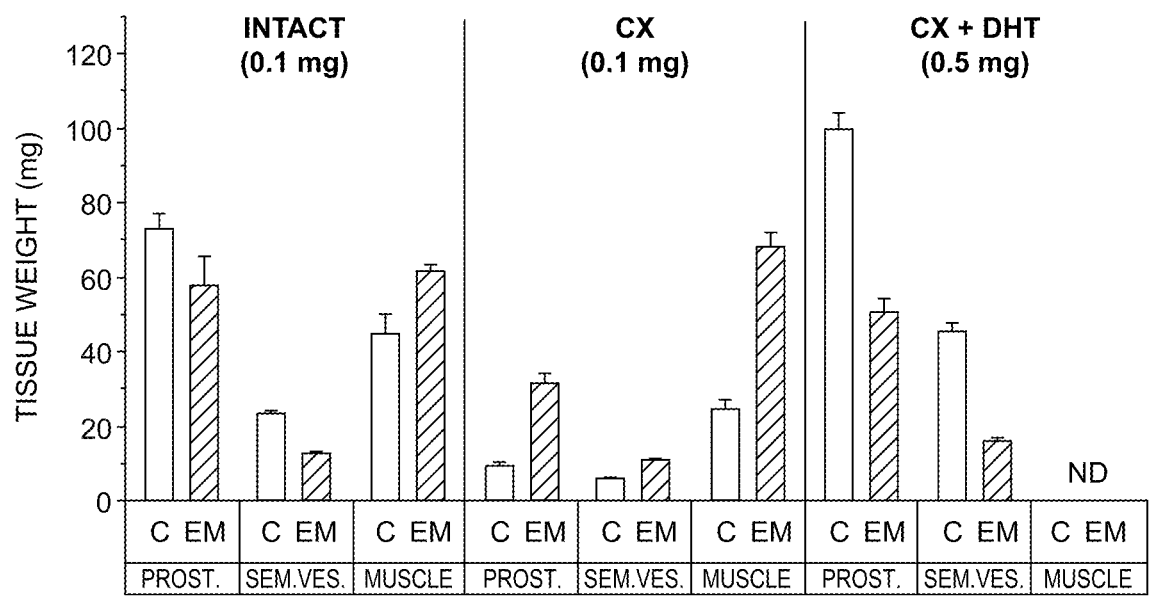
FIG. 17 shows the effect of EM-6595 on the weight of ventral prostate, seminal vesicles and bulbocavernosus muscles following 7-day treatment of immature male rats with these compounds.

The major interest of these compounds is that they show a very potent and pure antiandrogenic activity in vivo in male rats. As seen in table 2, in orchidectomized immature male rats bearing DHT implants, daily oral administration of 0.1 mg/rat of these compounds reversed by 21-53% the stimulatory effect of DHT on ventral prostate and seminal vesicle weight, respectively, while a 5-times higher dose of flutamide (0.5 mg/rat) is required to achieve comparable inhibitions (48% and 83% inhibitions on prostate and seminal vesicle weight, respectively) (FIGS. 12 and 13). At the dose of 0.5 mg/rat, the inhibitions achieved by EM-5985 and EM-5854 are 69% and 76% on ventral prostate, and 84% and 85% on seminal vesicles-DHT stimulated weight, respectively (Table 2; FIGS. 12 and 13). One hundred percent (100%) is the value observed in castrated animals or in the complete absence of androgenic stimulation.

Interestingly, the daily oral administration of these compounds to orchidectomized immature rats has no stimulatory effect on ventral prostate and seminal vesicle weight, thus showing that these compounds exert a pure antiandrogenic activity without any intrinsic androgenic activity (Table 2; FIGS. 12, and 13).

Figure 18:
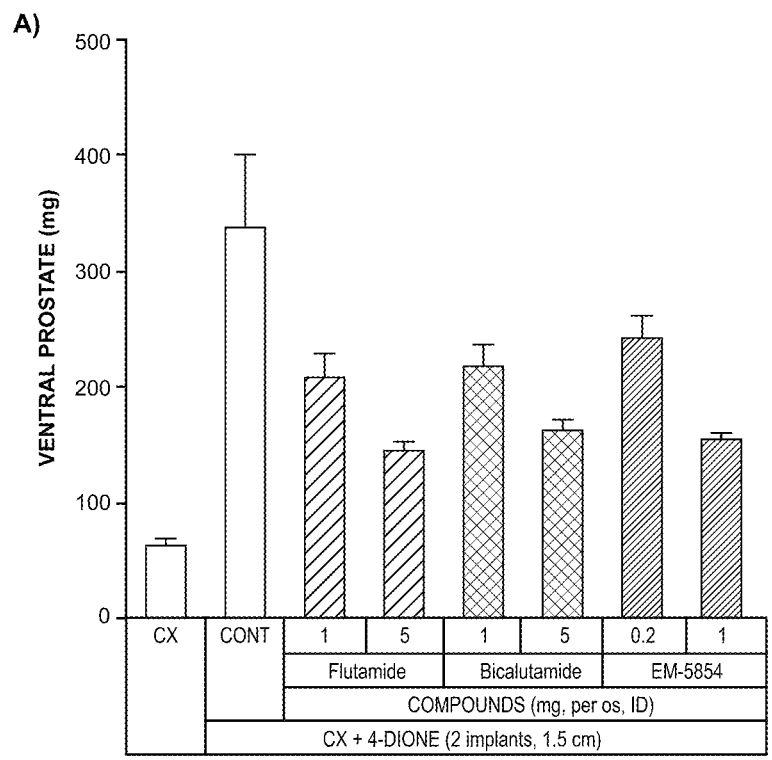
FIG. 18 shows the comparison of In Vivo anti-androgenic activity of EM-5854 with that of Casodex (Bicalutamide) and Euflex (flutamide) in mature male rats.
Figure 18:
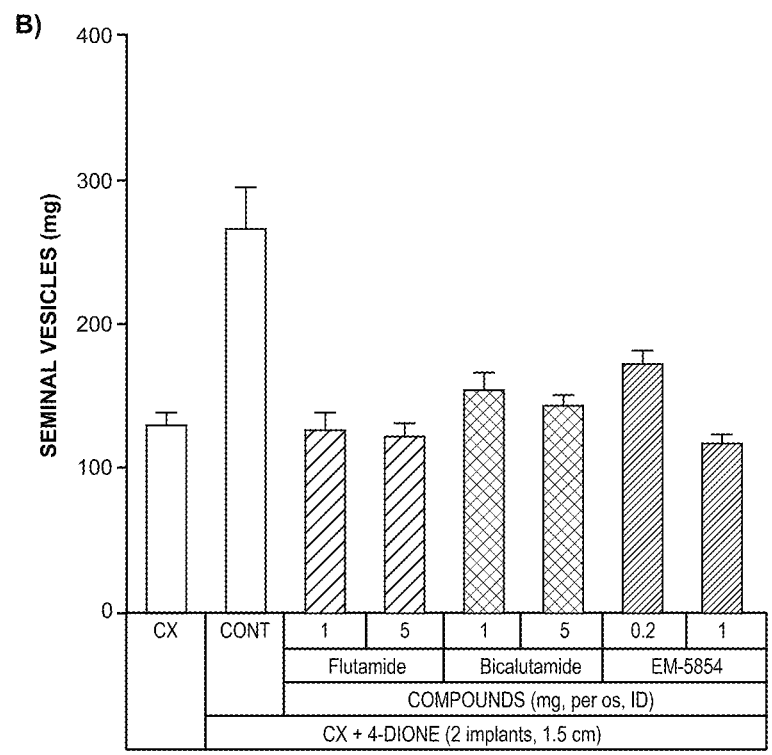

In orchidectomized mature rats supplemented with 4-dione implants, the efficacy of EM-5854 was compared to the two best known antiandrogens, namely flutamide and bicalutamide. At the daily oral dose of 1 mg/rat, EM-5854 reverses by 67% the stimulatory effect of 4-dione on ventral prostate weight while a 5-fold higher dose (5 mg/rat) is required to obtain similar inhibitions of prostate weight by bicalutamide (64%) or flutamide (70%) (Table 3, FIG. 18A). On the other hand, the 4-dione-induced stimulation of seminal vesicle weight is completely reversed by the administration of EM-5854, flutamide or bicalutamide (Table 3, FIG. 18B).

The present data show that the steroidal antiandrogens EM-5985 and EM-5854 and some related compounds are approximately 5 times more potent on rat androgen-sensitive parameters than currently available antiandrogens, thus indicating that these compounds should be developed as systemic antiandrogens for the treatment of androgen-dependant diseases especially as prostate cancer.

Since EM-5985 shows an approximately 3-fold higher affinity for the human compared to the rat androgen receptor and the in vivo potency of these compounds was tested in the rat, we believe that there is a possibility that the 5-fold higher potency of EM-5985 found in the rat will be increased by a factor of 3 in men, thus potentially leading to a 15-fold higher potency than flutamide and bicalutamide in men receiving these drugs for the treatment of prostate cancer.

SARMs of the Invention

As shown in Table 4 and FIGS. 8 to 11, SARMs of the invention have a mixed androgenic/antiandrogenic activity on the proliferation of Shionogi cells. At $10^{-7}$ M, these compounds reversed the DHT-induced cell proliferation by 19% to 64% while, at the same concentration, they stimulated basal cell proliferation from 39% to 79%.

In animal models, the prostate is a well-recognized parameter of androgenic activity, while the androgen-sensitive bulbocavernosus muscles, which are located beside the levator ani muscle (Poortmans and Wyndaele; 1998), are a valuable tool to evaluate anabolic activity. As shown in Table 5 and in FIGS. 14 to 17, SARMs of the invention shown have mixed androgenic/antiandrogenic activity in the immature rat models. In fact, these compounds have a slight to moderate stimulatory effect on the prostate in CX rats while a strong androgenic effect is observed in the muscle. On the other hand, these compounds reverse the DHT-induced stimulation of the prostate but none of these compounds exerts an antiandrogenic activity in the muscle. Moreover, in intact rat model, we observed in some case (i.e. EM-9017) a clear inhibition of the prostate and seminal vesicle but always a stimulation of the muscle. Thus, EM-9017 inhibits intact rat prostate and seminal vesicles of 53±5% and 43±6%, respectively, while stimulates the bulbocavernosus muscles of 54±13%.

With the above-indicated activities, SARMs of the invention are useful in the treatment and prevention of the benign prostatic hyperplasia and in the prevention of the prostate cancer.

EXAMPLES OF SYNTHESIS OF PREFERRED INHIBITORS

Proton NMR spectra were recorded on a Brucker AC-F 300 instrument or a Brucker Avance 400 MHz. The following abbreviations have been used: s, singlet; d, doublet; dd, doublet of doublet; t, triplet; q, quadruplet; and m, multiplet. The chemical shifts (δ) were referenced to chloroform (7.26 ppm for $^1$H and 77.00 ppm for $^{13}$C) or Acetone (2.01 ppm for $^1$H) and were expressed in ppm. Thin-layer chromatography (TLC) was performed on 0.25 mm Kieselgel 60F254 plates (E. Merck, Darmstadt, FRG). For flash chromatography, Merck-Kieselgel 60 (230-400 mesh A.S.T.M.) was used. Unless otherwise noted, starting material and reactant were obtained commercially and were used as such or purified by standard means. All solvents and reactants purified and dried were stored under argon. Anhydrous reactions were performed under an inert atmosphere, the set-up assembled and cooled under argon. Organic solutions were dried over magnesium sulfate, evaporated on a rotatory evaporator and under reduced pressure. Starting materials and reagents were mainly available from Aldrich Chemical Company, Inc. (Milwaukee, Wis.).

Example 1

Synthesis of EM-5854 and Derivatives

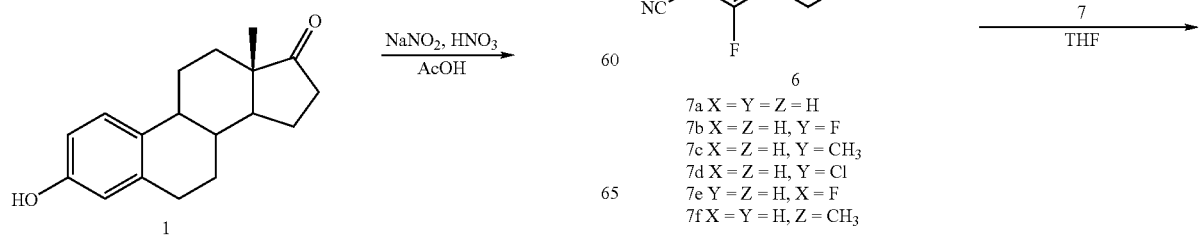

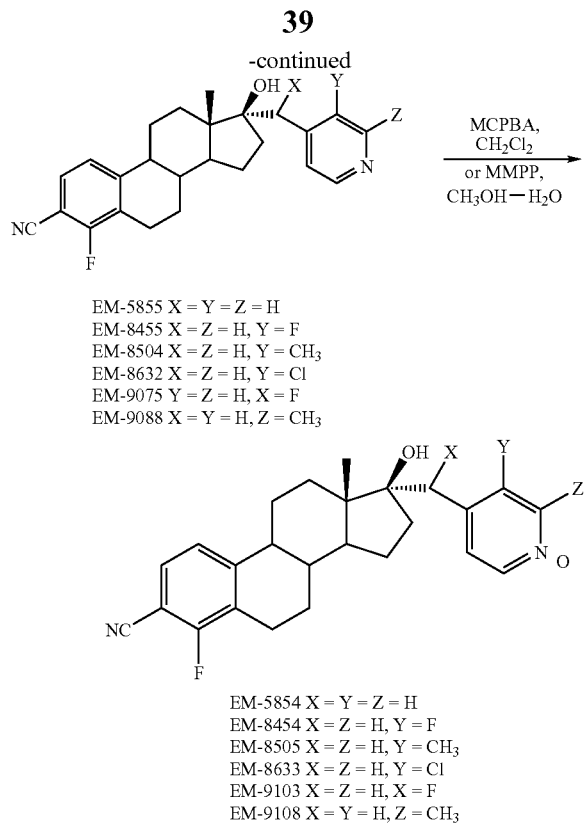

EM-5855 X = Y = Z = H
EM-8455 X = Z = H, Y = F
EM-8504 X = Z = H, Y = CH₃
EM-8632 X = Z = H, Y = Cl
EM-9075 Y = Z = H, X = F
EM-9088 X = Y = H, Z = CH₃

EM-5854 X = Y = Z = H
EM-8454 X = Z = H, Y = F
EM-8505 X = Z = H, Y = CH₃
EM-8633 X = Z = H, Y = Cl
EM-9103 X = Z = H, X = F
EM-9108 X = Y = H, Z = CH₃

Preparation of Compound 2

In a 5 L three-neck round-bottom flask equipped with a mechanical stirrer, a solution of estrone 1 (150 g, 0.556 mol) in 2.2 L of glacial acetic acid was heated at 90° C., in order to dissolve most of the steroid. The mixture was then cooled to 50° C. Meanwhile a mixture of nitric acid (70%, 38 mL), water (100 mL) and few crystals of sodium nitrite was heated at 50° C. for 10 min. The latter was added dropwise to the substrate. The resulting mixture was stirred overnight, then filtrated on a fritted glass funnel to provide 63.0 g (32%) of a pure yellow solid 2. $^1$H NMR (400 MHz, CDCl$_3$) δ: 0.93 (s, 3H, Me), 2.53 (m, 1H, H-16), 3.03 (m, 1H, H-6), 3.23 (m, 1H, H-6), 6.98 (d, J=8.9 Hz, 1H, H-2), 7.48 (d, J=8.9 Hz, 1H, H-1), 9.46 (s, 1H, OH).

Preparation of Compound 3

In a dry 2 L three-neck round-bottom flask equipped with a magnetic stirrer and an addition funnel, under an argon atmosphere, a solution of compound 2 (55.0 g, 0.175 mol), triethylamine (48.6 mL, 0.349 mol) and 4-(dimethylamino) pyridine (2.13 g, 0.017 mol) in 550 mL of anhydrous dichloromethane was stirred at 0° C. Trifluoromethanesulfonic anhydride (35.2 mL, 0.210 mol) was added dropwise, and the mixture was stirred for 30 min at 0° C. An aqueous saturated ammonium chloride solution (250 mL) was added, and the aqueous phase was extracted with dichloromethane (2×100 mL). The combined organic phase was washed successively with a 10% aqueous hydrochloric acid solution (200 mL) and brine (200 mL). The solution was dried over magnesium sulfate and evaporated in vacuo to provide 76.5 g of a brown solid 3 which was used without further purification. $^1$H NMR (400 MHz, CDCl$_3$) δ: 0.93 (s, 3H, Me), 2.54 (m, 1H, H-16), 2.89 (m, 2H, H-6), 7.29 (d, J=8.9 Hz, 1H, H-2), 7.52 (d, J=8.9 Hz, 1H, H-1).

Preparation of Compound 4

In a 2 L round-bottom flask equipped with a magnetic stirrer, under an argon atmosphere, a solution of crude 3 (76.5 g, 0.171 mol), tetrakis(triphenylphosphine)palladium (30.0 g, 0.0260 mol) and zinc cyanide (40.2 g, 0.342 mol) in 1 L of dry dimethylformamide was heated at 120° C. for 1 h. The mixture was then cooled to room temperature and filtered on celite. The filter cake was washed with dichloromethane (3×100 mL). The filtrate was evaporated in vacuo and the residue was triturated with methanol at room temperature for 30 min to provide 30.3 g of pure compound 4. The mother liquors were evaporated in vacuo, dissolved in 50 mL of dichloromethane, and purified by column chromatography on silica gel (dichloromethane to dichloromethane-acetone/19:1) to provide an additional 15.9 g of compound 4 (83% total yield for two steps). $^1$H NMR (400 MHz, CDCl$_3$) δ: 0.93 (s, 3H, Me), 2.54 (m, 1H, H-16), 2.90 (m, 2H, H-6), 7.58 (d, J=8.5 Hz, 1H, Ar), 7.61 (d, J=8.5 Hz, 1H, Ar).

Preparation of Compound 5

In a 5 L three-neck round-bottom flask equipped with a mechanical stirrer, was placed a solution of compound 4 (46.2 g, 0.142 mol) in 500 mL of glacial acetic acid. Iron (19.8 g, 0.355 mol) was added portionwise, and the mixture was vigorously stirred for 2 h at 80° C. Cold water (3 L) was poured in the reaction, and the stirring was maintained for 30 min. The mixture was filtered on fritted glass funnel, washed with water (5×250 mL), and dried in vacuo overnight to provide 40.8 g of light brown powder 5 which was used without further purification. $^1$H NMR (400 MHz, CDCl$_3$) δ: 0.91 (s, 3H, Me), 2.49-2.59 (m, 3H, H-16, H-6), 4.34 (bs, 2H, NH$_2$), 6.78 (d, J=8.3 Hz, 1H, H-1), 7.25 (d, J=8.3 Hz, 1H, H-2).

Preparation of Compound 6

In a 1 L round-bottom flask equipped with a magnetic stirrer, under an argon atmosphere, was dissolved crude compound 5 (10.0 g, 34.0 mmol) in dry dichloromethane (250 mL) at 0° C. Boron trifluoride diethyl etherate (6.5 mL, 51 mmol) was added, then the mixture was stirred 10 min and treated dropwise with a solution of tert-butyl nitrite (4.9 mL, 41 mmol) in dry dichloromethane (30 mL). The reaction was vigorously stirred for 1 h at 0° C. The solution was cooled to −30° C., diluted in dry pentane (250 mL), and stirred for 10 min. The agitation was stopped, allowing the solid to settle, and the solvent was removed mechanically. This operation was repeated once, and the resulting stable diazonium salt was dried in vacuo for 1 h. This solid and heptane (500 mL) were then placed in a 1 L round-bottom flask equipped with a magnetic stirrer, under an argon atmosphere. The heterogeneous mixture was heated at 100° C. for 2 h. The reaction was cooled at room temperature, dissolved in dichloromethane (250 mL), and washed successively with water (200 mL) and brine (200 mL). The solution was dried over magnesium sulfate and evaporated in vacuo to provide 5.2 g (51%) of a beige solid 6. $^1$H NMR (400 MHz, CDCl$_3$) δ: 0.92 (s, 3H, Me), 2.53 (m, 1H, H-16), 2.74 (m, 1H, H-6), 2.99 (m, 1H, H-6), 7.19 (d, J=8.3 Hz, H, H-1), 7.40 (t, J=7.4 Hz, 1H, H-2).

Preparation of EM-5855

To a solution of diisopropylamine (141 µL, 1.0 mmol) in anhydrous THF (1.5 mL) at −78° C. was added dropwise a solution of n-BuLi (2.5 M in hexanes, 0.4 mL, 1.0 mmol). The mixture was stirred for 30 min at −78° C. To this freshly prepared LDA solution (0.5 M) was added dropwise a solution of 4-picoline 7a (97 µL, 1.0 mmol) in THF (2 mL). The mixture was stirred at −78° C. After 1 h, a solution of compound 6 (100 mg, 0.33 mmol) in THF (3 mL) was added and the mixture was stirred for 1 h at −78° C. After completion of the reaction (TLC), the reaction was quenched by addition of aqueous saturated ammonium chloride. The mixture was extracted with ethyl acetate (3×). The combined organic layer was washed with saturated aqueous saturated sodium bicarbonate and brine, dried over MgSO$_4$, filtered, and concentrated under reduced pressure. The crude compound was purified by flash chromatography (silica gel, 0-100% acetone in hexanes) to give 86 mg (66%) of EM-5855. $^1$H NMR (400 MHz, CDCl$_3$) δ: 0.97 (s, 3H, Me), 2.62 (d, J$_{gem}$=13.2 Hz, 1H, —CH$_2$-Pyr), 2.72 (m, 1H, H-6), 2.94 (d, J$_{gem}$=12.8 Hz, 1H, —CH$_2$-Pyr), 2.96 (m, 1H, H-6), 7.20 (d, J=8.3 Hz, 1H, Ar), 7.26 (d, J=5.9 Hz, 2H, Pyr), 7.39 (t, J=7.7 Hz, 1H, Ar), 8.50 (d, J=6.0 Hz, 2H, Pyr).

Preparation of EM-5854

To a solution of EM-5855 (86 mg, 0.22 mmol) in anhydrous dichloromethane (5 mL) at 0° C. was added 3-chloroperoxybenzoic acid (54 mg, 0.22 mmol). The mixture was stirred for 16 h at 22° C. and evaporated to dryness. The crude compound was purified by flash chromatography (silica gel, 0-10% methanol in chloroform) to give 67 mg (75%) of EM-5854. $^1$H NMR (400 MHz, CDCl$_3$) δ: 0.94 (s, 3H, Me), 2.57 (d, J$_{gem}$=13.5 Hz, 1H, —CH$_2$-Pyr), 2.68 (m, 1H, H-6), 2.93 (d, J$_{gem}$=13.3 Hz, 2H, —CH$_2$-Pyr, H-6), 7.17 (d, J=8.3 Hz, 1H, Ar), 7.27 (d, J=6.0 Hz, 2H, Pyr), 7.36 (t, J=7.7 Hz., 1H, Ar), 8.01 (d, J=6.8 Hz, 2H, Pyr).

Preparation of EM-8455

EM-8455 was prepared from the hydrochloride salt of picoline 7b (361 mg, 2.5 mmol) and compound 6 (182 mg, 0.61 mmol) using the procedure described for EM-5855. The amount of LDA used for this reaction was doubled to neutralize the hydrochloride salt. Flash chromatography gave 212 mg (84%) of EM-8455. $^1$H NMR (400 MHz, CDCl$_3$) δ: 0.98 (s, 3H, Me), 2.72 (m, 1H, H-6), 2.83 (d, J$_{gem}$=13.4 Hz, 1H, —CH$_2$-Pyr), 3.01 (m, 1H, H-6), 3.03 (d, J$_{gem}$=13.4 Hz, 1H, —CH$_2$-Pyr), 7.20 (d, J=8.2 Hz, 1H, Ar), 7.40 (t, J=7.7 Hz., 1H, Ar), 7.57 (t, J=5.9 Hz, 1H, Pyr), 8.37 (d, J=5.1 Hz, 1H, Pyr), 8.47 (d, J=1.1 Hz, 1H, Pyr).

Preparation of EM-8454

EM-8454 was prepared from EM-8455 (98 mg, 0.24 mmol) using the procedure described for EM-5854 to give 70 mg (68%) of EM-8454. $^1$H NMR (400 MHz, CDCl$_3$) δ: 0.95 (s, 3H, Me), 2.71 (m, 1H, H-6), 2.73 (d, J$_{gem}$=13.3 Hz, 1H, —CH$_2$-Pyr), 2.90 (d, J$_{gem}$=13.9 Hz, 1H, —CH$_2$-Pyr), 2.93 (m, 1H, H-6), 7.18 (d, J=8.3 Hz, 1H, Ar), 7.38 (t, J=7.6 Hz., 1H, Ar), 7.44 (t, J=7.2 Hz, 1H, Pyr), 7.93 (d, J=6.5 Hz, 1H, Pyr), 8.09 (d, J=6.0 Hz, 1H, Pyr).

Preparation of EM-8504

EM-8504 was prepared from picoline 7c (283 μL, 2.5 mmol) and compound 6 (150 mg, 0.50 mmol) using the procedure described for EM-5855 to give 90 mg (44%) of EM-8504. $^1$H NMR (400 MHz, CDCl$_3$) δ: 0.97 (s, 3H, Me), 2.33 (s, 3H, Me), 2.72 (m, 1H, H-6), 2.78 (d, J$_{gem}$=13.5 Hz, 1H, —CH$_2$-Pyr), 2.85 (d, J$_{gem}$=13.7 Hz, 1H, —CH$_2$-Pyr), 2.99 (m, 1H, H-6), 7.20 (d, J=8.2 Hz, 1H, Ar), 7.38 (bs, 1H, Pyr), 7.40 (t, J=7.5 Hz., 1H, Ar), 8.42 (bs, 2H, Pyr).

Preparation of EM-8505

EM-8505 was prepared from EM-8504 (26 mg, 0.064 mmol) using the procedure described for EM-5854 to give 20 mg (74%) of EM-8505. $^1$H NMR (400 MHz, CDCl$_3$) δ: 0.98 (s, 3H, Me), 2.27 (s, 3H, Me), 2.69 (m, 1H, H-6), 2.72 (d, J$_{gem}$=13.9 Hz, 1H, —CH$_2$-Pyr), 2.82 (d, J$_{gem}$=13.9 Hz, 1H, —CH$_2$-Pyr), 2.99 (m, 1H, H-6), 7.20 (d, J=8.3 Hz, 1H, Ar), 7.36 (d, J=6.7 Hz., 1H, Pyr), 7.38 (t, J=7.3 Hz, 1H, Ar), 7.93 (d, J=6.5 Hz, 1H, Pyr), 8.02 (s, 1H, Pyr).

Preparation of EM-8632

EM-8632 was prepared from picoline 7d (260 μL, 3.0 mmol) and compound 6 (150 mg, 0.50 mmol) using the procedure described for EM-5855 to give 132 mg (62%) of EM-8632. $^1$H NMR (400 MHz, acetone-d$_6$) δ: 1.00 (s, 3H, Me), 2.72 (m, 1H, H-6), 2.84 (d, J$_{gem}$=13.4 Hz, 1H, —CH$_2$-Pyr), 2.99 (m, 1H, H-6), 3.26 (d, J$_{gem}$=13.4 Hz, 1H, —CH$_2$-Pyr), 7.40 (d, J=8.2 Hz, 1H, Ar), 7.58 (m, 2H, Ar, Pyr), 8.37 (d, J=5.0 Hz, 1H, Pyr), 8.54 (s, 1H, Pyr).

Preparation of EM-8633

EM-8633 was prepared from EM-8632 (78 mg, 0.18 mmol) using the procedure described for EM-5854. The crude compound was purified by flash chromatography (silica gel, 0-10% methanol in dichloromethane) to give 18 mg (22%) of EM-8633. $^1$H NMR (400 MHz, CDCl$_3$) δ: 0.96 (s, 3H, Me), 2.72 (m, 1H, H-6), 2.79 (d, J$_{gem}$=13.8 Hz, 1H, —CH$_2$-Pyr), 2.99 (m, 1H, H-6), 3.11 (d, J$_{gem}$=13.8 Hz, 1H, —CH$_2$-Pyr), 7.19 (d, J=8.2 Hz, 1H, Ar), 7.40 (t, J=7.4 Hz, 1H, Ar), 7.53 (d, J=6.6 Hz, 1H, Pyr), 8.05 (d, J=6.3 Hz, 1H, Pyr), 8.28 (s, 1H, Pyr).

Preparation of Compound 7e

Commercial 4-picolylchloride hydrochloride (1.65 g, 10 mmol) was neutralized with an aqueous sodium carbonate solution (2.0 M). The mixture was extracted with diethyl ether (5×). The combined organic layer was dried over MgSO$_4$, filtered, and concentrated under reduced pressure. The mixture was diluted with anhydrous diethyl ether (20 mL) and kept on molecular sieves 4 Å for 16 h. To this solution was added tetrabutylammonium fluoride (9.4 g, 36 mmol) previously dried at 50° C. under reduced pressure for 48 h. The mixture was stirred for 48 h at 22° C. After completion of the reaction, the suspension was filtered, washed with diethyl ether, and concentrated under reduced pressure. The crude compound was purified by reduced pressure distillation to give 250 mg (25%) of compound 7e. $^1$H NMR (400 MHz, CDCl$_3$) δ: 5.37 and 5.49 (d, J=46.7 Hz, 2H, FCH$_2$-Pyr), 7.26 (d, J=5.2 Hz, 2H, Pyr), 8.64 (d, J=5.3 Hz, 2H, Pyr).

Preparation of EM-9075

EM-9075 was prepared from picoline 7e (165 mg, 1.5 mmol) and compound 6 (150 mg, 0.50 mmol) using the procedure described for EM-5855. The temperature was −90° C. instead of −78° C. for this reaction. The crude compound (2 diastereoisomers) was purified by reverse-phase semi-preparative HPLC (50-100% methanol in water) to give 20 mg (10%) of EM-9075 as the minor isomer. $^1$H NMR (400 MHz, CDCl$_3$) δ: 0.98 (s, 3H, Me), 2.72 (m, 1H, H-6), 2.99 (m, 1H, H-6), 5.51-5.63 (d, J=46.2 Hz, 1H, —CFH-Pyr), 7.20 (d, J=8.2 Hz, 1H, Ar), 7.39 (d, J=5.6 Hz, 2H, Pyr), 7.40 (t, J=7.4 Hz, 1H, Ar), 8.60 (d, J=5.7 Hz, 2H, Pyr). The major isomer was also isolated (40 mg, 20%). $^1$H NMR (300 MHz, CDCl$_3$) δ: 1.00 (s, 3H, Me), 2.71 (m, 1H, H-6), 2.95 (m, 1H, H-6), 5.40 and 5.55 (d, J=44.8 Hz, 1H, —CFH-Pyr), 7.20 (d, J=8.3 Hz, 1H, Ar), 7.40 (m, 3H, Ar, Pyr), 8.60 (bs, 2H, Pyr).

Preparation of EM-9103

To a suspension of EM-9075 (20 mg, 0.049 mmol) in methanol-water/3:1 (4 mL) was added magnesium monoperoxyphthalate (100 mg, 0.16 mmol). The solution was stirred under reflux for 2 h. After completion of the reaction (TLC), the mixture was diluted with aqueous saturated sodium bicarbonate and extracted with ethyl acetate (3×). The combined organic layer was washed with aqueous saturated sodium carbonate and brine, dried over MgSO$_4$, filtered, and concentrated under reduced pressure. The crude compound was purified by reverse-phase semi-preparative HPLC (50-100% methanol in water) to give 12.5 mg (60%) of EM-9103. $^1$H NMR (400 MHz, CDCl$_3$) δ: 0.99 (s, 3H, Me), 2.72 (m, 1H, H-6), 2.99 (m, 1H, H-6), 5.51 and 5.63 (d, J=45.7 Hz, 1H, —CFH-Pyr), 7.20 (d, J=8.2 Hz, 1H, Ar), 7.39 (t, J=7.4 Hz, 1H, Ar), 7.40 (d, J=7.0 Hz, 2H, Pyr), 8.07 (d, J=6.8 Hz, 2H, Pyr).

Preparation of EM-9088

EM-9088 was prepared from picoline 7f (250 μL, 2.0 mmol) and compound 6 (100 mg, 0.33 mmol) using the procedure described for EM-5855. For the reaction between LDA (0.5 M, 3.5 mL, 1.8 mmol) and 7f, the temperature was risen from −78° C. to 0° C. over a 1 h period. The crude compound was purified by flash chromatography (silica gel, 0-100% acetone in hexanes) to give 10 mg (8%) of EM-9088. $^1$H NMR (400 MHz, CDCl$_3$) δ: 0.97 (s, 3H, Me), 2.55 (s, 3H, Me), 2.58 (d, J$_{gem}$=13.2 Hz, 1H, —CH$_2$-Pyr), 2.72 (m, 1H, H-6), 2.89 (d, J$_{gem}$=12.9 Hz, 1H, —CH$_2$-Pyr), 2.99 (m, 1H, H-6), 7.07 (d, J=5.0 Hz, 1H, Pyr), 7.13 (s, 1H, Pyr), 7.20 (d, J=8.2 Hz, 1H, Ar), 7.40 (t, J=7.9 Hz, 1H, Ar), 8.41 (d, J=5.0 Hz, 1H, Pyr).

Preparation of EM-9108

EM-9108 was prepared from EM-9088 (30 mg, 0.074 mmol) using the procedure described for compound EM-9103 to give 7 mg (23%) of EM-9108. $^1$H NMR (400 MHz, CDCl$_3$) δ: 0.97 (s, 3H, Me), 2.53 (s, 3H, Me), 2.57 (d, J$_{gem}$=13.5 Hz, 1H, —CH$_2$-Pyr), 2.72 (m, 1H, H-6), 2.90 (d, J$_{gem}$=13.4 Hz, 1H, —CH$_2$-Pyr), 2.99 (m, 1H, H-6), 7.14 (d, J=6.6 Hz, 1H, Pyr), 7.20 (d, J=8.3 Hz, 1H, Ar), 7.24 (s, 1H, Pyr), 7.40 (t, J=7.7 Hz, 1H, Ar), 8.18 (d, J=6.6 Hz, 1H, Pyr).

Example 2

Synthesis of EM-8439

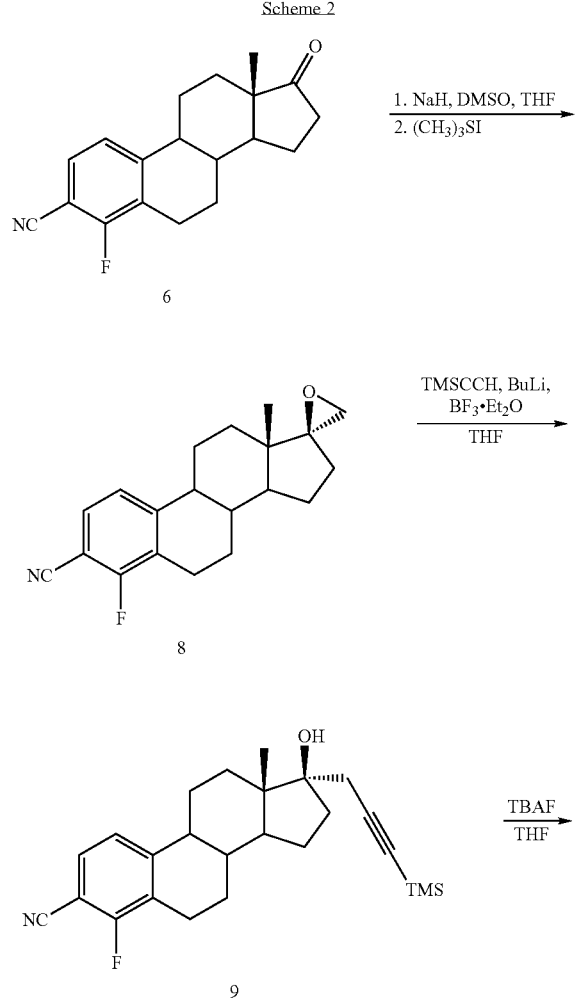

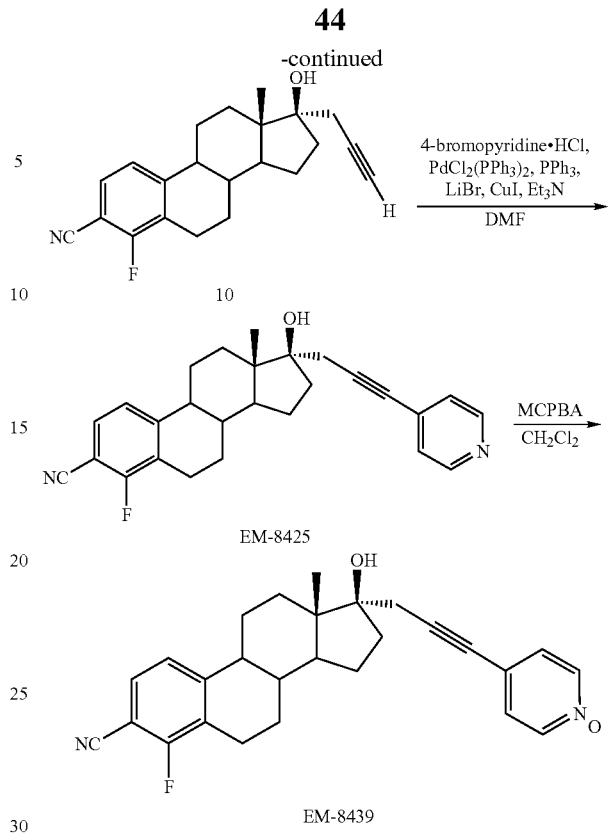

Preparation of Compound 8

In a dry 250 mL round-bottom flask equipped with a magnetic stirrer, under an argon atmosphere, a suspension of sodium hydride (1.2 g, 60% in oil, 30 mmol) in DMSO (25 mL) was stirred at 75° C. for 1 h. The mixture was ice-cooled to 0° C. and THF (10 mL) was added following by a solution of trimethylsulfonium iodide (6.2 g, 30 mmol) in DMSO (35 mL). The mixture was stirred for 5 min and a solution of compound 6 (1.50 g, 5.04 mmol) in THF (50 mL) was added. The mixture was stirred at room temperature for 3 h. After completion of the reaction (TLC), the reaction was quenched by addition of aqueous saturated ammonium chloride. The mixture was extracted with ethyl acetate (3×). The combined organic layer was washed with water (5×) and brine, dried over MgSO$_4$, filtered, and concentrated under reduced pressure. The crude compound was purified by flash chromatography (silica gel, 0-30% ethyl acetate in hexanes) to give 1.02 g (65%) of compound 8. $^1$H NMR (400 MHz, CDCl$_3$) δ: 0.93 (s, 3H, Me), 2.66 (d, J$_{gem}$=5.0 Hz, 1H, —CH$_2$—O), 2.72 (m, 1H, H-6), 2.96 (d, J$_{gem}$=5.2 Hz, 1H, —CH$_2$—O), 2.98 (m, 1H, H-6), 7.17 (d, J=8.2 Hz, 1H, Ar), 7.38 (t, J=7.6 Hz, 1H, Ar).

Preparation of Compound 9

To a solution of n-BuLi (2.5 M in hexanes, 2.4 mL, 5.9 mmol) in anhydrous THF (5 mL) at −78° C. was added dropwise (trimethylsilyl)acetylene (0.91 mL, 6.4 mmol). The mixture was stirred for 30 min at −78° C. A solution of compound 8 (364 mg, 1.17 mmol) in THF (10 mL) was added, followed by borontrifluoride diethyl etherate (0.3 mL, 2.3 mmol) and the mixture was stirred for 1 h at −78° C. After completion of the reaction (TLC), the reaction was quenched by addition of aqueous saturated ammonium chloride. The mixture was extracted with ethyl acetate (3×). The combined organic layer was washed with aqueous saturated sodium bicarbonate and brine, dried over MgSO$_4$, filtered, and concentrated under reduced pressure. The crude compound was purified by flash chromatography (silica gel, 0-30% acetone in hexanes) to give 331 mg (70%) of compound 9. $^1$H NMR (400 MHz, acetone-d$_6$) δ: 0.14 (s, 9H, TMS), 0.93 (s, 3H, Me), 2.51 (s, 2H, —CH$_2$—CC), 2.70 (m, 1H, H-6), 2.91 (m, 1H, H-6), 7.33 (d, J=8.3 Hz, 1H, Ar), 7.53 (t, J=7.7 Hz, 1H, Ar).

Preparation of Compound 10

To a solution of compound 9 (331 mg, 0.808 mmol) in anhydrous THF (10 mL) at 0° C. was added a solution of tetrabutylammonium fluoride (1.0 M in THF, 2.0 mL, 2.0 mmol). The mixture was stirred for 2 h at 0° C. After completion of the reaction (TLC), water was added and the mixture was extracted with ethyl acetate (3×). The combined organic layer was washed with water and brine, dried over MgSO$_4$, filtered, and concentrated under reduced pressure. The crude compound was purified by flash chromatography (silica gel, 0-50% acetone in hexanes) to give 251 mg (92%) of compound 10. $^1$H NMR (400 MHz, CDCl$_3$) δ: 0.94 (s, 3H, Me), 2.09 (s, 1H, C≡CH), 2.40 (d, J$_{gem}$=13.8 Hz, 1H, —CH$_2$—CC), 2.56 (d, J$_{gem}$=16.4 Hz, 1H, —CH$_2$—CC), 2.70 (m, 1H, H-6), 2.91 (m, 1H, H-6), 7.16 (d, J=8.3 Hz, 1H, Ar), 7.36 (t, J=7.7 Hz, 1H, Ar).

Preparation of EM-8425

A mixture of compound 10 (52 mg, 0.16 mmol), 4-bromopyridine hydrochloride (91 mg, 0.47 mmol), lithium bromide (40 mg, 0.47 mmol), triphenylphosphine (2.6 mg, 0.0099 mmol), dichlorobis(triphenylphosphine)palladium (II) (4.3 mg, 0.0061 mmol), and triethylamine (326 µL, 2.4 mmol) in DMF (0.5 mL) was purged with argon while stirring for 15 min. Then, copper(I) iodide (1 mg, 0.004 mmol) was added and the mixture was purged with argon for another 10 min. The mixture was stirred for 3 h at 65° C. The mixture was filtered through celite and washed several times with ethyl acetate. The mixture was diluted with aqueous saturated sodium bicarbonate and extracted with ethyl acetate (3×). The combined organic layer was washed with aqueous saturated sodium bicarbonate and brine, dried over MgSO$_4$, filtered, and concentrated under reduced pressure. The crude compound was purified by flash chromatography (silica gel, 0-30% acetone in hexanes) to give 34.5 mg (54%) of EM-8425. $^1$H NMR (400 MHz, CDCl$_3$) δ: 0.98 (s, 3H, Me), 2.68 (d, J$_{gem}$=16.6 Hz, 1H, —CH$_2$—C≡C), 2.70 (m, 1H, H-6), 2.81 (d, J$_{gem}$=16.6 Hz, 1H, —CH$_2$—C≡C), 2.95 (m, 1H, H-6), 7.17 (d, J=8.2 Hz, 1H, Ar), 7.28 (bs, 2H, Pyr), 7.38 (t, J=7.6 Hz, 1H, Ar), 8.53 (bs, 2H, Pyr).

Preparation of EM-8439

EM-8439 was prepared from EM-8425 (42 mg, 0.10 mmol) using the procedure described for EM-5854. The crude compound was purified by flash chromatography (silica gel, 0-10% methanol in dichloromethane) to give 29.7 mg (69%) of EM-8439. $^1$H NMR (400 MHz, CDCl$_3$) δ: 0.98 (s, 3H, Me), 2.68 (d, J$_{gem}$=16.8 Hz, 1H, —CH$_2$—C≡C), 2.70 (m, 1H, H-6), 2.81 (d, J$_{gem}$=16.7 Hz, 1H, —CH$_2$—C≡C), 2.95 (m, 1H, H-6), 7.17 (d, J=8.2 Hz, 1H, Ar), 7.26 (bs, 2H, Pyr), 7.39 (t, J=7.4 Hz, 1H, Ar), 8.14 (bs, 2H, Pyr).

Example 3

Synthesis of EM-8426

Scheme 3

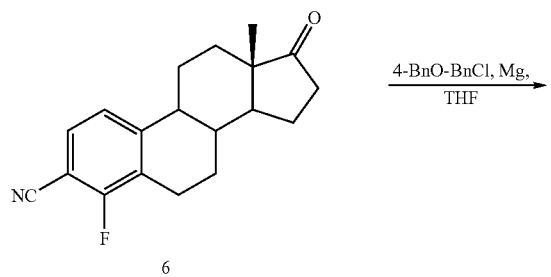

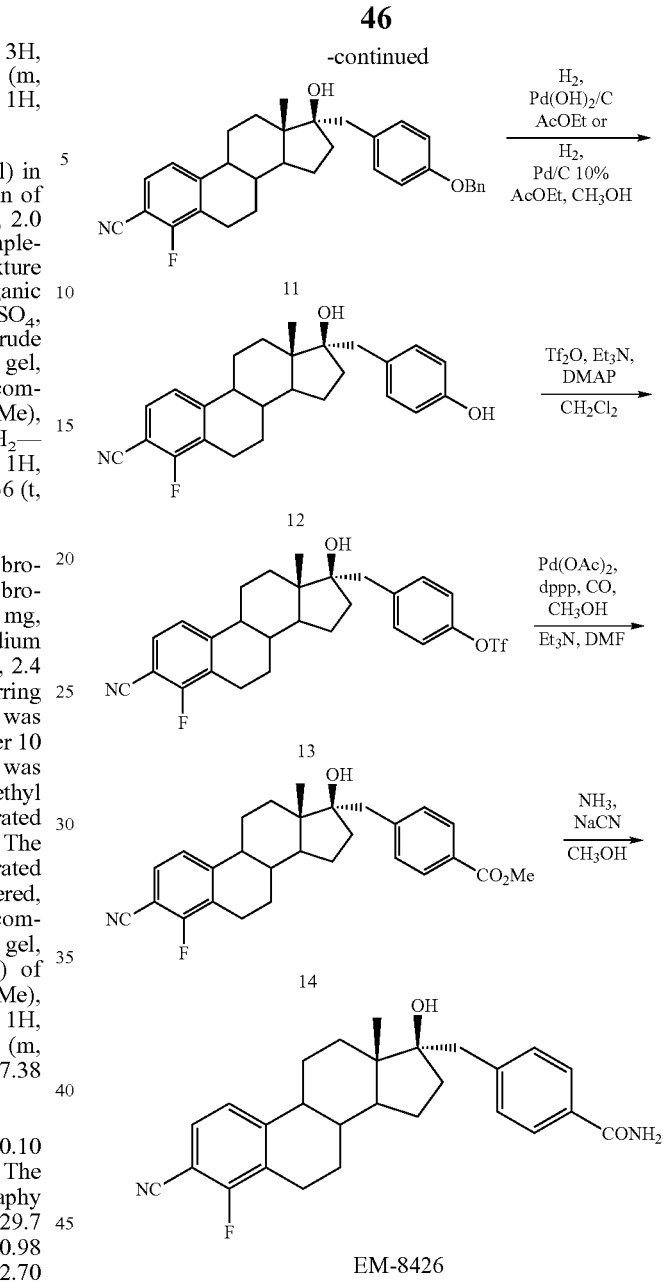

Preparation of Compound 11

After the addition of magnesium powder (515 mg, 21.2 mmol) in a dry 3-neck round-bottom flask equipped with a magnetic stirrer, under an argon atmosphere, the system was flame dried. After cooling, THF (2 mL) was added. The suspension was stirred vigorously while a 4-benzyloxybenzyl chloride (1.0 g, 4.3 mmol) solution in THF (7 mL) was added dropwise until the temperature rose 30° C. The temperature was kept below 30° C. with an ice bath during the rest of the addition. The mixture was stirred at room temperature for 30 min. Compound 6 (200 mg, 0.67 mmol) was dissolved in THF (10 mL) and ice-cooled to 0° C. The freshly prepared Grignard solution (0.5 M) was added dropwise to this solution. The mixture was stirred for 1 h at 0° C. After completion of the reaction (TLC), the reaction was quenched by addition of aqueous saturated ammonium chloride. The mixture was extracted with ethyl acetate (3×). The combined organic layer was washed with aqueous saturated sodium bicarbonate and brine, dried over MgSO$_4$, filtered, and concentrated under reduced pressure. The crude compound was purified by flash chromatography (silica gel, 0-80% acetone in hexanes) to give 246 mg (70%) of compound 11. $^1$H NMR (400 MHz, CDCl$_3$) δ: 0.97 (s, 3H, Me), 2.62 (d, J$_{gem}$=13.5 Hz, 1H, C—CH$_2$-Ph), 2.67 (m, 1H, H-6), 2.85 (d, J$_{gem}$=12.7 Hz, 1H, C—CH$_2$-Ph), 2.90 (m, 1H, H-6), 5.03 (s, 2H, O—CH$_2$-Ph), 6.93 (d, J=8.6 Hz, 2H, Ar), 7.28 (d, J=8.6 Hz, 2H, Ar), 7.31-7.50 (m, 7H, Ar, OBn).

Preparation of Compound 12

A mixture of compound 11 (200 mg, 0.40 mmol) and palladium hydroxide (20 wt. % on carbon, wet, 100 mg) in ethyl acetate (10 mL) was stirred under hydrogen (1 atm) at 22° C. for 16 h. After completion of the reaction (TLC), the mixture was filtered through celite and washed several times with ethyl acetate. The solvent was removed under reduced pressure to give 160 mg (98%) of compound 12. $^1$H NMR (400 MHz, CDCl$_3$) δ: 0.97 (s, 3H, Me), 2.60 (d, J$_{gem}$=13.5 Hz, 1H, —CH$_2$-Ph), 2.71 (m, 1H, H-6), 2.86 (d, J$_{gem}$=12.7 Hz, 1H, —CH$_2$-Ph), 2.95 (m, 1H, H-6), 6.80 (d, J=8.5 Hz, 2H, Ar), 7.16 (d, J=8.4 Hz, 2H, Ar), 7.20 (d, J=8.2 Hz, 1H, Ar), 7.40 (t, J=7.7 Hz, 1H, Ar).

Alternative Procedure:

A mixture of compound 11 (200 mg, 0.40 mmol) and palladium (10 wt. % on activated carbon, 100 mg) in ethyl acetate-methanol/3:1 (10 mL) was stirred under hydrogen (1 atm) at 22° C. for 16 h. After completion of the reaction (TLC), the mixture was filtered through celite and washed several times with ethyl acetate. The solvent was removed under reduced pressure to give 160 mg (98%) of compound 12.

Preparation of Compound 13

To a solution of compound 12 (320 mg, 0.79 mmol) in anhydrous dichloromethane (15 mL) was added triethylamine (220 μL, 1.6 mmol) and 4-(dimethylamino)pyridine (10 mg, 0.082 mmol). The mixture was ice-cooled to 0° C. and trifluoromethanesulfonic anhydride (160 μL, 0.95 mmol) was added dropwise. The mixture was stirred for 1 h at 0° C. After completion of the reaction (TLC), the mixture was diluted with aqueous saturated sodium bicarbonate. The mixture was extracted with dichloromethane (3×). The combined organic layer was washed with aqueous saturated sodium bicarbonate and brine, dried over MgSO$_4$, filtered, and concentrated under reduced pressure. The crude compound was purified by flash chromatography (silica gel, 0-30% ethyl acetate in hexanes) to give 305 mg (72%) of compound 13. $^1$H NMR (400 MHz, CDCl$_3$) δ: 0.97 (s, 3H, Me), 2.66 (d, J$_{gem}$=13.5 Hz, 1H, —CH$_2$-Ph), 2.72 (m, 1H, H-6), 2.96 (d, J$_{gem}$=12.7 Hz, 1H, —CH$_2$-Ph), 2.99 (m, 1H, H-6), 7.20 (d, J=8.2 Hz, 1H, Ar), 7.22 (d, J=8.8 Hz, 2H, Ar), 7.39 (d, J=8.5 Hz, 2H, Ar) 7.40 (t, J=7.7 Hz, 1H, Ar).

Preparation of Compound 14

A solution of compound 13 (165 mg, 0.307 mmol) and methanol (260 μL) in DMF (2.3 mL) was purged with argon while stirring for 15 min. Triethylamine (1.0 mL, 7.2 mmol) was added and the mixture was purged with argon for another 10 min. Then, palladium(II) acetate (3.6 mg, 0.016 mmol) and 1,3-bis(diphenylphosphino)propane (6.0 mg, 0.015 mmol) were added and the mixture was stirred at 90° C. for 3 h while bubbling carbon monoxide. After completion of the reaction, the mixture was filtered through celite and washed several times with ethyl acetate. The ethyl acetate solution was washed with water and brine, dried over MgSO$_4$, filtered, and concentrated under reduced pressure. The crude compound was purified by flash chromatography (silica gel, 0-30% ethyl acetate in hexanes) to give 115 mg (84%) of compound 14. $^1$H NMR (400 MHz, CDCl$_3$) δ: 0.97 (s, 3H, Me), 2.72 (m, 2H —CH$_2$-Ph, H-6), 2.97 (m, 2H, —CH$_2$-Ph, H-6), 3.92 (s, 3H, MeO), 7.20 (d, J=8.3 Hz, 1H, Ar), 7.38 (d, J=8.3 Hz, 2H, Ar), 7.40 (t, J=7.7 Hz, 1H, Ar), 7.99 (d, J=8.2 Hz, 2H, Ar).

Preparation of EM-8426

In a Schlenk tube, a mixture of compound 14 (45 mg, 0.10 mmol) and sodium cyanide (197 mg, 4.02 mmol) in dry methanol (2 mL) was purged with argon while stirring for 15 min. The mixture was cooled to −78° C. Ammonia (2 mL) was condensed and the tube was sealed. The mixture was stirred for 20 h at 65° C. After completion of the reaction, the mixture was cooled to −78° C. before the tube was opened. The temperature was brought back to 22° C. and the excess of ammonia was evaporated. The mixture was diluted with water and extracted with ethyl acetate (3×). The combined organic layer was washed with water and brine, dried over MgSO$_4$, filtered, and concentrated under reduced pressure. The crude compound was purified by reverse-phase semi-preparative HPLC (50-100% methanol in water) to give 12.7 mg (30%) of EM-8426. $^1$H NMR (400 MHz, CDCl$_3$) δ: 0.98 (s, 3H, Me), 2.70 (m, 2H —CH$_2$-Ph, H-6), 2.99 (m, 2H, —CH$_2$-Ph, H-6), 5.60-6.15 (bs, 2H, NH$_2$), 7.20 (d, J=8.2 Hz, 1H, Ar), 7.40 (m, 3H, Ar), 7.77 (d, J=8.1 Hz, 2H, Ar).

Example 4

Synthesis of EM-8791

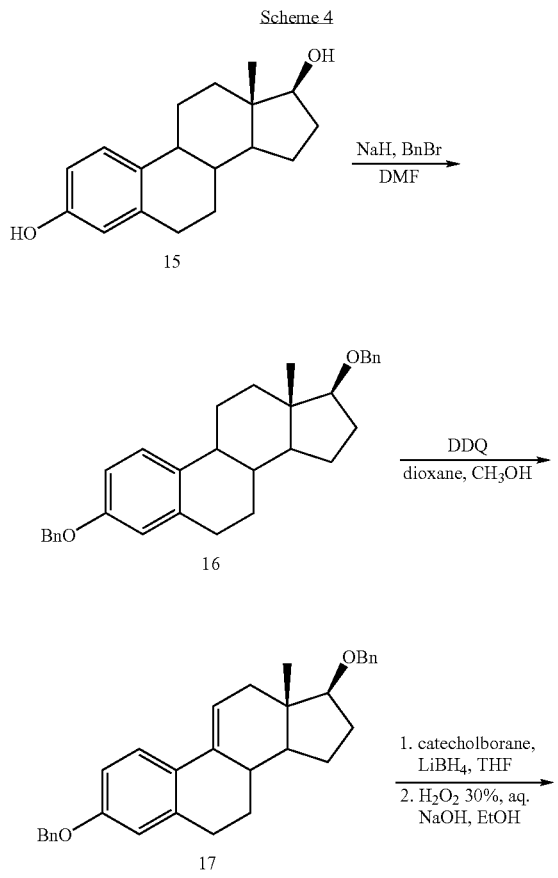

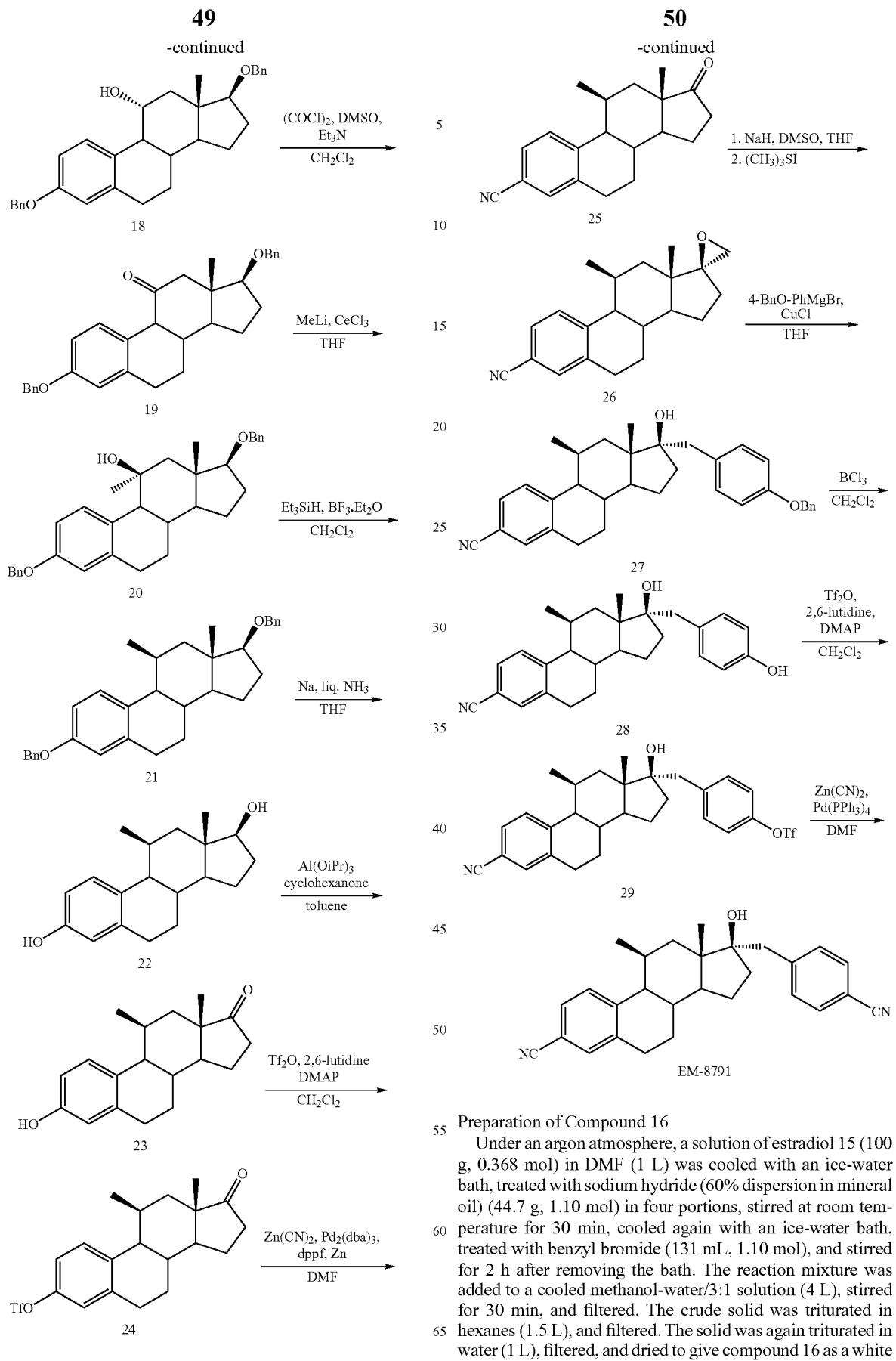

Preparation of Compound 16

Under an argon atmosphere, a solution of estradiol 15 (100 g, 0.368 mol) in DMF (1 L) was cooled with an ice-water bath, treated with sodium hydride (60% dispersion in mineral oil) (44.7 g, 1.10 mol) in four portions, stirred at room temperature for 30 min, cooled again with an ice-water bath, treated with benzyl bromide (131 mL, 1.10 mol), and stirred for 2 h after removing the bath. The reaction mixture was added to a cooled methanol-water/3:1 solution (4 L), stirred for 30 min, and filtered. The crude solid was triturated in hexanes (1.5 L), and filtered. The solid was again triturated in water (1 L), filtered, and dried to give compound 16 as a white solid (116.6 g, 70%). $^1$H NMR (400 MHz, CDCl$_3$) δ: 0.87 (s, 3H, Me), 2.84 (m, 2H, H-6), 3.50 (t, J=8.6 Hz, 1H, H-17), 4.58 (s, 2H, C—O—CH$_2$Ph), 5.03 (s, 2H, Ar—O—CH$_2$Ph), 6.71 (s, 1H, H-4), 6.80 (d, J=8.2 Hz, H, H-2), 7.20 (d, J=8.5 Hz, 1H, H-1), 7.37 (m, 10H, Ar).

Preparation of Compound 17

A solution of compound 16 (116.6 g, 0.258 mol) in dioxane-methanol/1:1 mixture (2 L) was treated with 2,3-dichloro-5,6-dicyanobenzoquinone (87.8 g, 0.387 mol) and stirred for 20 h at room temperature. The reaction mixture was concentrated to dryness, and the residue was dissolved in dichloromethane. The solution was filtered on neutral alumina and concentrated. The crude solid 17 (108.5 g, 93%) was used directly in the next step. $^1$H NMR (400 MHz, CDCl$_3$) δ: 0.89 (s, 3H, Me), 2.81 (m, 2H, H-6), 3.60 (t, J=8.6 Hz, 1H, H-17), 4.58 (m, 2H, C—O—CH$_2$Ph), 5.05 (s, 2H, Ar—O—CH$_2$Ph), 6.11 (m, 1H, H-11), 6.69 (s, 1H, H-4), 6.79 (d, J=8.2 Hz, 1H, H-2), 7.38 (m, 10H, Ar), 7.54 (d, J=8.8 Hz, H, H-1).

Preparation of Compound 18

Under an argon atmosphere, a solution of compound 17 (108.5 g, 0.241 mol) in anhydrous THF (1.2 L) was treated with catecholborane (1.0 M in THF, 722 mL, 0.722 mol) and lithium borohydride (7.29 g, 0.335 mol), and stirred overnight at room temperature. The reaction mixture was then added in portions to an ice cold mixture of 33% sodium hydroxide (108.6 g), ethanol (1.0 L) and 30% hydrogen peroxide (0.75 L), and stirred for 6 h at room temperature. The reaction mixture was partitioned between water and ethyl acetate. The aqueous phase was extracted one time with ethyl acetate; and the combined organic phase was washed 3 times with water and 2 times with brine, dried over MgSO$_4$, filtered, and evaporated to give a brown oil. The crude product was then chromatographed (toluene to toluene-ethyl acetate/89:11) to provide compound 18 as a beige foam (59.5 g, 53%). $^1$H NMR (400 MHz, CDCl$_3$) δ: 0.86 (s, 3H, Me), 2.82 (m, 2H, H-6), 3.53 (t, J=8.2 Hz, 1H, H-17), 4.22 (m, 1H, H-11), 4.58 (s, 2H, C—O—CH$_2$Ph), 5.05 (s, 2H, Ar—O—CH$_2$Ph), 6.75 (s, 1H, H-4), 6.80 (d, J=8.7 Hz, 1H, H-2), 7.36 (m, 10H, Ar), 7.86 (d, J=8.7 Hz, 1H, H-1).

Preparation of Compound 19

Under an argon atmosphere, a solution of oxalyl chloride (18.8 mL, 0.216 mol) in dichloromethane (200 mL) was cooled at −60° C., treated with a solution of DMSO (30.6 mL, 0.432 mol) in dichloromethane (400 mL), and stirred 30 min. The reaction mixture was then treated with a solution of compound 18 (59.5 g, 0.127 mole) in dichloromethane (600 mL), stirred for 1.5 h, and treated with triethylamine (124 mL, 0.888 mol). After removing the bath, water was added to the reaction mixture. The organic phase was washed 4 times with water and 2 times with brine, dried over MgSO$_4$, filtered, and evaporated. The crude product was filtered on silica gel using dichloromethane as eluent and triturated from methanol overnight to give compound 19 (48.3 g, 82%). $^1$H NMR (400 MHz, CDCl$_3$) δ: 0.87 (s, 3H, Me), 2.47 (d, J=11.6 Hz, 1H), 2.68 (d, J=11.5 Hz, 1H), 2.84 (m, 2H, H-6), 3.47 (d, J=10.8 Hz, 1H, H-9), 3.73 (t, J=8.2 Hz, 1H, H-17), 4.55 (s, 2H, C—O—CH$_2$Ph), 5.04 (s, 2H, Ar—O—CH$_2$Ph), 6.70 (s, 1H, H-4), 6.83 (d, J=8.7 Hz, 1H, H-2), 7.25 (d, J=8.7 Hz, 1H, H-1), 7.38 (m, 10H, Ar).

Preparation of Compound 20

A suspension of anhydrous cerium(III) chloride (10.6 g, 42.9 mmol) in anhydrous THF (60 mL) was stirred overnight at room temperature under argon, cooled at −78° C., treated with methyl lithium (0.8 M in diethyl ether, 54 mL, 43 mmol), and stirred for 30 min. The organometallic reagent was treated with a solution of compound 19 (10.1 g, 21.7 mmol) in anhydrous THF (70 mL), stirred for 30 min, and quenched with ethyl acetate. After removing the bath, the reaction mixture was concentrated. The residue was poured in ethyl acetate and a small amount of water and filtered on celite. The organic phase was washed with water, aqueous saturated sodium bicarbonate and brine, dried over MgSO$_4$, filtered, and evaporated. The crude solid 20 (10.6 g, 100%) was used directly in the next step. $^1$H NMR (400 MHz, CDCl$_3$) δ: 1.09 (s, 3H, Me), 1.63 (s, 3H, Me), 2.71 (m, 2H, H-6), 3.47 (t, J=7.7 Hz, 1H, H-17), 4.57 (s, 2H, C—O—CH$_2$Ph), 5.05 (s, 2H, Ar—O—CH$_2$Ph), 6.78 (m, 2H, H-4, H-2), 7.36 (m, 10H, Ar), 7.77 (d, J=8.5 Hz, 1H, H-1).

Preparation of Compound 21

A solution of compound 20 (10.6 g, 21.7 mmol) in dichloromethane (400 mL) was cooled at 0° C., treated with triethylsilane (20 mL, 125 mmol) and boron trifluoride diethyl etherate (44 mL, 350 mmol) over a 10 min period, and stirred for 1 h. The reaction mixture was quenched with aqueous saturated sodium bicarbonate (200 mL) and the bath was removed. The organic phase was concentrated and diluted with ethyl acetate (400 mL). The organic phase was washed 2 times with aqueous saturated sodium bicarbonate and brine, dried over MgSO$_4$, filtered, and evaporated. The crude solid 21 (10.1 g, 100%) was used directly in the next step. $^1$H NMR (400 MHz, CDCl$_3$) δ: 0.91 (d, J=8.5 Hz, 3H, Me-11), 1.01 (s, 3H, Me), 2.75 (m, 2H, H-6), 3.48 (t, J=7.6 Hz, 1H, H-17), 4.58 (m, 2H, C—O—CH$_2$Ph), 5.03 (s, 2H, Ar—O—CH$_2$Ph), 6.69 (s, 1H, H-4), 6.79 (d, J=8.6 Hz, 1H, H-2), 7.10 (d, J=8.6 Hz, 1H, H-1), 7.37 (m, 10H, Ar).

Preparation of Compound 22

Liquid ammonia (200 mL) was freshly condensed at −78° C. and diluted with a solution of compound 21 (10.1 g, 21.7 mmol) in THF (200 mL). The reaction mixture was treated with sodium (4.06 g, 177 mmol) in small portions, refluxed for 3 h, quenched with ammonium chloride (23.6 g) in small portions and water (100 mL), and stirred overnight to let ammonia to evaporate. The reaction mixture was extracted with ethyl acetate after adjusting the pH to 5 with HCl 1 N. The organic phase was washed 2 times with brine, dried over MgSO$_4$, filtered, and evaporated. The crude solid 22 (7.06 g, 100%) was used directly in the next step. $^1$H NMR (400 MHz, CDCl$_3$) δ: 0.91 (m, 6H, Me), 2.72 (m, 2H, H-6), 3.70 (m, 1H, H-17), 6.54 (s, 1H, H-4), 6.63 (d, J=8.5 Hz, 1H, H-2), 7.05 (d, J=8.5 Hz, 1H, H-1).

Preparation of Compound 23

A solution of compound 22 (7.06 g, 21.7 mmol) in cyclohexanone-toluene/2:3 (250 mL) was treated with aluminum isopropoxide (10.6 g, 52.1 mmol), refluxed for 5 h, and allowed to cool to room temperature overnight. The reaction mixture was treated with HCl 1 N and extracted 3 times with ethyl acetate. The combined organic phase was washed with water and brine, dried over MgSO$_4$, filtered, and evaporated. The residue was coevaporated 4 times with water to remove the cyclohexanone and triturated in hexanes-ethyl acetate/19:1 (150 mL) to give compound 23 as a beige solid (4.44 g, 72%). $^1$H NMR (400 MHz, CDCl$_3$) δ: 0.87 (d, J=7.5 Hz, 3H, Me-11), 1.00 (s, 3H, Me), 2.74 (m, 2H, H-6), 6.52 (s, 1H, H-4), 6.61 (d, J=8.4 Hz, 1H, H-2), 7.00 (d, J=8.4 Hz, 1H, H-1).

Preparation of Compound 24

A solution of compound 23 (1.39 g, 4.89 mmol) in dichloromethane (75 mL) was cooled at 0° C., treated with trifluoromethanesulfonic anhydride (1.15 mL, 6.85 mmol), 2,6-lutidine (1.14 mL, 9.8 mmol) and 4-dimethylaminopyridine (32 mg, 0.26 mmol), and stirred for 3 h. The reaction mixture was quenched with aqueous saturated ammonium chloride and concentrated. The residue was dissolved in ethyl acetate. The organic phase was washed with water, HCl 1 N (2×), water, aqueous saturated sodium bicarbonate (2×) and brine, dried over MgSO$_4$, filtered, and evaporated. The crude product was chromatographed (hexanes-ethyl acetate/17:3 to hexanes-ethyl acetate/4:1) to afford compound 24 (1.90 g, 93%). $^1$H NMR (400 MHz, CDCl$_3$) δ: 0.92 (d, J=7.5 Hz, 3H, Me-11), 1.06 (s, 3H, Me), 2.90 (m, 2H, H-6), 7.00 (s, 1H, H-4), 7.05 (d, J=8.4 Hz, 1H, H-2), 7.27 (d, J=8.4 Hz, 1H, H-1).

Preparation of Compound 25

Under an argon atmosphere, a suspension of compound 24 (1.90 g, 4.55 mmol), zinc cyanide (320 mg, 2.73 mmol), zinc (46 mg, 0.70 mmol), 1,1'-bis(diphenylphosphino)ferrocene (252 mg, 0.455 mmol) and tris(dibenzylideneacetone)dipalladium (0) (208 mg, 0.227 mmol) in DMF (bubbled with argon, 35 mL) was bubbled with argon for 15 min and heated at 120° C. for 3 h and at 105° C. overnight. The reaction mixture was cooled at room temperature and concentrated. The residue was dissolved in ethyl acetate then the organic phase was washed with water (2×), aqueous saturated sodium bicarbonate and brine, dried over MgSO$_4$, filtered, and evaporated. The crude product was chromatographed (toluene-ethyl acetate/19:1) to give compound 25 (0.901 g, 67%). $^1$H NMR (400 MHz, CDCl$_3$) δ: 0.89 (d, J=7.5 Hz, 3H, Me-11), 1.04 (s, 3H, Me), 2.87 (m, 2H, H-6), 7.29 (d, J=8.2 Hz, 1H, Ar), 7.38 (s, 1H, Ar), 7.42 (d, J=8.1 Hz, 1H, Ar).

Preparation of Compound 26

Compound 26 was prepared using the same method described for compound 8. Compound 25 (0.900 g, 3.07 mmol) gave compound 26 (0.681 g, 72%). $^1$H NMR (400 MHz, CDCl$_3$) δ: 0.85 (d, J=7.5 Hz, 3H, Me-11), 1.07 (s, 3H, Me), 2.64 (d, J=7.5 Hz, 1H, CH$_2$—O), 2.85 (m, 2H, H-6), 2.99 (d, J=7.5 Hz, 1H, CH$_2$—O), 7.28 (d, J=8.2 Hz, 1H, Ar), 7.37 (s, 1H, Ar), 7.41 (d, J=8.1 Hz, 1H, Ar).

Preparation of Compound 27

After the addition of magnesium powder (0.74 g, 30 mmol) in a dry 3-neck round-bottom flask equipped with a magnetic stirrer, under an argon atmosphere, the system was flame dried. After cooling, dry THF (10 mL) was added. The suspension was stirred vigorously while a 4-benzyloxybromobenzene (3.93 g, 14.9 mmol) solution in THF (3 mL) was added dropwise until the temperature rose 30° C. The temperature was kept below 30° C. with an ice bath during the rest of the addition. The mixture was stirred at room temperature for 30 min. A portion of the freshly prepared Grignard solution (0.79 M, 2.8 mL, 2.2 mmol) was added to a solution of copper(I) chloride (3 mg, 0.03 mmol) in THF (2.5 mL) and stirred 10 min at −10° C. Then, a solution of compound 26 (133 mg, 0.433 mmol) in THF (2.5 mL) was added. The mixture was stirred for 3 h at 0° C. After completion of the reaction (TLC), the reaction was quenched by addition of aqueous saturated ammonium chloride. The mixture was extracted with ethyl acetate. The combined organic layer was washed with water (2×), aqueous saturated sodium bicarbonate and brine, dried over MgSO$_4$, filtered, and concentrated under reduced pressure. The crude product was purified by flash chromatography (hexanes-dichloromethane-ethyl acetate/34:5:11) to give impure compound 27 (262 mg) which was used in the next step. $^1$H NMR (400 MHz, CDCl$_3$) δ: 0.94 (d, J=7.5 Hz, 3H, Me-11), 1.12 (s, 3H, Me), 2.63 (m, 1H, C—CH$_2$-Ph), 2.89 (m, 3H, C—CH$_2$-Ph, H-6), 5.08 (s, 2H, O—CH$_2$-Ph), 6.97 (d, J=8.6 Hz, 2H, Ar), 7.23 (d, J=8.6 Hz, 2H, Ar), 7.43 (m, 8H, Ar).

Preparation of Compound 28

Under an argon atmosphere, a solution of impure compound 27 (262 mg) in dichloromethane (10 mL) was cooled at −45° C., treated with boron trichloride (1.0 M in dichloromethane, 1.0 mL, 1.0 mmol), and stirred below −35° C. for 2 h. The reaction mixture was slowly warmed at −20° C. over a 30 min period, then quenched with methanol, and evaporated. The residue was dissolved in ethyl acetate. The organic phase was washed with water, aqueous saturated sodium bicarbonate (2×) and brine, dried over MgSO$_4$, filtered, and evaporated. The crude product was chromatographed (dichloromethane to dichloromethane-methanol/19:1) to give compound 28 (144 mg, 83%). $^1$H NMR (400 MHz, acetone-d$_6$) δ: 0.93 (d, J=7.5 Hz, 3H, Me-11), 1.10 (s, 3H, Me), 2.64 (d, J=13.5 Hz, 1H, C—CH$_2$-Ph), 2.72 (m, 1H, H-6), 2.84 (d, J=12.6 Hz, 1H, C—CH$_2$-Ph), 2.89 (m, 1H, H-6), 6.75 (d, J=8.5 Hz, 2H, Ar), 7.18 (d, J=8.5 Hz, 2H, Ar), 7.51 (m, 3H, Ar).

Preparation of Compound 29

Compound 29 was prepared using the same method described for compound 24. Methanol was used in addition to hexanes-ethyl acetate mixture during chromatography (2% in volume). Compound 28 (144 mg, 0.359 mmol) gave compound 29 (92 mg, 48%). $^1$H NMR (400 MHz, CDCl$_3$) δ: 0.93 (d, J=7.5 Hz, 3H, Me-11), 1.10 (s, 3H, Me), 2.64 (d, J=13.5 Hz, 1H, C—CH$_2$-Ph), 2.86 (m, 2H, H-6), 2.98 (d, J=13.4 Hz, 1H, C—CH$_2$-Ph), 7.22 (m, 2H, Ar), 7.31 (d, J=8.2 Hz, 1H, Ar), 7.40 (m, 4H, Ar).

Preparation of EM-8791

Under an argon atmosphere, a suspension of compound 29 (60 mg, 0.11 mmol), zinc cyanide (26 mg, 0.22 mmol) and tetrakis(triphenylphosphine)palladium (21 mg, 0.018 mmol) in DMF (bubbled with argon, 2.5 mL) was bubbled with argon for 10 min and heated at 120° C. for 5 h (two additional portions of palladium catalyst was added during the course of the reaction). The reaction mixture was cooled at room temperature and concentrated. The crude product was two times chromatographed (toluene-ethyl acetate/9:1 to toluene-ethyl acetate/17:3) to give EM-8791 (41 mg, 89%). $^1$H NMR (400 MHz, acetone-d$_6$) δ: 0.93 (d, J=7.5 Hz, 3H, Me-11), 1.11 (s, 3H, Me), 2.80-3.05 (m, 4H, C—CH$_2$-Ph, H-6), 7.47 (s, 1H, Ar), 7.50 (m, 2H, Ar), 7.63 (d, J=8.3 Hz, 2H, Ar), 7.66 (d, J=8.3 Hz, 2H, Ar).

Example 5

Synthesis of EM-5987

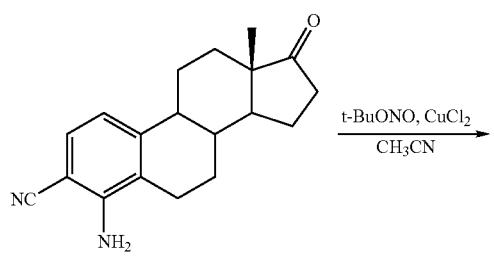

Scheme 5

5

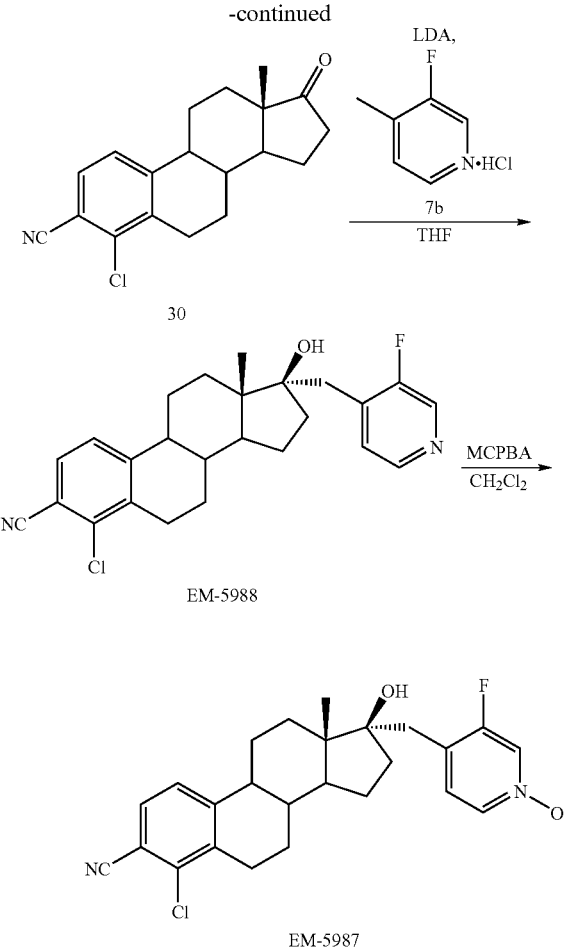

Preparation of Compound 30

In a 100 mL round-bottom flask equipped with a magnetic stirrer, under an argon atmosphere, was placed crude compound 5 (1.0 g, 3.4 mmol), cupric chloride (0.55 g, 4.1 mmol) and 25 mL of dry acetonitrile. The mixture was stirred at 0° C., and tert-butyl nitrite (0.6 mL, 5.1 mmol) was added dropwise. After 25 min, a 10% aqueous hydrochloric acid solution (20 mL) was poured in the reaction. The mixture was then extracted with ethyl acetate (3×75 mL), and the combined organic phase was successively washed with 10% aqueous hydrochloric acid solution (100 mL), water (100 mL) and brine (100 mL). The solution was dried over magnesium sulfate and evaporated in vacuo to provide 0.94 g of compound 30 contaminated with 12% molar of compound 41. $^1$H NMR (400 MHz, CDCl$_3$) δ: 0.91 (s, 3H, Me), 2.53 (m, 1H, H-16), 2.78 (m, 1H, H-6), 3.07 (m, 1H, H-6), 7.33 (d, J=8.2 Hz, 1H, H-1), 7.49 (d, J=8.2 Hz, 1H, H-2).

Preparation of EM-5988

EM-5988 was prepared from the hydrochloride salt of picoline 7b (752 mg, 5.12 mmol) and compound 30 (400 mg, 1.28 mmol) using the procedure described for EM-8455. The crude compound was purified by flash chromatography (silica gel, 0-60% acetone in hexanes) to give 434 mg (79%) of EM-5988. $^1$H NMR (300 MHz, CDCl$_3$) δ: 0.96 (s, 3H, Me), 2.77 (m, 2H —CH$_2$-Ph, H-6), 2.98 (m, 2H, —CH$_2$-Ph, H-6), 7.36 (m, 2H, Ar, Pyr), 7.49 (d, J=8.1 Hz, 1H, Ar), 8.34 (d, J=4.8 Hz, 1H, Pyr), 8.44 (s, 1H, Pyr).

Preparation of EM-5987

EM-5987 was prepared from EM-5988 (200 mg, 0.47 mmol) using the procedure described for EM-5854 to give 192 mg (93%) of EM-5987. $^1$H NMR (300 MHz, CDCl$_3$) δ: 0.95 (s, 3H, Me), 2.73 (m, 2H —CH$_2$-Ph, H-6), 2.98 (m, 2H, —CH$_2$-Ph, H-6), 7.33 (d, J=8.2 Hz, 1H, Ar), 7.46 (m, 2H, Ar, Pyr), 8.01 (d, J=6.6 Hz, 1H, Pyr), 8.16 (d, J=6.4 Hz, 1H, Pyr).

Example 6

Synthesis of EM-5945 and Derivatives

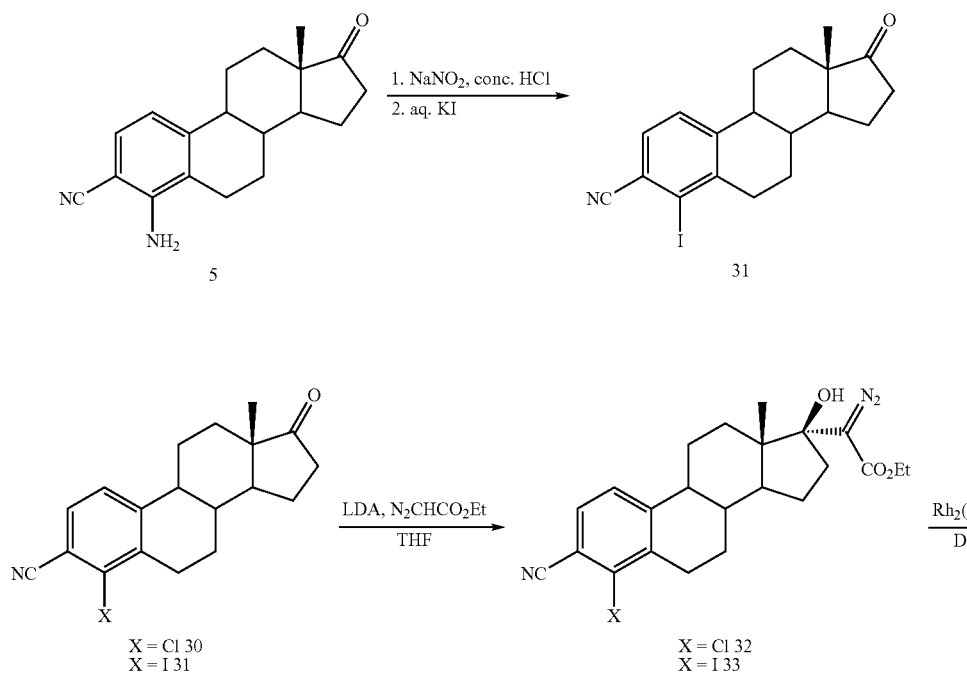

-continued
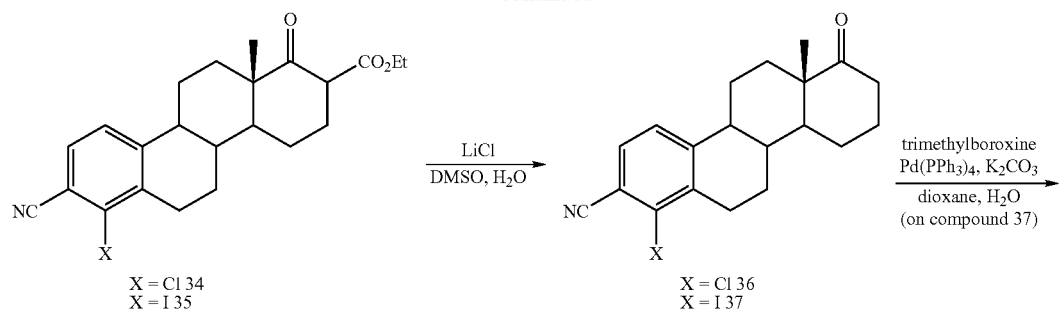
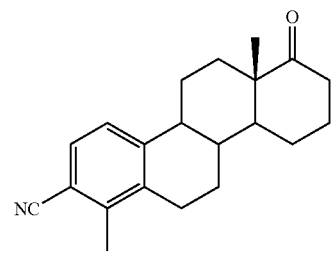
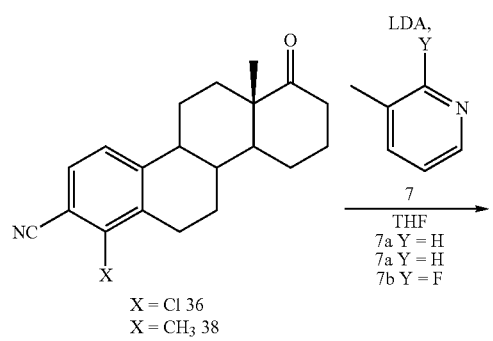
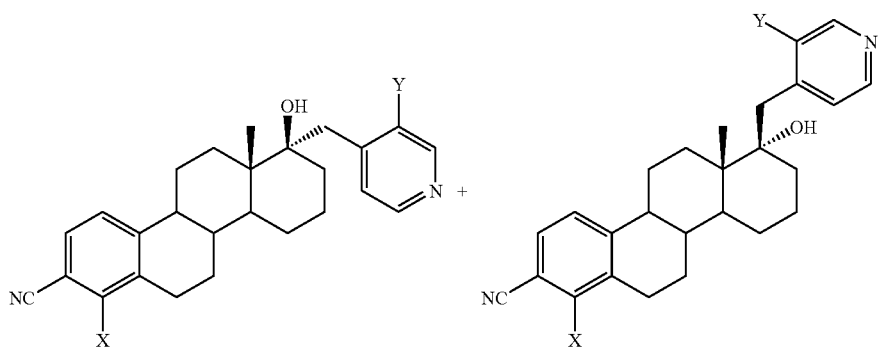

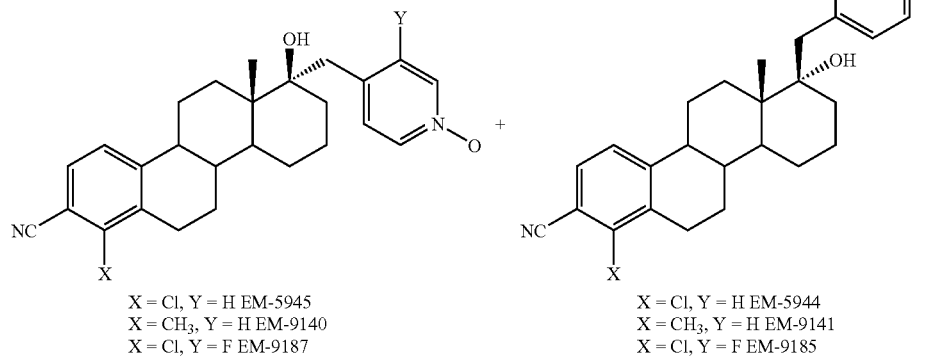

X = Cl, Y = H EM-5945
X = CH₃, Y = H EM-9140
X = Cl, Y = F EM-9187

X = Cl, Y = H EM-5944
X = CH₃, Y = H EM-9141
X = Cl, Y = F EM-9185

Preparation of Compound 31

To an ice-cooled solution of 4-aminosteroid 5 (6.40 g, 21.7 mmol) in concentrated HCl (50 mL) was added a solution of sodium nitrite (1.94 g, 28.2 mmol) in water (7 mL) over a 10 min period. After 20 min of vigorous agitation, a solution of potassium iodide (10.80 g, 65.10 mmol) in water (7 mL) was added dropwise. The resulting slurry was stirred for 10 min at the same temperature before addition of acetone (10 mL), then allowed to reach room temperature. After dilution with ethyl acetate, the organic phase was washed with 20% sodium bisulfite and brine, then dried over sodium sulfate. After concentration, the resulting solid was purified by flash chromatography eluting with 5% ethyl acetate-toluene giving 4-iodosteroid 31 (5.27 g, 60%) as a beige solid which contains 5-10% of compound 41. Compound 31 was used directly for the next step. An analytical sample of compound 31 was obtained by recrystallization from dichloromethane-hexanes. $^1$H NMR (400 MHz, CDCl$_3$) δ: 0.91 (s, 3H, Me), 2.76 (m, 1H, H-6), 2.93 (m, 1H, H-6), 7.41 (s, 2H, H-1 and H-2).

Preparation of Compound 32

A commercial solution of LDA (1.8 M in THF, 21.3 mL, 38.3 mmol) was added to a cooled (−78° C.) solution of 4-chlorosteroid 30 (3.00 g, 9.57 mmol) and ethyl diazoacetate (4.02 mL, 38.3 mmol) in THF (100 mL). The resulting brown reaction mixture was stirred for 3 h at the same temperature after which a solution of saturated ammonium chloride was added; the mixture was then allowed to warm to room temperature. Water was added, the aqueous solution was extracted with ethyl acetate. The combined organic phase was washed with brine then dried over sodium sulfate, and the solvent evaporated. Flash chromatography of the residue with 1% ethyl acetate-toluene give α-diazo-β-hydroxy ester 32 (3.25 g, 79%) as a yellow solid. $^1$H NMR (400 MHz, CDCl$_3$) δ: 0.96 (s, 3H, Me), 1.32 (t, J=7.1 Hz, 3H, —CH$_2$—CH$_3$), 2.75 (m, 1H, H-6), 2.97 (m, 1H, H-6), 4.27 (q, J=7.3 Hz, 2H, —O—CH$_2$—), 4.7 (bs, 1H, OH), 7.30 (d, J=8.1 Hz, 1H, Ar), 7.47 (d, J=8.1 Hz, 1H, Ar).

Preparation of Compound 34

A mixture of the α-diazo-β-hydroxy ester 32 (3.40 g, 7.96 mmol) and a catalytic amount of rhodium(II) acetate dimer (5 mg) in 1,2-dimethoxyethane was stirred for 2 h. The solvent was evaporated and the obtained residue was filtered through silica gel with 10% ethyl acetate-toluene to give the β-ketoester 34 (2.60 g, 82%) as a white solid. $^1$H NMR (400 MHz, CDCl$_3$) (2:3 mixture of tautomers) δ: 1.13 and 1.17 (2s, 3H, Me), 1.29 and 1.31 (2t, J=7.1 Hz, 3H, —CH$_2$—CH$_3$), 2.74 (m, 1H, H-6), 3.02 (m, 1H, H-6), 3.76 (m, 0.4H, H-16), 4.23 (q, J=7.3 Hz, 2H, —O—CH$_2$—), 7.35 (d, J=8.1 Hz, 1H, Ar), 7.49 (d, J=8.1 Hz, 1H, Ar), 12.47 (s, 0.6H, OH enol).

Preparation of Compound 36

The β-ketoester 34 (2.60 g, 6.59 mmol) was heated with lithium chloride (363 mg, 8.56 mmol) in 90% aqueous DMSO (50 mL) at 150° C. for 5 h. After cooling to room temperature, the mixture was poured into water. The precipitate was filtered, washed with water, and dried to furnish D-homosteroid 36 (2.08 g, 96%) as a white solid. $^1$H NMR (400 MHz, CDCl$_3$) δ: 1.13 (s, 3H, Me), 2.69 (m, 2H, H-6 and H-16), 3.03 (m, 1H, H-6), 7.34 (d, J=8.1 Hz, 1H, Ar), 7.48 (d, J=8.1 Hz, 1H, Ar).

Preparation of Compound 33

Alkylation of 4-iodosteroid 31 (1.37 g, 3.38 mmol) with ethyl diazo(lithio)acetate (10.15 mmol) was achieved as reported for the preparation of compound 32 giving α-diazo-β-hydroxy ester 33 (1.24 g, 70%) as a yellow solid. $^1$H NMR (400 MHz, CDCl$_3$) δ: 0.95 (s, 3H, Me), 1.32 (t, J=7.1 Hz, 3H, —CH$_2$—CH$_3$), 2.69 (m, 1H, H-6), 2.91 (m, 1H, H-6), 4.22 (q, J=7.3 Hz, 2H, —O—CH$_2$—), 4.76 (bs, 1H, OH), 7.41 (s, 2H, Ar).

Preparation of Compound 35

Conversion of α-diazo-β-hydroxy ester 33 to β-ketoester 35 (white solid) with rhodium(II) acetate dimer was achieved as described for the preparation of compound 34. $^1$H NMR (400 MHz, CDCl$_3$) (2:3 mixture of tautomers) δ: 1.13 and 1.17 (2s, 3H, Me), 1.30-1.31 (2t, J=7.1 Hz, 3H, —CH$_2$—CH$_3$), 2.72 (m, 1H, H-6), 2.92 (m, 1H, H-6), 3.75 (m, 0.4H, H-16), 4.23 (q, J=7.3 Hz, 2H, —O—CH$_2$—), 7.41 (s, 2H, Ar), 12.47 (s, 0.6H, OH enol).

Preparation of Compound 37

Decarboethoxylation of compound 35 (491 mg, 2.39 mmol) was achieved as described for preparation of 4-chloro derivative 36. The crude 4-iodo-D-homosteroid 37 which contains 10% of 3-cyano-D-homoestrone was recrystallized from 20% methanol-dichloromethane to furnish pure compound 37 (688 mg, 69% yield for 2 steps) as a white solid. $^1$H NMR (400 MHz, CDCl$_3$) δ: 1.12 (s, 3H, Me), 2.72 (m, 2H, H-6 and H-16), 2.92 (m, 1H, H-6), 7.40 (d, J=8.2 Hz, 1H, Ar), 7.43 (d, J=8.2 Hz, 1H, Ar).

Preparation of Compound 38

To a suspension of 4-iodo D-homosteroid 37 (253 mg, 0.603 mmol) and potassium carbonate (250 mg, 1.80 mmol) in 10% water-dioxane (3 mL) was added trimethylboroxine (83 μL, 0.60 mmol). Argon was bubbled through the mixture for 10 min before adding tetrakis(triphenylphosphine)palladium (69 mg, 0.060 mmol). After heating at 100-105° C. for 17 h, the reaction mixture was allowed to cool to room temperature, diluted with ethyl acetate, and filtered through a pad of celite. Concentration and flash chromatography of the residue with 5% ethyl acetate-hexanes containing 5% of dichloromethane gave 4-methyl D-homosteroid 38 (160 mg, 87%) as a white solid. $^1$H NMR (400 MHz, CDCl$_3$) δ: 1.12 (s, 3H, Me), 1.55 (s, 3H, Me), 2.69 (m, 2H, H-6 and H-16), 2.82 (m, 1H, H-6), 7.27 (d, J=8.2 Hz, 1H, Ar), 7.42 (d, J=8.2 Hz, 1H, Ar).

Preparation of EM-5942, EM-5943, EM-9143, EM-9139, EM-9188 and EM-9189

D-homosteroids 36 and 38 were alkylated with 7a or 7b according to the preparation of EM-5854 giving a 3:2 mixture of 17-α and 17-β regioisomers. In both cases, the regioisomers were separated by flash chromatography eluting with 1% methanol-dichloromethane.

EM-5942 (17-β), (22 mg, 22%), white solid. $^1$H NMR (400 MHz, CDCl$_3$) δ: 1.02 (s, 3H, Me), 2.52 (d, J$_{gem}$=12.8 Hz, 1H, —CH$_2$-Pyr), 2.71 (m, 1H, H-6), 3.01 (d, J$_{gem}$=12.6 Hz, 1H, —CH$_2$-Pyr), 3.02 (m, 1H, H-6), 7.15 (d, J=5.7 Hz, 2H, Pyr), 7.34 (d, J=8.3 Hz, 1H, Ar), 7.48 (d, J=8.4 Hz, 1H, Ar), 8.51 (d, J=5.8 Hz, 2H, Pyr); MS (APCI+) m/z 421 (M+H, 45).

EM-5943 (17-α), (44 mg, 34%), white solid. $^1$H NMR (400 MHz, CDCl$_3$) δ: 1.04 (s, 3H, Me), 2.76 (m, 1H, H-6), 2.99 (s, 2H, —CH$_2$-Pyr), 3.02 (m, 1H, H-6), 7.26 (m, 2H, Pyr), 7.36 (d, J=8.1 Hz, 1H, Ar), 7.48 (d, J=8.2 Hz, 1H, Ar), 8.51 (d, J=5.4 Hz, 2H, Pyr).

EM-9143 (17-β), (95 mg, 21%), white solid. $^1$H NMR (400 MHz, CDCl$_3$) δ: 1.03 (s, 3H, Me), 2.43 (s, 3H, Me), 2.58 (d, J$_{gem}$=12.9 Hz, 1H, —CH$_2$-Pyr), 2.64 (m, 1H, H-6), 2.79 (m, 1H, H-6), 3.01 (d, J$_{gem}$=12.6 Hz, 1H, —CH$_2$-Pyr), 7.15 (d, J=5.7 Hz, 2H, Pyr), 7.27 (d, J=8.3 Hz, 1H, Ar), 7.42 (d, J=8.4 Hz, 1H, Ar), 8.52 (d, J=5.5 Hz, 2H, Pyr).

EM-9139 (17-α), (100 mg, 22%), white solid. $^1$H NMR (400 MHz, CDCl$_3$) δ: 1.04 (s, 3H, Me), 2.43 (s, 3H, Me), 2.66 (m, 1H, H-6), 2.80 (m, 1H, H-6), 3.00 (s, 2H, —CH$_2$-Pyr), 7.26 (m, 2H, Pyr), 7.27 (d, J=8.1 Hz, 1H, Ar), 7.43 (d, J=8.2 Hz, 1H, Ar), 8.51 (dd, J=1.3 and 4.6 Hz, 2H, Pyr).

EM-9188 (17-β), (42 mg, 15%), white solid. $^1$H NMR (400 MHz, CDCl$_3$) δ: 1.06 (s, 3H, Me), 2.71 (m, 1H, H-6), 2.83 (d, J$_{gem}$=12.9 Hz, 1H, —CH$_2$-Pyr), 2.95 (d, J$_{gem}$=12.9 Hz, 1H, —CH$_2$-Pyr), 3.00 (m, 1H, H-6), 7.21 (dd, J=5.2 and 5.9 Hz, 1H, Pyr), 7.35 (d, J=8.1 Hz, 1H, Ar), 7.48 (d, J=8.2 Hz, 1H, Ar), 8.34 (d, J=4.8 Hz, 1H, Pyr), 8.41 (s, 1H, Pyr).

EM-9189 (17-α), (86 mg, 32%), white solid. $^1$H NMR (400 MHz, CDCl$_3$) δ: 1.04 (s, 3H, Me), 2.76 (m, 1H, H-6), 2.92 (d, J$_{gem}$=13.5 Hz, 1H, —CH$_2$-Pyr), 3.02 (m, 1H, H-6), 3.25 (d, J$_{gem}$=13.5 Hz, 1H, —CH$_2$-Pyr), 7.35 (d, J=8.3 Hz, 1H, Ar), 7.40 (dd, J=5.4 and 5.8 Hz, 1H, Pyr), 7.48 (d, J=8.2 Hz, 1H, Ar), 8.33 (d, J=4.7 Hz, 1H, Pyr), 8.42 (s, 1H, Pyr).

Preparation of EM-5944, EM-5945, EM-9141, EM-9140, EM-9185 and EM-9187

All these compounds were prepared from the corresponding pyridines according to the preparation of EM-5855. In both cases, crude material was triturated in acetone to give pure pyridine N-oxides as white solids.

EM-5944 (17-β, (100 mg, 83%). $^1$H NMR (400 MHz, DMSO-d$_6$) δ: 0.92 (s, 3H, Me), 2.55 (d, J$_{gem}$=12.8 Hz, 1H, —CH$_2$-Pyr), 2.71 (m, 1H, H-6), 2.82 (d, J$_{gem}$=12.8 Hz, 1H, —CH$_2$-Pyr), 2.98 (m, 1H, H-6), 7.22 (d, J=6.9 Hz, 2H, Pyr), 7.52 (d, J=8.1 Hz, 1H, Ar), 7.72 (d, J=8.1 Hz, 1H, Ar), 8.08 (d, J=6.6 Hz, 2H, Pyr); MS (APCI+) m/z 437 (M+H, 100).

EM-5945 (17-α, (186 mg, 86%). $^1$H NMR (400 MHz, CDCl$_3$) δ: 1.03 (s, 3H, Me), 2.75 (m, 1H, H-6), 2.77 (dd, J=6.8 and 11.3 Hz, 1H, H-6), 3.00 (s, 2H, —CH$_2$-Pyr), 7.26 (m, 2H, Pyr), 7.35 (d, J=8.1 Hz, 1H, Ar), 7.48 (d, J=8.2 Hz, 1H, Ar), 8.12 (d, J=6.9 Hz, 2H, Pyr); MS (APCI+) m/z 437 (M+H, 50).

EM-9141 (17-β, (48 mg, 62%). $^1$H NMR (400 MHz, CDCl$_3$) δ: 1.01 (s, 3H, Me), 2.43 (s, 3H, Me), 2.56 (d, J$_{gem}$=13.2 Hz, 1H, —CH$_2$-Pyr), 2.64 (m, 1H, H-6), 2.79 (m, 1H, H-6), 3.02 (d, J$_{gem}$=13.1 Hz, 1H, —CH$_2$-Pyr), 7.16 (d, J=6.8 Hz, 2H, Pyr), 7.28 (d, J=8.3 Hz, 1H, Ar); 7.42 (d, J=8.4 Hz, 1H, Ar), 8.12 (d, J=6.8 Hz, 2H, Pyr).

EM-9140 (17-α), (60 mg, 55%). $^1$H NMR (400 MHz, CDCl$_3$) δ: 1.03 (s, 3H, Me), 2.43 (s, 3H, Me), 2.65 (m, 1H, H-6), 2.81 (m, 1H, H-6), 2.98 (s, 2H, —CH$_2$-Pyr), 7.28 (m, 3H, Ar, Pyr), 7.43 (d, J=8.2 Hz, 1H, Ar), 8.12 (d, J=6.9 Hz, 2H, Pyr).

EM-9185 (17-β), (9.1 mg, 45%). $^1$H NMR (400 MHz, CDCl$_3$) δ: 1.04 (s, 3H, Me), 2.75 (m, 1H, H-6), 2.78 (d, J$_{gem}$=13.2 Hz, 1H, —CH$_2$-Pyr), 2.90 (d, J$_{gem}$=13.4 Hz, 1H, —CH$_2$-Pyr), 3.01 (m, 1H, H-6), 7.22 (dd, J=6.8 and 8.4 Hz, 1H, Pyr), 7.34 (d, J=8.3 Hz, 1H, Ar), 7.48 (d, J=8.2 Hz, 1H, Ar), 7.99 (dd, J=1.0 and 6.7 Hz, 1H, Pyr), 8.11 (dd, J=1.5 and 4.9 Hz, 1H, Pyr).

EM-9187 (17-α), (27 mg, 71%). $^1$H NMR (400 MHz, CDCl$_3$) δ: 1.03 (s, 3H, Me), 2.71 (m, 1H, H-6), 2.86 (d, J$_{gem}$=13.8 Hz, 1H, —CH$_2$-Pyr), 3.01 (m, 1H, H-6), 3.21 (d, J$_{gem}$=13.9 Hz, 1H, —CH$_2$-Pyr), 7.35 (d, J=8.3 Hz, 1H, Ar), 7.40 (dd, J=7.3 and 8.4 Hz, 1H, Pyr), 7.49 (d, J=8.2 Hz, 1H, Ar), 7.99 (dd, J=1.2 and 6.7 Hz, 1H, Pyr), 8.13 (dd, J=1.5 and 5.4 Hz, 1H, Pyr).

Example 7

Synthesis of EM-5985

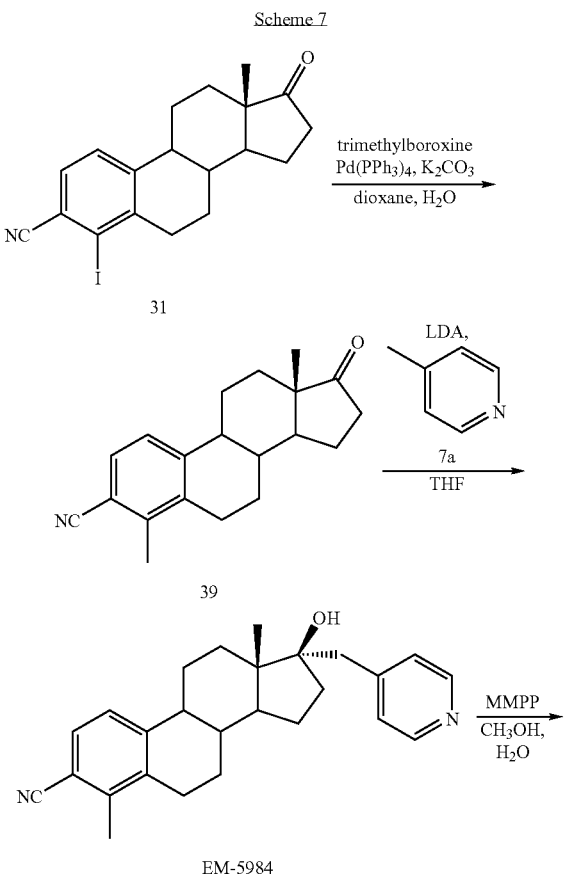

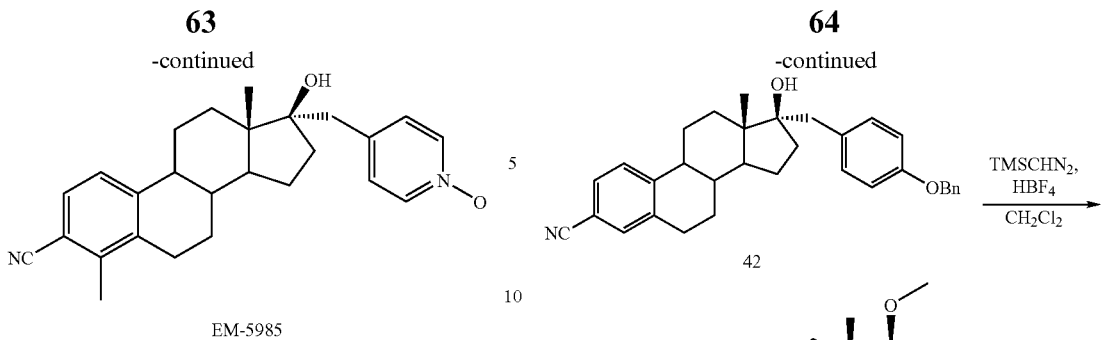

EM-5985

Preparation of Compound 39

Methylation of 4-iodosteroid 31 was carried out as reported for preparation of compound 38. The crude product was purified by flash chromatography with 10% ethyl acetate-hexanes containing 10% of dichloromethane to give compound 39 (535 mg, 87% yield) as an off-white solid. $^1$H NMR (400 MHz, CDCl$_3$) δ: 0.91 (s, 3H, Me), 2.55 (s, 3H, Me), 2.75 (m, 2H, H-6 and H-16), 2.87 (m, 1H, H-6), 7.28 (d, J=8.2 Hz, 1H, Ar), 7.43 (d, J=8.4 Hz, 1H, Ar).

Preparation of EM-5984 and EM-5985

Alkylation of 39 with 7a and subsequent oxidation with magnesium monoperoxyphthalate were achieved according to the preparation of EM-5855 and EM-9103.

EM-5984 (145 mg, 50%), white solid. $^1$H NMR (400 MHz, acetone-d$_6$) δ: 0.97 (s, 3H, Me), 2.41 (s, 3H, Me), 2.65 (m, 1H, H-6), 2.76 (d, J$_{gem}$=13.3 Hz, 1H, —CH$_2$-Pyr), 2.81-2.85 (m, 1H, H-6), 2.88 (d, J$_{gem}$=13.5 Hz, 1H, —CH$_2$-Pyr), 7.36 (d, J=5.8 Hz, 2H, Pyr), 7.40 (d, J=8.2 Hz, 1H, Ar), 7.48 (d, J=8.2 Hz, 1H, Ar), 8.45 (d, J=5.8 Hz, 2H, Pyr).

EM-5985 (79 mg, 86%), white solid. $^1$H NMR (400 MHz, CDCl$_3$) δ: 0.94 (s, 3H, Me), 2.41 (s, 3H, Me), 2.60 (d, J$_{gem}$=13.4 Hz, 1H, —CH$_2$-Pyr), 2.65 (m, 1H, H-6), 2.92 (m, 1H, H-6), 2.95 (d, J$_{gem}$=13.5 Hz, 1H, —CH$_2$-Pyr), 7.27 (m, 3H, Ar, Pyr), 7.41 (d, J=8.1 Hz, 1H, Ar), 8.04 (d, J=6.1 Hz, 2H, Pyr); MS (APCI+) m/z 403 (M+H, 100).

Example 8

Synthesis of EM-4350 and EM-5292

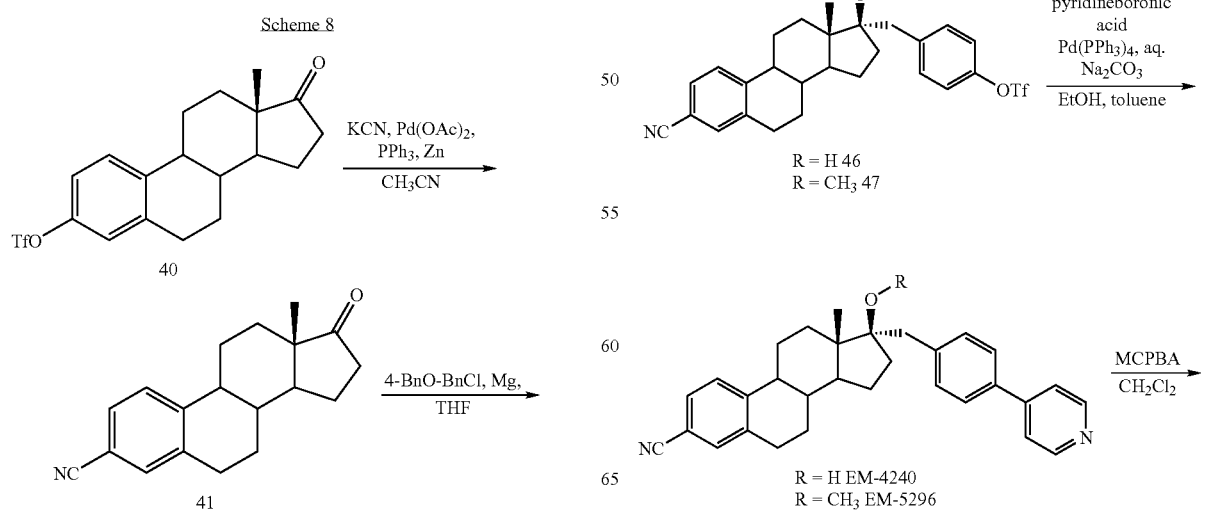

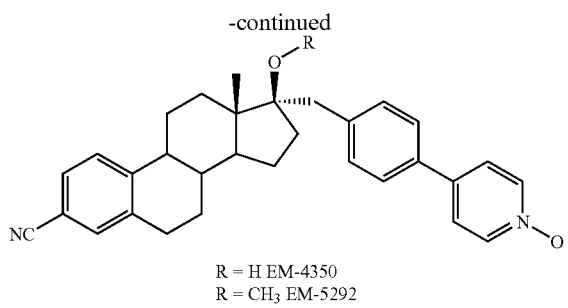

R = H EM-4350
R = CH₃ EM-5292

Preparation of compound 41

In a dry 5 L three-neaked round-bottom flask equipped with a condenser, compound 40 (172 g, 0.428 mol) (from Labrie, F., Provencher, L., Gauthier, S. WO 2004/089971) was solubilized in 2.9 L of deoxygenated acetonitrile under an argon atmosphere. To that solution was added palladium (II) acetate (9.6 g, 0.043 mol) and triphenylphosphine (44.9 g, 0.171 mol). The reaction mixture was stirred and heated until every reagents were solubilized, then activated zinc (16.8 g, 0.257 mol) was added portionwise. The mixture was heated at reflux for 15 min where a dark coloration can be observed, then potassium cyanide (41.7 g, 0.642 mol) was added by portion. The reaction mixture was kept heated at reflux for 1.5 h. The solvent was evaporated, dichloromethane (2 L) was added, and the mixture was stirred for 2 h. The resulting suspension was filtered under vacuum and the solvent was evaporated. The reaction was done three times to give 550 g of the crude residue which was triturated from methanol (3 L) for 4 h. The resulting grey solid was filtered and recrystallized from hot chloroform (1.6 L): methanol (1.6 L) at 4° C. to provide 294 g (84%, HPLC 99.5%) of compound 41 as grey-white crystals. $^1$H NMR (400 MHz, CDCl₃) δ: 0.92 (s, 3H, Me), 1.49-1.64 (m, 6H), 1.98-2.54 (m, 7H), 2.94 (m, 2H, H-6), 7.41 (m, 3H, Ar).

Preparation of Compound 42

Compound 42 was prepared from compound 41 (300 mg, 1.07 mmol) using the procedure described for compound 11 to give 333 mg (65%) of compound 42. $^1$H NMR (400 MHz, acetone-d₆) δ: 0.99 (s, 3H, Me), 2.69 (d, $J_{gem}$=13.5 Hz, 1H, C—CH₂-Ph), 2.87 (d, $J_{gem}$=13.5 Hz, 1H, C—CH₂-Ph), 2.94 (m, 2H, H-6), 5.11 (s, 2H, O—CH₂-Ph), 6.93 (d, J=8.5 Hz, 2H, Ar), 7.29 (d, J=8.5 Hz, 2H, Ar), 7.34 (d, J=7.3 Hz, 1H, Ar), 7.41 (t, J=7.2 Hz, 2H, Ar), 7.51 (m, 5H, OBn).

Preparation of Compound 43

To a solution of compound 42 (250 mg, 0.52 mmol) in anhydrous dichloromethane (4 mL) at 0° C. was added tetrafluoroboric acid (48% in H₂O, 142 μL, 0.78 mmol). Then, trimethylsilyldiazomethane (2.0 M in hexanes, 1.04 mL, 2.08 mmol) was added in 20 min intervals in four portions. An excess of trimethylsilyldiazomethane was added to complete the reaction. Silica gel was added to destroy the excess of trimethylsilyldiazomethane. The reaction was quenched with aqueous saturated sodium bicarbonate, filtered, and concentrated under reduced pressure. The mixture was extracted with dichloromethane (3×). The combined organic layer was washed with water and brine, dried over MgSO₄, filtered, and concentrated under reduced pressure. The crude compound was purified by flash chromatography (silica gel, 0-20% ethyl acetate in hexanes) to give 96 mg (37%) of compound 43. $^1$H NMR (400 MHz, acetone-d₆) δ: 0.99 (s, 3H, Me), 2.64 (d, $J_{gem}$=13.2 Hz, 1H, C—CH₂-Ph), 2.95 (m, 2H, H-6), 3.36 (d, $J_{gem}$=13.5 Hz, 1H, C—CH₂-Ph), 3.38 (s, 3H, OMe), 5.11 (s, 2H, O—CH₂-Ph), 6.95 (d, J=8.7 Hz, 2H, Ar), 7.24 (d, J=8.6 Hz, 2H, Ar), 7.34 (d, J=7.3 Hz, 1H, Ar), 7.41 (t, J=7.1 Hz, 2H, Ar), 7.51 (m, 5H, OBn).

Preparation of Compound 44

To a solution of compound 42 (1.09 g, 2.28 mmol) in anhydrous dichloromethane (100 mL) at −78° C. was added boron trichloride (1.0 M in dichloromethane, 6.9 mL, 6.9 mmol). The mixture was stirred at 0° C. for 1 h. After completion (TLC), the reaction was quenched with aqueous saturated sodium bicarbonate. The mixture was extracted with dichloromethane (3×). The combined organic layer was washed with aqueous saturated sodium bicarbonate and brine, dried over MgSO₄, filtered, and concentrated under reduced pressure. The crude compound was purified by flash chromatography (silica gel, 0-100% acetone in hexanes) to give 513 mg (60%) of compound 44. $^1$H NMR (400 MHz, CDCl₃) δ: 0.97 (s, 3H, Me), 2.61 (d, $J_{gem}$=13.6 Hz, 1H, C—CH₂-Ph), 2.88 (m, 3H, C—CH₂-Ph, H-6), 6.79 (d, J=8.4 Hz, 2H, Ar), 7.12 (d, J=8.4 Hz, 2H, Ar), 7.37 (m, 3H, Ar).

Alternative Procedure:

A mixture of compound 42 (4.0 g, 8.3 mmol) and palladium (10 wt. % on activated carbon, 300 mg) in ethyl acetate-methanol/3:1 (120 mL) was stirred under hydrogen (1 atm) at 22° C. for 16 h. After completion of the reaction (TLC), the mixture was filtered through celite and washed several times with ethyl acetate. The solvent was removed under reduced pressure. The crude compound was purified by flash chromatography (silica gel, 0-20% acetone in toluene) to give 3.03 g (94%) of compound 44.

Preparation of Compound 45

Compound 45 was prepared from compound 43 (738 mg, 1.50 mmol) using the first procedure described for compound 12. The crude compound was purified by flash chromatography (silica gel, 0-100% ethyl acetate in hexanes) to give 339 mg (56%) of compound 45. $^1$H NMR (400 MHz, CDCl₃) δ: 1.01 (s, 3H, Me), 2.51 (d, $J_{gem}$=14.7 Hz, 1H, C—CH₂-Ph), 2.89 (m, 2H, H-6), 3.31 (d, $J_{gem}$=15.1 Hz, 1H, C—CH₂-Ph), 3.38 (s, 3H, OMe), 6.77 (d, J=8.6 Hz, 2H, Ar), 7.15 (d, J=8.6 Hz, 2H, Ar), 7.40 (m, 3H, Ar).

Preparation of Compound 46

Compound 46 was prepared from compound 44 (513 mg, 1.32 mmol) using the procedure described for compound 13. The crude compound was purified by flash chromatography (silica gel, 0-50% ethyl acetate in hexanes) to give 494 mg (72%) of compound 46. $^1$H NMR (400 MHz, CDCl₃) δ: 0.97 (s, 3H, Me), 2.67 (d, $J_{gem}$=13.5 Hz, 1H, C—CH₂-Ph), 2.91 (m, 2H, H-6), 2.96 (d, $J_{gem}$=13.5 Hz, 1H, C—CH₂-Ph), 7.21 (d, J=8.6 Hz, 2H, Ar), 7.40 (m, 5H, Ar).

Preparation of Compound 47

Compound 47 was prepared from compound 45 (555 mg, 1.38 mmol) using the procedure described for compound 13. The crude compound was purified by flash chromatography (silica gel, 0-10% ethyl acetate in hexanes) to give 490 mg (66%) of compound 47. $^1$H NMR (400 MHz, CDCl₃) δ: 1.04 (s, 3H, Me), 2.65 (d, $J_{gem}$=13.2 Hz, 1H, C—CH₂-Ph), 2.92 (m, 2H, H-6), 3.39 (s, 3H, OMe), 3.41 (d, $J_{gem}$=13.5 Hz, 1H, C—CH₂-Ph), 7.22 (d, J=8.6 Hz, 2H, Ar), 7.41 (m, 5H, Ar).

Preparation of EM-4240

A mixture of compound 46 (270 mg, 0.52 mmol), 4-pyridineboronic acid (95 mg, 0.78 mmol), tetrakis(triphenylphosphine)palladium (13 mg, 0.011 mmol) in toluene (0.5 mL) and ethanol (0.5 mL) was purged with argon while stirring for 15 min. Then, an aqueous solution of sodium carbonate (2.0 M, 380 μL, 0.76 mmol) was added, and the mixture was purged with argon for another 10 min. The mixture was stirred for 16 h under reflux. After completion of the reaction, the mixture was diluted with aqueous saturated sodium bicarbonate and extracted with ethyl acetate (3×). The combined organic layer was washed with aqueous saturated sodium bicarbonate and brine, dried over MgSO$_4$, filtered, and concentrated under reduced pressure. The crude compound was purified by flash chromatography (silica gel, 0-10% ethyl acetate in chloroform to 5% methanol in chloroform) to give 193 mg (90%) of EM-4240. $^1$H NMR (400 MHz, CDCl$_3$) δ: 1.02 (s, 3H, Me), 2.76 (d, J$_{gem}$=13.3 Hz, 1H, C—CH$_2$-Ph), 2.94 (m, 2H, H-6), 3.04 (d, J$_{gem}$=13.2 Hz, 1H, C—CH$_2$-Ph), 7.44 (m, 5H, Ar), 7.66 (m, 4H, Ar), 8.68 (d, J=4.9 Hz, 2H, Pyr).

Preparation of EM-5296

EM-5296 was prepared from compound 47 (480 mg, 0.90 mmol) using the procedure described for EM-4240. The crude compound was purified by flash chromatography (silica gel, 10-30% ethyl acetate in hexanes) to give 246 mg (59%) of EM-5296. $^1$H NMR (400 MHz, CDCl$_3$) δ: 1.03 (s, 3H, Me), 2.66 (d, J$_{gem}$=15.2 Hz, 1H, C—CH$_2$-Ph), 2.90 (m, 2H, H-6), 3.42 (s, 3H, OMe), 3.45 (d, J$_{gem}$=15.2 Hz, 1H, C—CH$_2$-Ph), 7.40 (m, 5H, Ar), 7.51 (m, 2H, Pyr), 7.59 (d, J=8.2 Hz, 2H, Ar), 8.65 (bs, 2H, Pyr).

Preparation of EM-4350

EM-4350 was prepared from EM-4240 (193 mg, 0.43 mmol) using the procedure described for EM-5854 to give 120 mg (60%) of EM-4350. $^1$H NMR (400 MHz, CDCl$_3$) δ: 1.01 (s, 3H, Me), 2.75 (d, J$_{gem}$=13.3 Hz, 1H, C—CH$_2$-Ph), 2.95 (m, 2H, H-6), 3.04 (d, J$_{gem}$=13.2 Hz, 1H, C—CH$_2$-Ph), 7.44 (m, 5H, Ar), 7.64 (m, 4H, Ar, Pyr), 8.45 (d, J=6.3 Hz, 2H, Pyr).

Preparation of EM-5292

EM-5292 was prepared from EM-5296 (160 mg, 0.35 mmol) using the procedure described for EM-5854 to give 140 mg (85%) of EM-5292. $^1$H NMR (400 MHz, CDCl$_3$) δ: 1.04 (s, 3H, Me), 2.66 (d, J$_{gem}$=15.2 Hz, 1H, C—CH$_2$-Ph), 2.90 (m, 2H, H-6), 3.42 (s, 3H, OMe), 3.45 (d, J$_{gem}$=15.2 Hz, 1H, C—CH$_2$-Ph), 7.40 (m, 5H, Ar), 7.52 (m, 4H, Ar, Pyr), 8.25 (d, J=7.1 Hz, 2H, Pyr).

Example 9

Synthesis of EM-8912

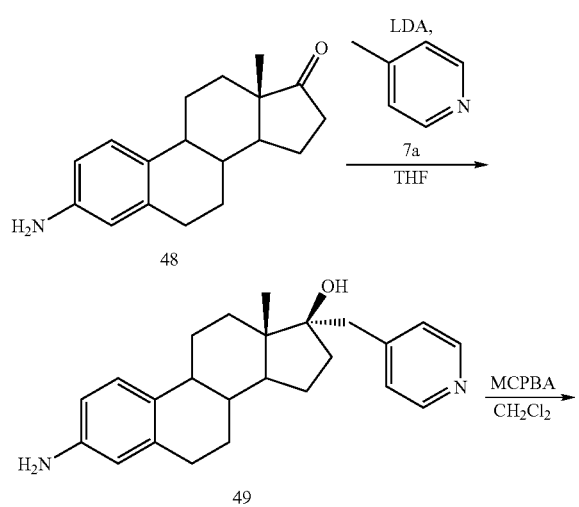

Preparation of Compound 49

3-aminoestrone 48 (294 mg, 1.11 mmol) (from Radu, I.-I., Poirier, D., Provencher, L. Tetrahedron Lett. 2002, 43, 7617) was treated with 7a (5.55 mmol) and LDA (5.44 mmol) at −78° C. then 0° C. for 1 h as described for the preparation of EM-5855. The crude residue was purified by flash chromatography eluting with 20% acetone-hexanes to yield compound 49 (252 mg, 62%) as a beige solid. $^1$H NMR (400 MHz, acetone-d$_6$) δ: 0.97 (s, 3H, Me), 2.71-2.75 (m, 4H, —CH$_2$-Pyr, H-6), 4.21 (bs, 2H, NH$_2$), 6.37 (s, 1H, H-4), 6.39 (d, J=8.3 Hz, 1H, H-2), 6.44 (d, J=8.3 Hz, 1H, H-1), 7.36 (d, J=6.0 Hz, 2H, Pyr), 8.43 (d, J=6.0 Hz, 2H, Pyr).

Preparation of EM-8912

To a stirred solution of 3-chloroperbenzoic acid 70% (1.18 g, 4.80 mmol) in hot dichloromethane (8 mL) was added dropwise, a solution of compound 49 (220 mg, 0.60 mmol) in dichloromethane (20 mL). The resulting brown mixture was refluxed for 1 h, after which the mixture became yellow. After cooling at room temperature and washing with 20% sodium bisulfite, 10% sodium hydroxide, water and brine, the solvent was removed. The resulting solid was triturated in acetone to give EM-8912 as a yellow solid (150 mg, 63%). $^1$H NMR (400 MHz, CDCl$_3$) δ: 0.97 (s, 3H, Me), 2.61 (d, J$_{gem}$=13.6 Hz, 1H, —CH$_2$-Pyr), 2.96 (d, J$_{gem}$=13.6 Hz, 1H, —CH$_2$-Pyr), 3.00 (m, 2H, H-6), 7.29 (d, J=6.9 Hz, 2H, Pyr), 7.44 (d, J=8.6 Hz, 1H, H-1), 7.96 (s, 1H, H-4), 7.99 (d, J=8.5 Hz, 1H, H-2), 8.14 (d, J=7.0 Hz, 2H, Pyr).

Example 10

Synthesis of EM-5628

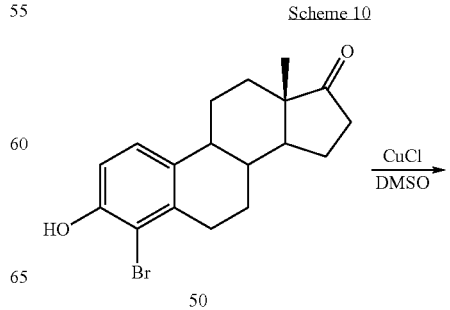

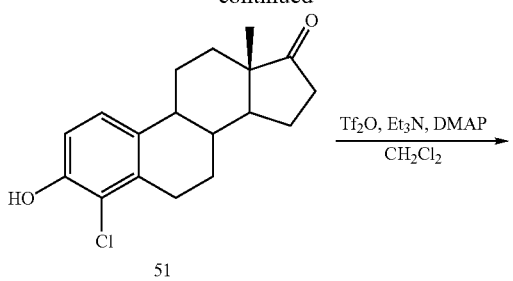

51

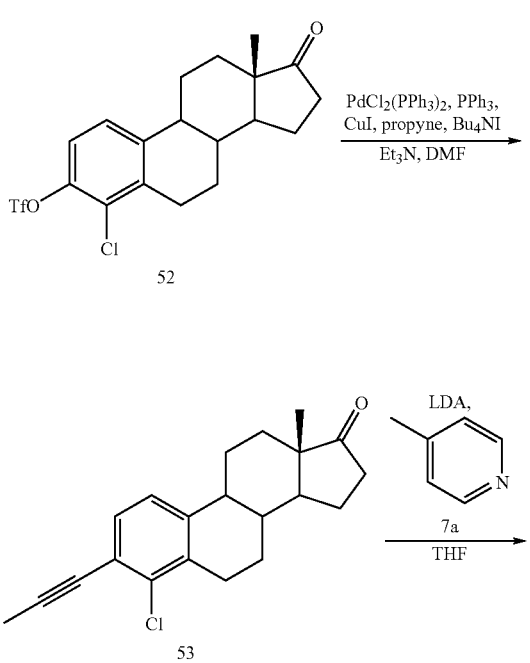

52

53

EM-5607

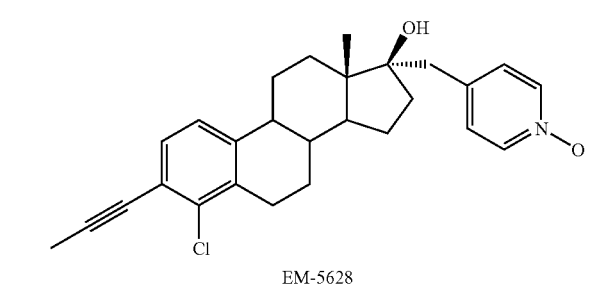

EM-5628

Preparation of Compound 51

A suspension of compound 50 (10.0 g, 28.6 mmol) (from Labrie, F., Provencher, L., Gauthier, S. WO 2004/089971) and copper(1) chloride (28 g, 280 mmol) in DMSO (250 mL) was stirred and heated at 120° C. for 16 h. The reaction mixture was cooled to room temperature, diluted with water and ethyl acetate, and filtered. The organic phase was washed with water (6×) and brine, dried over $MgSO_4$, filtered, and evaporated. The crude product was triturated from methanol to give 6.7 g of desired compound 51. The mother liquors were chromatographed (dichloromethane to dichloromethane-acetone/49:1) to give an additional 1.1 g of compound 51 (7.8 g, 89%). $^1$H NMR (400 MHz, $CDCl_3$) δ: 0.93 (s, 3H, Me), 2.54 (m, 1H, H-16), 2.75 (m, 1H, H-6), 3.01 (m, 1H, H-6), 6.88 (d, J=8.6 Hz, 1H, Ar), 7.17 (d, J=8.5 Hz, 1H, Ar).

Preparation of Compound 52

Compound 52 was prepared using the same method described for compound 3. However, the crude product was chromatographed (hexanes-ethyl acetate/19:1 to hexanes-ethyl acetate/4:1). Compound 51 (7.8 g, 25.6 mmol) gave compound 52 (9.6 g, 86%). $^1$H NMR (300 MHz, $CDCl_3$) δ: 0.91 (s, 3H, Me), 2.52 (m, 1H, H-16), 2.79 (m, 1H, H-6), 3.04 (m, 1H, H-6), 7.15 (d, J=8.7 Hz, 1H, Ar), 7.29 (d, J=8.8 Hz, 1H, Ar).

Preparation of Compound 53

A mixture of compound 52 (800 mg, 1.83 mmol), triphenylphosphine (31 mg, 0.115 mmol), dichlorobis(triphenylphosphine)palladium(II) (64 mg, 0.091 mmol), triethylamine (3.7 mL), tetrabutylammonium iodide (1.35 g, 3.66 mmol) and DMF (2 mL) was added in a Schlenk tube and bubbled with argon for 20 min. The reaction mixture was treated with copper(I) iodide (13 mg, 0.066 mmol), bubbled with argon for 10 min, and treated with a solution of propyne (1 mL) in DMF (4 mL). The Schlenk tube was closed and heated at 95° C. overnight. The reaction mixture was cooled to room temperature, filtered on celite, rinced with ethyl acetate, and concentrated. The residue was chromatographed (hexanes-toluene/99:1 to hexanes-toluene/19:1) and triturated from hexanes-dichloromethane/49:1 to give compound 53 (463 mg, 77%). $^1$H NMR (400 MHz, $CDCl_3$) δ: 0.93 (s, 3H, Me-18), 2.14 (s, 3H, Me), 2.54 (m, 1H, H-16), 2.76 (m, 1H, H-6), 3.04 (m, 1H, H-6), 7.17 (d, J=8.2 Hz, 1H, Ar), 7.28 (d, J=7.7 Hz, 1H, Ar).

Preparation of EM-5607

EM-5607 was prepared using the same method described for EM-5855. The crude product was chromatographed (chloroform-acetone/9:1 to chloroform-acetone/3:2 then chloroform-methanol/19:1 to chloroform-methanol/9:1). Compound 53 (454 mg, 1.39 mmol) gave EM-5607 (314 mg, 54%) (recovered compound 53: 200 mg). $^1$H NMR (400 MHz, $CDCl_3$) δ: 0.98 (s, 3H, Me-18), 2.14 (s, 3H, Me), 2.66 (d, J=13.3 Hz, 1H, $CH_2$-Pyr), 2.75 (m, 1H, H-6), 2.96 (d, J=13.4 Hz, 1H, $CH_2$-Pyr), 3.02 (m, 1H, H-6), 7.19 (d, J=8.1 Hz, 1H, Ar), 7.30 (m, 3H, Ar, Pyr), 8.55 (d, J=5.1 Hz, 2H, Pyr).

Preparation of EM-5628

EM-5628 was prepared using the same method described for EM-5854. The crude product was chromatographed (chloroform-methanol/99:1 to chloroform-methanol/9:1) and triturated from hexanes-acetone/4:1. EM-5607 (290 mg, 0.69 mmol) gave EM-5628 (260 mg, 86%). $^1$H NMR (400 MHz, $CDCl_3$) δ: 0.97 (s, 3H, Me-18), 2.14 (s, 3H, Me), 2.63 (d, J=13.6 Hz, 1H, $CH_2$-Pyr), 2.75 (m, 1H, H-6), 2.96 (d, J=13.7 Hz, 1H, CH$_2$-Pyr), 3.01 (m, 1H, H-6), 7.18 (d, J=8.2 Hz, 1H, Ar), 7.30 (m, 3H, Ar, Pyr), 8.15 (d, J=6.7 Hz, 2H, Pyr).

Example 11

Synthesis of EM-8904

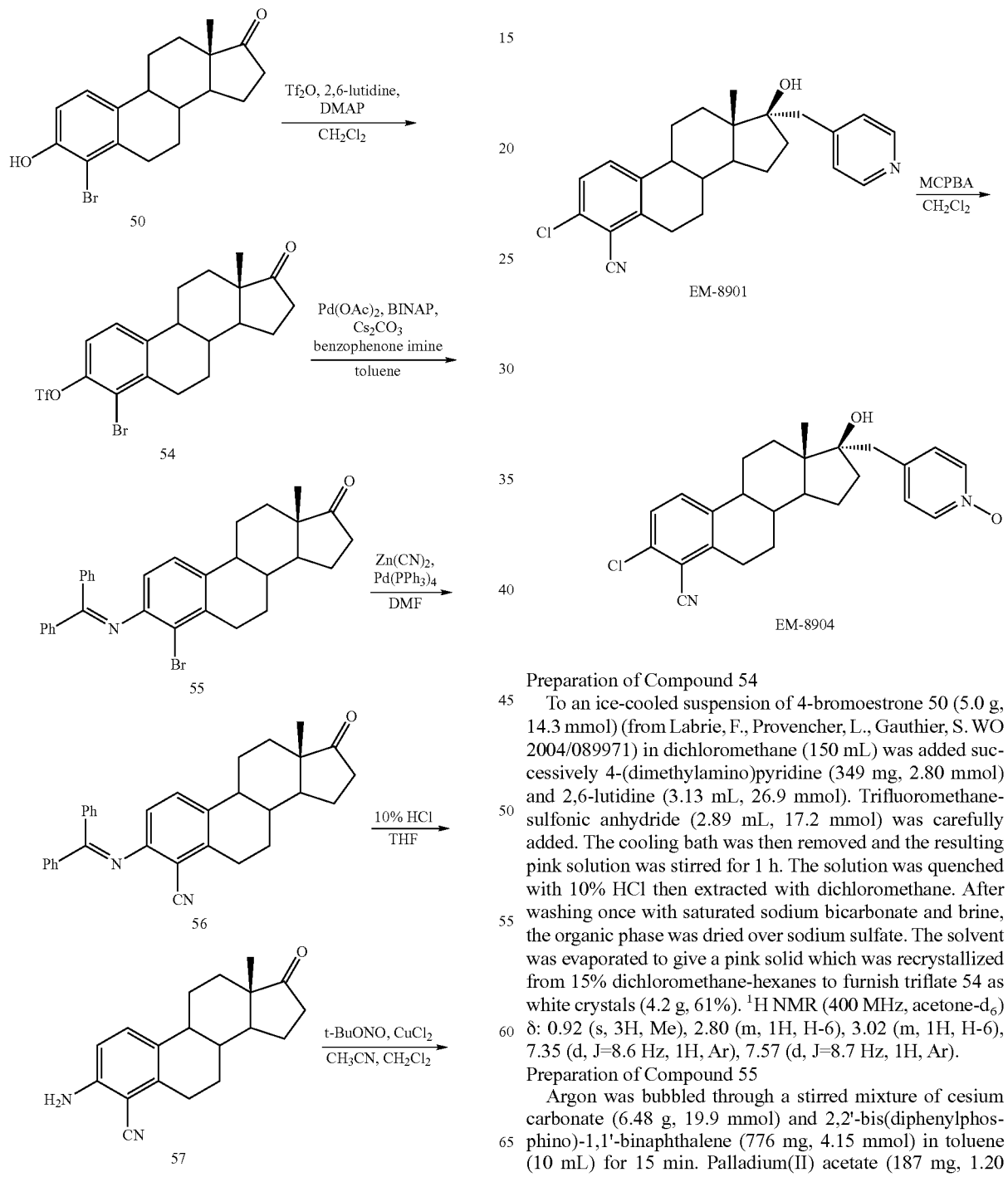

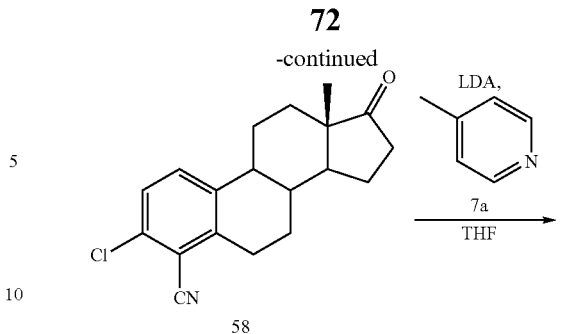

Preparation of Compound 54

To an ice-cooled suspension of 4-bromoestrone 50 (5.0 g, 14.3 mmol) (from Labrie, F., Provencher, L., Gauthier, S. WO 2004/089971) in dichloromethane (150 mL) was added successively 4-(dimethylamino)pyridine (349 mg, 2.80 mmol) and 2,6-lutidine (3.13 mL, 26.9 mmol). Trifluoromethanesulfonic anhydride (2.89 mL, 17.2 mmol) was carefully added. The cooling bath was then removed and the resulting pink solution was stirred for 1 h. The solution was quenched with 10% HCl then extracted with dichloromethane. After washing once with saturated sodium bicarbonate and brine, the organic phase was dried over sodium sulfate. The solvent was evaporated to give a pink solid which was recrystallized from 15% dichloromethane-hexanes to furnish triflate 54 as white crystals (4.2 g, 61%). $^1$H NMR (400 MHz, acetone-d$_6$) δ: 0.92 (s, 3H, Me), 2.80 (m, 1H, H-6), 3.02 (m, 1H, H-6), 7.35 (d, J=8.6 Hz, 1H, Ar), 7.57 (d, J=8.7 Hz, 1H, Ar).

Preparation of Compound 55

Argon was bubbled through a stirred mixture of cesium carbonate (6.48 g, 19.9 mmol) and 2,2'-bis(diphenylphosphino)-1,1'-binaphthalene (776 mg, 4.15 mmol) in toluene (10 mL) for 15 min. Palladium(II) acetate (187 mg, 1.20 mmol) was added and the resulting yellow slurry was heated at 50-60° C. for 10 min which gradually changed from yellow to red color. A solution of triflate 54 (8.00 g, 16.6 mmol) and benzophenone imine (4.2 mL, 24.9 mmol) in toluene (30 mL) was added via a cannula. The resulting mixture was vigorously stirred and heated to 100-105° C. for 60 h. The reaction mixture was allowed to cool to room temperature, diluted with ethyl acetate and filtered through a pad of celite which was washed with additional ethyl acetate. After concentration and flash chromatography with 1% ethyl acetate-toluene, the orange residue was triturated from methanol (50 mL) to give imine 55 as a yellow solid (5.90 g, 70%). $^1$H NMR (400 MHz, acetone-$d_6$) δ: 0.88 (s, 3H, Me), 2.65 (m, 1H, H-6), 2.94 (m, 1H, H-6), 6.45 (d, J=8.2 Hz, 1H, H-2), 7.08 (d, J=8.3 Hz, 1H, H-1), 7.24-7.70 (m, 10H, phenyl).

Preparation of Compound 56

Cyanation of 3-iminosteroid 55 (2.0 mmol) with zinc cyanide (4.0 mmol) and tetrakis(triphenylphosphine)palladium (0.40 mmol) as catalyst was carried out in DMF at 120-125° C. as reported for preparation of compound 4 without trituration and chromatography.

Preparation of Compound 57

To a solution of crude 3-cyanoimime 56 in THF (10 mL) was added 10% HCl (1 mL) and the mixture was stirred at room temperature for 1 h (the yellow color gradually disappeared). Then, the pH was brought to >7 by addition of 10% sodium hydroxide and the aqueous phase was extracted with dichloromethane. The combined organic phase was washed with brine and dried over sodium sulfate. Evaporation of the solvent led to a residue which was triturated from acetone to give amine 57 (390 mg, 66%) as an off-white solid. Flash chromatography of the mother liquors eluting first with 50% hexanes-dichloromethane then 1% ethyl acetate-dichloromethane afforded a second crop of amine 57 (125 mg, 21%). $^1$H NMR (400 MHz, CDCl$_3$) δ: 0.91 (s, 3H, Me), 2.85 (m, 1H, H-6), 2.95 (m, 1H, H-6), 4.27 (bs, 2H, NH$_2$), 6.57 (d, J=8.7 Hz, 1H, H-2), 7.27 (d, J=8.5 Hz, 1H, H-1).

Preparation of Compound 58

Diazotation and chloration of amine 57 (2.70 mmol) were accomplished as described for preparation of compound 30 except that acetonitrile-dichloromethane/2:1 was used instead of acetonitrile. The crude product was purified by flash chromatography with 5% ethyl acetate-hexanes to give 3-chloro steroid 58 as a white solid (564 mg, 66%). $^1$H NMR (400 MHz, acetone-$d_6$) δ: 0.91 (s, 3H, Me), 3.00 (m, 1H, H-6), 3.12 (m, 1H, H-6), 7.44 (d, J=8.6 Hz, H, Ar), 7.67 (d, J=8.3 Hz, 1H, Ar).

Preparation of EM-8901

EM-8901 (80 mg, 48%, white solid) was prepared from compound 58 according to preparation of EM-5855. $^1$H NMR (400 MHz, acetone-$d_6$) δ: 0.99 (s, 3H, Me), 2.77 (d, J$_{gem}$=13.2 Hz, 1H, —CH$_2$-Pyr), 2.93 (d, J$_{gem}$=13.2 Hz, 1H, —CH$_2$-Pyr), 2.95 (m, 1H, H-6), 3.09 (m, 1H, H-6), 7.36 (d, J=5.8 Hz, 2H, Pyr), 7.43 (d, J=8.6 Hz, 1H, Ar), 7.68 (d, J=8.5 Hz, 1H, Ar), 8.44 (d, J=5.4 Hz, 2H, Pyr).

Preparation of EM-8904

EM-8901 was treated with 3-chloroperbenzoic acid 70% at room temperature as described for preparation of EM-5854. The crude product was triturated from acetone to give EM-8904 (61 mg, 95%) as a white solid. $^1$H NMR (400 MHz, CDCl$_3$) δ: 0.96 (s, 3H, Me), 2.59 (d, J$_{gem}$=13.2 Hz, 1H, —CH$_2$-Pyr), 2.93 (d, J$_{gem}$=13.2 Hz, 1H, —CH$_2$-Pyr), 3.01 (m, 1H, H-6), 3.17 (m, 1H, H-6), 7.27 (m, 3H, Pyr, Ar), 7.45 (d, J=8.6 Hz, 1H, Ar), 8.12 (d, J=6.9 Hz, 2H, Pyr).

Example 12

Synthesis of EM-5886 and EM-5927

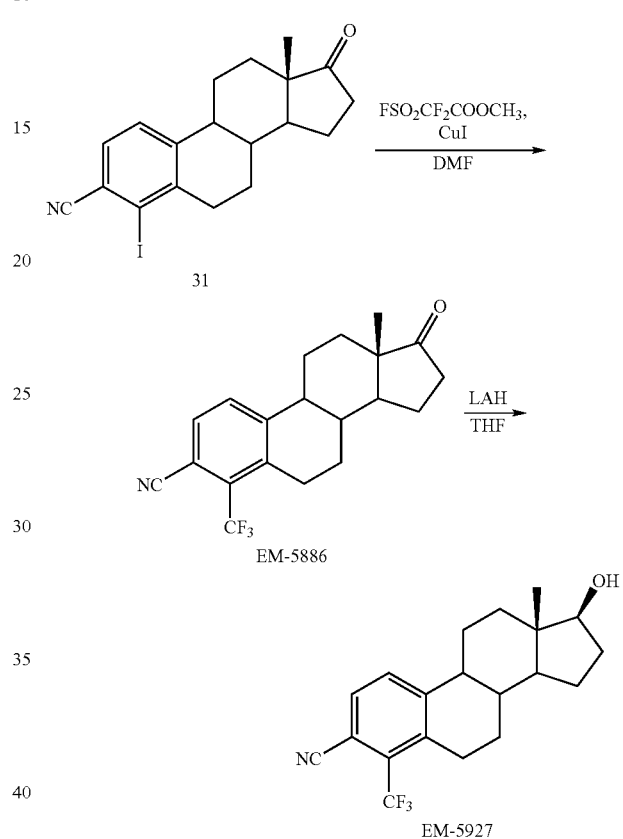

Scheme 12

Preparation of EM-5886

A suspension of 4-iodosteroid 31 (290 mg, 0.71 mmol), methyl-2,2-difluoro-2-fluorosulfonylacetate (0.46 mL, 3.58 mmol) and copper(I) iodide (99.999% purity, 136 mg, 0.71 mmol) were heated in dry DMF (5 mL) at 110° C. for 17 h. After cooling to room temperature, the reaction mixture was diluted with ethyl acetate and filtered through a pad of celite. The filtrate was washed with 10% sodium bisulfite and brine, then dried over sodium sulfate. Concentration and flash chromatography of the residue with 10% ethyl acetate-hexanes gave steroid EM-5886 (187 mg, 76%) as a white solid. $^1$H NMR (400 MHz, CDCl$_3$) δ: 0.92 (s, 3H, Me), 3.10 (m, 2H, H-6), 7.81 (d, J=8.3 Hz, 1H, Ar), 7.86 (d, J=8.3 Hz, 1H, Ar); MS (APCI+) m/z 348 (M+H, 100).

Preparation of EM-5927

To a cooled (−78° C.) solution of EM-5886 (75 mg, 0.21 mmol) in THF (5 mL) was added lithium aluminum hydride (1 M in THF, 0.21 mL, 0.21 mmol). After 5 min at the same temperature, sodium sulfate was added and the mixture was stirred for 2 h. After filtration, the solvent was evaporated to give EM-5927 as a white solid (40 mg, 53%). $^1$H NMR (400 MHz, CDCl$_3$) δ: 0.79 (s, 3H, Me), 3.10 (m, 2H, H-6), 3.69 (t, J=7.1 Hz, H-17), 7.79 (d, J=8.3 Hz, 1H, Ar), 7.84 (d, J=8.3 Hz, 1H, Ar)); MS (APCI+) m/z 350 (M+H, 100).

Example 13

Synthesis of EM-8419 and EM-9040

Scheme 13

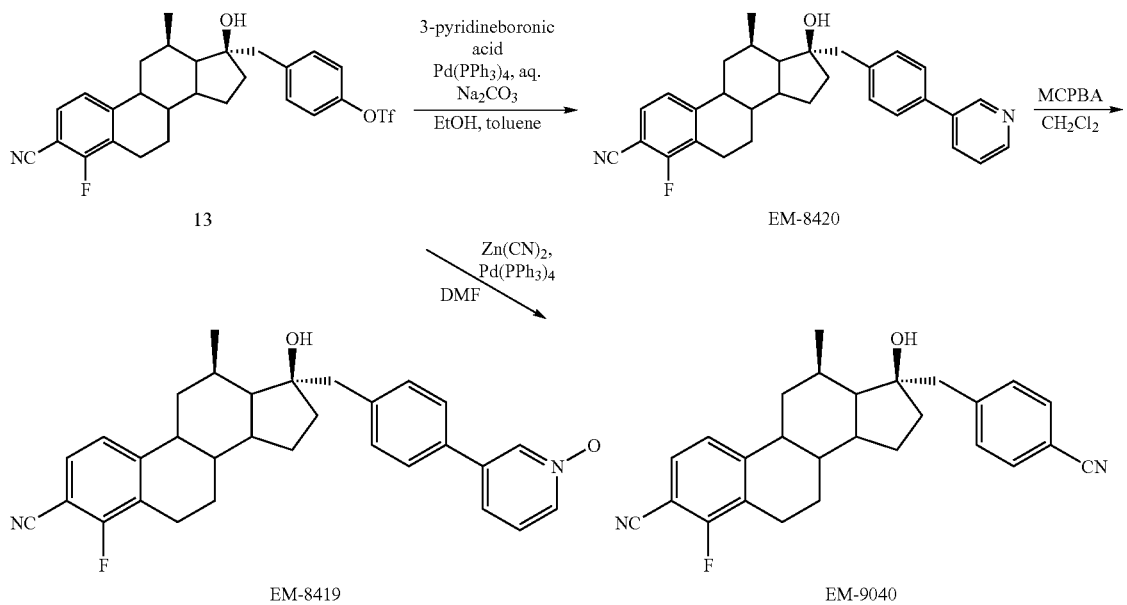

Preparation of EM-8420

A mixture of compound 13 (125 mg, 0.23 mmol), 3-pyridineboronic acid (43 mg, 0.35 mmol), tetrakis(triphenylphosphine)palladium (6.0 mg, 0.0052 mmol) in toluene (2.3 mL) and ethanol (2.3 mL) was purged with argon while stirring for 15 min. Then, an aqueous solution of sodium carbonate (2.0 M, 460 μL, 0.92 mmol) was added, and the mixture was purged with argon for another 10 min. The mixture was stirred for 16 h under reflux. After completion of the reaction, the mixture was diluted with aqueous saturated sodium bicarbonate and extracted with ethyl acetate (3×). The combined organic layer was washed with aqueous saturated sodium bicarbonate and brine, dried over MgSO$_4$, filtered, and concentrated under reduced pressure. The crude compound was purified by flash chromatography (silica gel, 0-30% acetone in hexanes) to give 85 mg (78%) of EM-8420. $^1$H NMR (400 MHz, CDCl$_3$) δ: 0.99 (s, 3H, Me), 2.74 (m, 2H, —CH$_2$-Ph, H-6), 2.99 (m, 2H, —CH$_2$-Ph, H-6), 7.21 (d, J=8.2 Hz, 1H, Ar), 7.41 (t, J=7.7 Hz, 1H, Ar), 7.47 (d, J=8.1 Hz, 2H, Ar) 7.56 (d, J=8.1 Hz, 2H, Ar), 7.62 (t, J=5.4 Hz, 1H, Pyr), 8.16 (d, J=7.9 Hz, 1H, Pyr), 8.62 (d, J=4.6 Hz, 1H, Pyr), 8.91 (s, 1H, Pyr).

Preparation of EM-8419

To a solution of EM-8420 (77 mg, 0.16 mmol) in anhydrous dichloromethane (10 mL) at 0° C. was added 3-chloroperoxybenzoic acid (50 mg, 0.18 mmol). The mixture was stirred for 2 h at 22° C. and evaporated to dryness. The crude compound was purified by flash chromatography (silica gel, 0-10% methanol in dichloromethane) to give 61 mg (77%) of EM-8419. $^1$H NMR (400 MHz, CDCl$_3$) δ: 0.99 (s, 3H, Me), 2.73 (m, 2H, —CH$_2$-Ph, H-6), 2.98 (m, 2H, —CH$_2$-Ph, H-6), 7.21 (d, J=8.3 Hz, 1H, Ar), 7.35 (t, J=7.8 Hz, 1H, Ar), 7.47 (m, 6H, Ar, Pyr), 8.20 (d, J=6.4 Hz, 1H, Pyr), 8.49 (s, 1H, Pyr).

Preparation of EM-9040

EM-9040 was prepared from compound 13 (65 mg, 0.12 mmol) using the procedure described for compound 4. The crude compound was purified by flash chromatography (silica gel, 0-100% acetone in hexanes) to give 16 mg (32%) of EM-9040. $^1$H NMR (400 MHz, CDCl$_3$) δ: 0.97 (s, 3H, Me), 2.71 (m, 2H, —CH$_2$-Ph, H-6), 2.98 (m, 2H, —CH$_2$-Ph, H-6), 7.20 (d, J=8.3 Hz, 1H, Ar), 7.40 (t, J=7.7 Hz, 1H, Ar), 7.43 (d, J=8.2 Hz, 2H, Ar), 7.60 (d, J=8.2 Hz, 2H, Ar).

Example 14

Synthesis of EM-9017 and Derivatives

Scheme 14

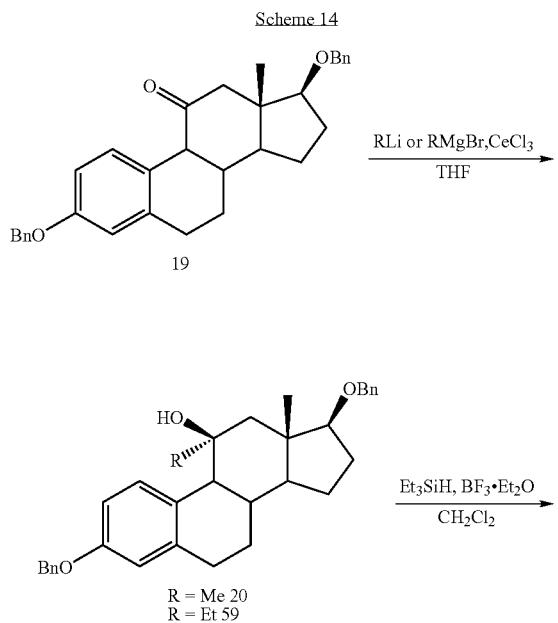

R = Me 20
R = Et 59

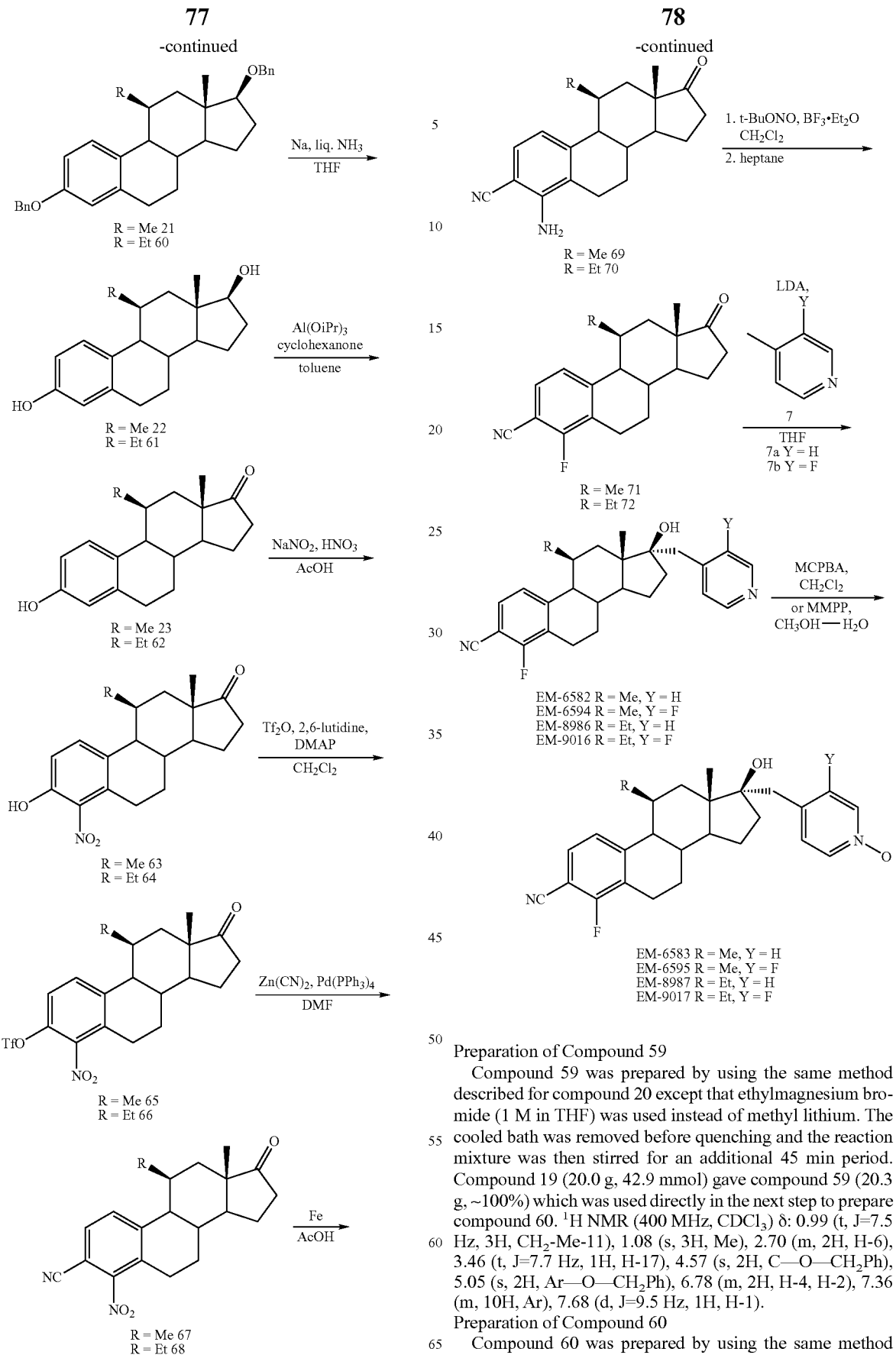

Preparation of Compound 59

Compound 59 was prepared by using the same method described for compound 20 except that ethylmagnesium bromide (1 M in THF) was used instead of methyl lithium. The cooled bath was removed before quenching and the reaction mixture was then stirred for an additional 45 min period. Compound 19 (20.0 g, 42.9 mmol) gave compound 59 (20.3 g, ~100%) which was used directly in the next step to prepare compound 60. $^1$H NMR (400 MHz, CDCl$_3$) δ: 0.99 (t, J=7.5 Hz, 3H, CH$_2$-Me-11), 1.08 (s, 3H, Me), 2.70 (m, 2H, H-6), 3.46 (t, J=7.7 Hz, 1H, H-17), 4.57 (s, 2H, C—O—CH$_2$Ph), 5.05 (s, 2H, Ar—O—CH$_2$Ph), 6.78 (m, 2H, H-4, H-2), 7.36 (m, 10H, Ar), 7.68 (d, J=9.5 Hz, 1H, H-1).

Preparation of Compound 60

Compound 60 was prepared by using the same method described for compound 21 except that we used 2 equivalents of triethylsilane and 4 equivalents of boron trifluoride diethyl etherate. Compound 59 (20.3 g, 40.9 mmol) gave compound 60 (18.7 g, ~100%) which was used directly in the next step to prepare compound 61. $^1$H NMR (400 MHz, CDCl$_3$) δ: 0.93 (t, J=7.3 Hz, 3H, CH$_2$-Me-11), 1.01 (s, 3H, Me), 2.75 (m, 2H, H-6), 3.48 (t, J=7.4 Hz, 1H, H-17), 4.59 (s, 2H, C—O—CH$_2$Ph), 5.03 (s, 2H, Ar—O—CH$_2$Ph), 6.69 (s, 1H, H-4), 6.79 (d, J=8.6 Hz, 1H, H-2), 7.06 (d, J=8.6 Hz, 1H, H-1), 7.37 (m, 10H, Ar).

Preparation of Compound 61

Compound 61 was prepared by using the same method described for compound 22. Compound 60 (18.7 g, 39.0 mmol) gave compound 61 (13.6 g, >100%) which was used directly in the next step to prepare compound 62. $^1$H NMR (400 MHz, CDCl$_3$) δ: 0.92 (m, 6H, Me, CH$_2$-Me-11), 2.75 (m, 2H, H-6), 3.71 (t, J=14.1 Hz, 1H, H-17), 6.54 (s, 1H, H-4), 6.64 (d, J=8.4 Hz, 1H, H-2), 7.02 (d, J=8.4 Hz, 1H, H-1).

Preparation of Compound 62

Compound 62 was prepared by using the same method described for compound 23 except that reaction was more concentrated (350 mL of cyclohexanone-toluene). Compound 61 (13.6 g, 39.0 mmol) gave compound 62 (7.4 g, 58%) after trituration in diethyl ether. Compound 62 was used directly in the next step to prepare compound 64. $^1$H NMR (400 MHz, CDCl$_3$) δ: 0.92 (t, J=7.4 Hz, 3H, CH$_2$-Me-11), 1.04 (s, 3H, Me), 2.75 (m, 2H, H-6), 6.56 (s, 1H, H-4), 6.65 (d, J=8.4 Hz, 1H, H-2), 7.02 (d, J=8.4 Hz, 1H, H-1).

Preparation of Compound 63

A solution of nitric acid prepared in compound 64 procedure (8 mL, 18 mmol) was added dropwise in small portions to a solution of compound 23 (5.18 g, 18 mmol) in glacial acetic acid (800 mL) which was heated at 50° C. overnight. The reaction was monitored by NMR. The reaction mixture was evaporated and the obtained residue was chromatographed (toluene to toluene-ethyl acetate/9:1) to give 3.14 g of the desired compound 63 (48%) and 2.03 g of 2-nitro isomer 63a (31%). Compound 63: $^1$H NMR (400 MHz, CDCl$_3$) δ: 0.86 (d, J=7.5 Hz, 3H, Me-11), 1.04 (s, 3H, Me), 2.74 (m, 2H, H-6), 6.99 (d, J=8.8 Hz, 1H, Ar), 7.38 (d, J=8.9 Hz, 1H, Ar). Compound 63a: $^1$H NMR (400 MHz, CDCl$_3$) δ: 0.92 (d, J=7.5 Hz, 3H, Me-11), 1.04 (s, 3H, Me), 2.91 (m, 2H, H-6), 6.86 (s, 1H, H-4), 7.90 (s, 1H, H-1), 10.36 (s, 1H, OH).

Preparation of Compound 64

A mixture of 70% nitric acid (1.0 mL), water (6.4 mL) and sodium nitrite (26 mg) was heated at 50° C. for 10 min. A portion of the nitric solution (2.55 mL, 5.48 mmol) was added dropwise to a solution of compound 62 (2.00 g, 6.71 mmol) in glacial acetic acid (600 mL). The reaction mixture was stirred for 30 min at room temperature, filtered (fritted glass funnel), and poured into cooled water to give a yellow solid after filtration (1.52 g). The aqueous phase was extracted with ethyl acetate. The combined organic phase was washed with water (2×) and brine, dried over MgSO$_4$, filtered, and evaporated to give an orange foam (0.66 g). The yellow solid and the orange foam (contains around 40% of 2-nitro isomer 64a) are combined and used directly in the next step to prepare compound 66. Analytical samples of compounds 64 and 64a were obtained by chromatography (hexanes-acetone/99:1 to hexanes-acetone/3:1). Compound 64: $^1$H NMR (400 MHz, CDCl$_3$) δ: 0.92 (m, 3H, CH$_2$-Me-11), 1.04 (s, 3H, Me), 2.75 (m, 2H, H-6), 7.00 (d, J=8.8 Hz, 1H, Ar), 7.38 (d, J=8.9 Hz, 1H, Ar). Compound 64a: $^1$H NMR (400 MHz, CDCl$_3$) δ: 0.96 (t, J=7.4 Hz, 3H, CH$_2$-Me-11), 1.05 (s, 3H, Me), 2.88 (m, 2H, H-6), 6.87 (s, 1H, H-4), 7.88 (s, 1H, H-1), 10.36 (s, 1H, OH).

Preparation of Compound 65

Compound 65 was prepared by using the same method described for compound 66. However, the crude product was chromatographed with different solvents (toluene to toluene-ethyl acetate/9:1) than for compound 66. Compound 63 (3.77 g, 11.4 mmol) gave compound 65 (4.7 g, 96%). $^1$H NMR (400 MHz, CDCl$_3$) δ: 0.92 (d, J=7.5 Hz, 3H, Me-11), 1.04 (s, 3H, Me), 2.74 (m, 2H, H-6), 7.30 (d, J=8.9 Hz, 1H, Ar), 7.41 (d, J=8.8 Hz, 1H, Ar).

Preparation of Compound 66

A solution of a mixture of compounds 64 and 64a (7.81 g, 22.8 mmol), 2,6-lutidine (5.3 mL, 46 mmol) and 4-dimethylaminopyridine (0.28 g, 2.3 mmol) in dichloromethane (380 mL) was cooled at 0° C., treated with trifluoromethanesulfonic anhydride (4.6 mL, 27 mmol), and stirred for 2 h. The reaction mixture was quenched with aqueous saturated ammonium chloride. The organic phase was washed with HCl 1 N, water and brine, dried over MgSO$_4$, filtered, and evaporated. The crude product was chromatographed (hexanes-ethyl acetate/19:1 to hexanes-ethyl acetate/1:1) to afford compound 66 (3.64 g, 34%). $^1$H NMR (400 MHz, CDCl$_3$) δ: 0.95 (t, J=7.4 Hz, 3H, CH$_2$-Me-11), 1.05 (s, 3H, Me), 2.78 (m, 2H, H-6), 7.30 (d, J=8.9 Hz, 1H, Ar), 7.41 (d, J=8.8 Hz, 1H, Ar).

Preparation of Compound 67

Compound 67 was prepared by using the same method described for compound 68. Compound 65 (4.70 g, 10.2 mmol) gave compound 67 (2.76 g, 80%). $^1$H NMR (400 MHz, CDCl$_3$) δ: 0.92 (d, J=7.5 Hz, 3H, Me-11), 1.07 (s, 3H, Me), 2.85 (m, 2H, H-6), 7.53 (d, J=8.3 Hz, 1H, Ar), 7.63 (d, J=8.2 Hz, 1H, Ar).

Preparation of Compound 68

Under an argon atmosphere, a solution of compound 66 (3.64 g, 7.66 mmol), zinc cyanide (2.7 g, 23 mmol) and tetrakis(triphenylphosphine)palladium (1.33 g, 1.15 mmol) in DMF (200 mL) was bubbled with argon for 10 min and heated at 140-150° C. for 1.5 h. The reaction mixture was cooled at room temperature, filtered on celite, and concentrated. The residue was filtered on silica gel (dichloromethane as eluent) and chromatographed (hexanes-ethyl acetate/19:1 to hexanes-ethyl acetate/1:2) to give compound 68 (2.22 g, 82%). $^1$H NMR (400 MHz, CDCl$_3$) δ: 0.94 (t, J=7.3 Hz, 3H, CH$_2$-Me-11), 1.06 (s, 3H, Me), 2.80 (m, 2H, H-6), 7.48 (d, J=8.2 Hz, 1H, Ar), 7.61 (d, J=8.2 Hz, 1H, Ar).

Preparation of Compound 69

Compound 69 was prepared by using the same method described for compound 70. Compound 67 (2.76 g, 8.16 mmol) gave compound 69 (2.01 g, 80%). $^1$H NMR (300 MHz, CDCl$_3$) δ: 0.85 (d, J=7.4 Hz, 3H, Me-11), 1.02 (s, 3H, Me), 2.85 (m, 2H, H-6), 6.69 (d, J=8.4 Hz, 1H, Ar), 7.24 (d, J=8.3 Hz, 1H, Ar).

Preparation of Compound 70

Compound 70 was prepared by using the same method described for compound 5 except that 3 equivalents of iron (instead of 2.5) was used, and the reaction mixture was three times more diluted and heated at 100° C. (instead of 80° C.). The crude solid was dissolved in dichloromethane. The organic phase was washed with water and brine, dried over MgSO$_4$, filtered, and evaporated. The crude product was chromatographed (hexanes-acetone/49:1 to hexanes-acetone/2:1) to afford compound 70 (1.70 g, 84% yield starting from 2.22 g, 6.31 mmol of compound 68). $^1$H NMR (400 MHz, acetone-d$_6$) δ: 0.90 (t, J=7.4 Hz, 3H, CH$_2$-Me-11), 1.02 (s, 3H, Me), 2.71 (m, 2H, H-6), 6.70 (d, J=8.3 Hz, 1H, Ar), 7.22 (d, J=8.3 Hz, 1H, Ar).

Preparation of Compound 71

Compound 71 was prepared by using the same method described for compound 72 except that the chromatography was performed with hexanes-dichloromethane-ethyl acetate/15:4:1 to hexanes-dichloromethane-ethyl acetate/3:1:1. Compound 69 (2.01 g, 6.53 mmol) gave compound 71 (0.61 g, 30%). $^1$H NMR (300 MHz, acetone-d$_6$) δ: 0.89 (d, J=7.5 Hz, 3H, Me-11), 1.02 (s, 3H, Me), 2.96 (m, 2H, H-6), 7.33 (d, J=8.2 Hz, 1H, Ar), 7.58 (t, J=7.7 Hz, 1H, Ar).

Preparation of Compound 72

Compound 72 was prepared by using the same method described for compound 6. The crude product was chromatographed (hexanes-acetone/99:1 to hexanes-acetone/2:1) to afford compound 72 (0.33 g, 19% yield starting from 1.70 g, 5.28 mmol of compound 70). $^1$H NMR (400 MHz, methanol-d$_6$) δ: 0.98 (t, J=7.2 Hz, 3H, CH$_2$-Me-11), 1.09 (s, 3H, Me), 3.32 (m, 2H, H-6), 8.23 (d, J=8.2 Hz, 1H, Ar), 8.32 (d, J=8.4 Hz, 1H, Ar).

EM-6582

To a solution of diisopropylamine (0.17 mL, 1.2 mmol) in anhydrous THF (1.8 mL) at −78° C. was added dropwise a solution of n-BuLi (2.5 M in hexanes, 0.48 mL, 1.2 mmol). The mixture was stirred for 30 min at −78° C. under an argon atmosphere. To this freshly prepared LDA solution (0.5 M) was added dropwise a solution of 4-picoline 7a (0.116 mL, 1.2 mmol) in THF (2 mL). The mixture was stirred at −78° C. After 1 h, a solution of compound 71 (72 mg, 0.23 mmol) in THF (2 mL) was added and the mixture was stirred for 1 h at −78° C. under an argon atmosphere. After completion of the reaction (TLC), the reaction was quenched by addition of aqueous saturated ammonium chloride. The mixture was extracted with ethyl acetate (3×). The combined organic phase was washed with aqueous saturated sodium bicarbonate and brine, dried over MgSO$_4$, filtered, and concentrated. The crude compound was purified by flash chromatography (silica gel, chloroform-acetone/9:1 to chloroform-acetone/3:2) to give EM-6582 (50 mg, 53%). $^1$H NMR (400 MHz, CDCl$_3$) δ: 0.94 (d, J=7.5 Hz, 3H, Me-11), 1.13 (s, 3H, Me), 2.62 (m, 2H, CH$_2$-Pyr), 3.02 (m, 2H, H-6), 7.13 (d, J=8.2 Hz, 1H, Ar), 7.43 (t, J=7.3 Hz, 1H, Ar), 7.70 (bs, 2H, Pyr), 8.58 (bs, 2H, Pyr).

EM-6594

EM-6594 was prepared by using the same method described for compound EM-6582 except that picoline 7b hydrochloride was used, and the amount of LDA was doubled. The chromatography was performed with hexanes-acetone/9:1 to hexanes-acetone/3:2. Moreover, the chromatographed compound was triturated from hexanes-acetone/9:1. Compound 71 (100 mg, 0.321 mmol) gave EM-6594 (62 mg, 46%). $^1$H NMR (400 MHz, CDCl$_3$) δ: 0.94 (d, J=7.5 Hz, 3H, Me-11), 1.12 (s, 3H, Me), 2.84 (m, 2H, CH$_2$-Pyr, H-6), 2.99 (m, 2H, CH$_2$-Pyr, H-6), 7.14 (d, J=8.3 Hz, 1H, Ar), 7.42 (t, J=7.7 Hz, 1H, Ar), 7.51 (bs, 1H, Pyr), 8.38 (bs, 1H, Pyr), 8.47 (bs, 1H, Pyr).

EM-8986

EM-8986 was prepared by using the same method described for compound EM-6582 except that the chromatography was performed with hexanes-acetone/3:1 to acetone to acetone-methanol/9:1. Compound 72 (70 mg, 0.22 mmol) gave EM-8986 (25 mg, 28%). $^1$H NMR (400 MHz, CDCl$_3$) δ: 0.94 (t, J=7.3 Hz, 3H, CH$_2$-Me-11), 1.11 (s, 3H, Me), 2.63 (m, 2H, CH$_2$-Pyr, H-6), 2.97 (m, 2H, CH$_2$-Pyr, H-6), 7.08 (d, J=8.3 Hz, 1H, Ar), 7.27 (bs, 2H, Pyr), 7.39 (t, J=7.5 Hz, 1H, Ar), 8.51 (bs, 2H, Pyr).

EM-9016

EM-9016 was prepared by using the same method described for compound EM-6582 except that picoline 7b was used. The chromatography was performed with hexanes to acetone. Compound 72 (67 mg, 0.21 mmol) gave EM-9016 (88 mg, 96%). $^1$H NMR (400 MHz, CDCl$_3$) δ: 0.94 (t, J=7.3 Hz, 3H, CH$_2$-Me-11), 1.11 (s, 3H, Me), 2.63 (m, 1H, H-6), 2.81 (d, J=13.3 Hz, 1H, CH$_2$-Pyr), 2.97 (m, 2H, CH$_2$-Pyr, H-6), 7.09 (d, J=8.3 Hz, 1H, Ar), 7.40 (m, 2H, Ar, Pyr), 8.34 (bs, 1H, Pyr), 8.42 (bs, 1H, Pyr).

EM-6583

EM-6583 was prepared by using the same method described for compound EM-8419 except that the chromatography was performed with chloroform-methanol/99:1 to chloroform-methanol/9:1. EM-6582 (50 mg, 0.12 mmol) gave EM-6583 (30 mg, 58%). $^1$H NMR (400 MHz, CDCl$_3$) δ: 0.93 (d, J=7.5 Hz, 3H, Me-11), 1.12 (s, 3H, Me), 2.74 (d, J=13.3 Hz, 1H, CH$_2$-Pyr), 2.87-3.11 (m, 3H, CH$_2$-Pyr, H-6), 7.13 (d, J=8.3 Hz, 1H, Ar), 7.41 (m, 1H, Ar), 7.65 (bs, 2H, Pyr), 8.49 (bs, 2H, Pyr).

EM-6595

EM-6595 was prepared by using the same method described for compound EM-8419 except that the chromatography was performed with chloroform-acetone/9:1 to chloroform-acetone/3:2 followed by chloroform-methanol/19:1 to chloroform-methanol/9:1. EM-6594 (40 mg, 0.095 mmol) gave EM-6595 (31 mg, 72%). $^1$H NMR (400 MHz, CDCl$_3$) δ: 0.93 (d, J=7.5 Hz, 3H, Me-11), 1.11 (s, 3H, Me), 2.78-3.04 (m, 4H, CH$_2$-Pyr, H-6), 7.13 (d, J=8.2 Hz, 1H, Ar), 7.42 (t, J=7.5 Hz, 1H, Ar), 7.55 (bs, 1H, Pyr), 8.08 (bs, 1H, Pyr), 8.23 (bs, 1H, Pyr).

EM-8987

EM-8987 was prepared by using the same method described for compound EM-9013 except that dichloromethane was used in the work up and the crude compound was not purified by HPLC but triturated from methanol (2 mL). EM-8986 (45 mg, 0.11 mmol) gave EM-8987 (31 mg, 65%). $^1$H NMR (400 MHz, methanol-d$_4$) δ: 0.98 (t, J=7.3 Hz, 3H, CH$_2$-Me-11), 1.12 (s, 3H, Me), 2.63 (m, 2H, H-6), 2.85-3.01 (m, 3H, CH$_2$-Pyr, OH), 7.27 (d, J=8.3 Hz, 1H, Ar), 7.51 (t, J=7.7 Hz, 1H, Ar), 7.56 (d, J=6.9 Hz, 2H, Pyr), 8.26 (d, J=6.9 Hz, 2H, Pyr).

EM-9017

EM-9017 was prepared by using the same method described for compound EM-9013 except that the crude compound was not purified by HPLC. EM-9016 (20 mg, 0.046 mmol) gave EM-9017 (20 mg, 96%). $^1$H NMR (400 MHz, CDCl$_3$) δ: 0.94 (t, J=7.3 Hz, 3H, CH$_2$-Me-11), 1.10 (s, 3H, Me), 2.67 (m, 1H, H-6), 2.77 (m, 1H, CH$_2$-Pyr), 2.93 (d, J=13.8 Hz, 1H, CH$_2$-Pyr), 2.98 (m, 1H, H-6), 7.08 (d, J=8.3 Hz, 1H, Ar), 7.40 (t, J=7.6 Hz, 1H, Ar), 7.45 (bs, 1H, Pyr), 7.99 (bs, 1H, Pyr), 8.14 (bs, 1H, Pyr).

Example 15

Synthesis of EM-5728

Scheme 15

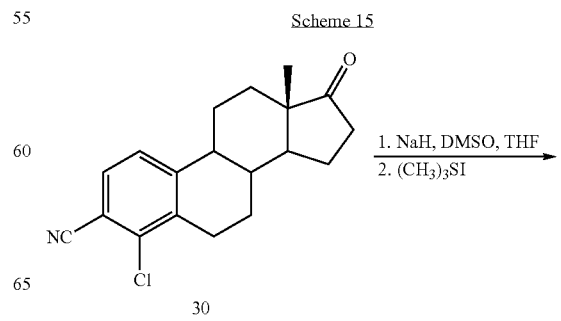

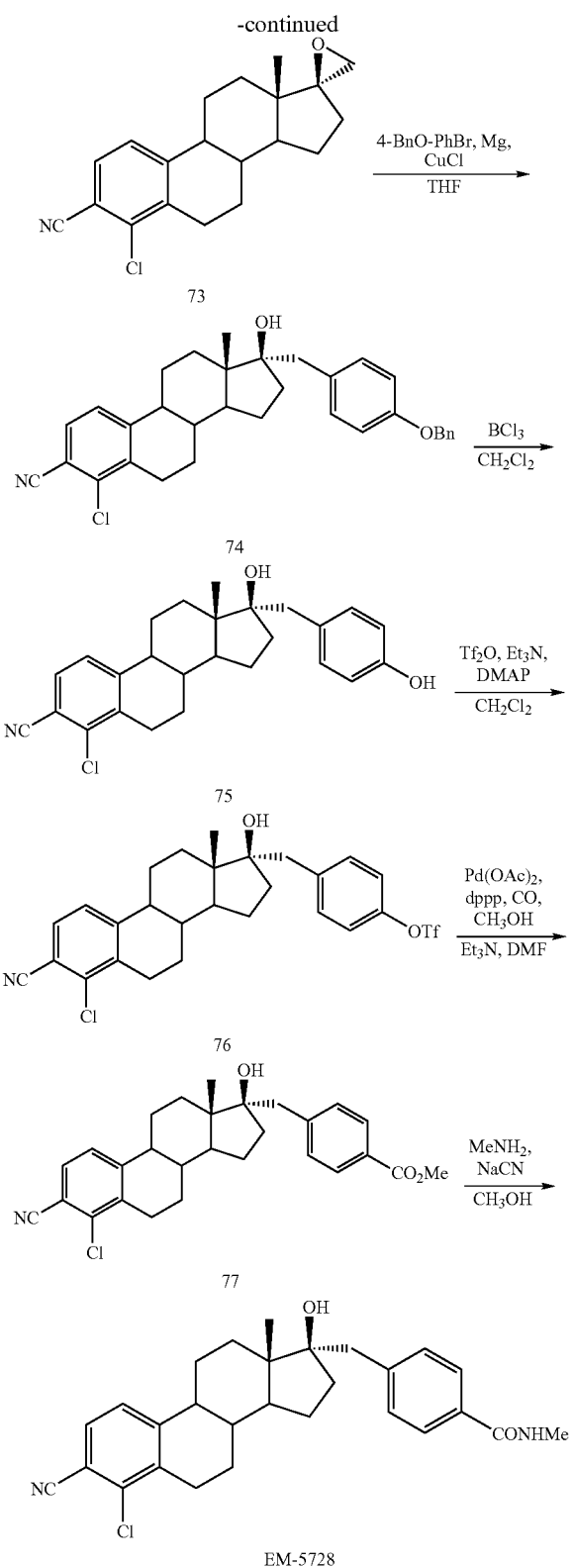

Preparation of Compound 73

In a dry 250 mL round-bottom flask equipped with a magnetic stirrer, under an argon atmosphere, a suspension of sodium hydride (1.2 g, 60% in oil, 30 mmol) in DMSO (25 mL) was stirred at 75° C. for 1 h. The mixture was ice-cooled to 0° C. and THF (10 mL) was added following by a solution of trimethylsulfonium iodide (6.2 g, 30 mmol) in DMSO (35 mL). The mixture was stirred for 5 min and a solution of compound 30 (1.50 g, 0.478 mmol) in THF (50 mL) was added. The mixture was stirred at room temperature for 3 h. After completion of the reaction (TLC), the reaction was quenched by addition of aqueous saturated ammonium chloride. The mixture was extracted with ethyl acetate (3×). The combined organic layer was washed with water (5×) and brine, dried over MgSO$_4$, filtered, and concentrated under reduced pressure. The crude compound was purified by flash chromatography (silica gel, 0-30% ethyl acetate in hexanes) to give 1.02 g (65%) of compound 73. $^1$H NMR (400 MHz, CDCl$_3$) δ: 0.92 (s, 3H, Me), 2.66 (d, J$_{gem}$=4.8 Hz, 1H, —CH$_2$—O), 2.74 (m, 1H, H-6), 2.96 (d, J$_{gem}$=4.9 Hz, 1H, —CH$_2$—O), 3.02 (m, 1H, H-6), 7.31 (d, J=8.3 Hz, 1H, Ar), 7.47 (d, J=8.1 Hz, 1H, Ar).

Preparation of Compound 74

After the addition of magnesium powder (2.81 g, 117 mmol) in a dry 3-neck round-bottom flask equipped with a magnetic stirrer, under an argon atmosphere, the system was flame dried. After cooling, dry THF (10 mL) was added. The suspension was stirred vigorously while a 4-benzyloxybromobenzene (15.5 g, 58.9 mmol) solution in THF (45 mL) was added dropwise until the temperature rose 30° C. The temperature was kept below 30° C. with an ice bath during the rest of the addition. The mixture was stirred at room temperature for 30 min. The freshly prepared Grignard solution (0.5 M) was added to a solution of copper(I) chloride (160 mg, 1.6 mmol) in THF (1 mL) and stirred 10 min to −10° C. Then, a solution of compound 73 (3.2 g, 9.8 mmol) in THF (65 mL) was added. The mixture was stirred for 3 h at 0° C. After completion of the reaction (TLC), the reaction was quenched by addition of aqueous saturated ammonium chloride. The mixture was extracted with ethyl acetate (3×). The combined organic layer was washed with aqueous saturated sodium bicarbonate and brine, dried over MgSO$_4$, filtered, and concentrated under reduced pressure. The crude compound was purified by flash chromatography (silica gel, 0-20% ethyl acetate in hexanes) to give 4.10 g (82%) of compound 74. $^1$H NMR (400 MHz, CDCl$_3$) δ: 0.96 (s, 3H, Me), 2.61 (d, J$_{gem}$=13.4 Hz, 1H, C—CH$_2$-Ph), 2.74 (m, 1H, H-6), 2.87 (d, J$_{gem}$=13.3 Hz, 1H, C—CH$_2$-Ph), 3.01 (m, 1H, H-6), 5.07 (s, 2H, O—CH$_2$-Ph), 6.95 (d, J=8.6 Hz, 2H, Ar), 7.21 (d, J=8.6 Hz, 2H, Ar), 7.41 (m, 7H, Ar, O-Bn).

Preparation of Compound 75

To a solution of compound 74 (4.10 g, 8.01 mmol) in anhydrous dichloromethane (840 mL) at −78° C. was added boron trichloride (1.0 M in dichloromethane, 24 mL, 24 mmol). The mixture was stirred at 0° C. for 1 h. After completion (TLC), the reaction was quenched with aqueous saturated sodium bicarbonate. The mixture was extracted with dichloromethane (3×). The combined organic layer was washed with aqueous saturated sodium bicarbonate and brine, dried over MgSO$_4$, filtered, and concentrated under reduced pressure. The crude compound was purified by flash chromatography (silica gel, 0-30% ethyl acetate in hexanes) to give 2.65 g (80%) of compound 75. $^1$H NMR (400 MHz, CDCl$_3$) δ: 0.96 (s, 3H, Me), 2.60 (d, J$_{gem}$=13.4 Hz, 1H, C—CH$_2$-Ph), 2.74 (m, 1H, H-6), 2.86 (d, J$_{gem}$=13.3 Hz, 1H, C—CH$_2$-Ph), 3.01 (m, 1H, H-6), 6.80 (d, J=8.4 Hz, 2H, Ar), 7.15 (d, J=8.3 Hz, 2H, Ar), 7.36 (d, J=8.3 Hz, 1H, Ar), 7.48 (d, J=8.1 Hz, 1H, Ar).

Preparation of Compound 76

Compound 76 was prepared from compound 75 (2.65 g, 6.29 mmol) using the procedure described for compound 13. The crude compound was purified by flash chromatography (silica gel, 0-10% ethyl acetate in toluene) to give 2.5 g (71%)

of compound 76. $^1$H NMR (400 MHz, CDCl$_3$) δ: 0.97 (s, 3H, Me), 2.66 (d, J$_{gem}$=13.5 Hz, 1H, C—CH$_2$-Ph), 2.74 (m, 1H, H-6), 2.96 (d, J$_{gem}$=13.3 Hz, 1H, C—CH$_2$-Ph), 3.01 (m, 1H, H-6), 7.22 (d, J=8.6 Hz, 2H, Ar), 7.35 (d, J=8.2 Hz, 1H, Ar), 7.39 (d, J=8.6 Hz, 2H, Ar), 7.49 (d, J=8.1 Hz, 1H, Ar).

Preparation of Compound 77

A solution of compound 76 (1.00 g, 1.81 mmol) and methanol (2 mL) in DMF (17 mL) was purged with argon while stirring for 15 min. Triethylamine (7.5 mL, 54 mmol) was added and the mixture was purged with argon for another 10 min. Then, palladium(II) acetate (28 mg, 0.13 mmol) and 1,3-bis(diphenylphosphino)propane (45 mg, 0.11 mmol) were added and the mixture was stirred at 90° C. for 3 h while bubbling carbon monoxide. After completion of the reaction, the mixture was filtered through celite and washed several times with ethyl acetate. The ethyl acetate solution was washed with water and brine, dried over MgSO$_4$, filtered, and concentrated under reduced pressure. The crude compound was purified by flash chromatography (silica gel, 0-30% ethyl acetate in hexanes) to give 724 mg (86%) of compound 77. $^1$H NMR (400 MHz, CDCl$_3$) δ: 0.96 (s, 3H, Me), 2.72 (m, 2H, C—CH$_2$-Ph, H-6), 3.00 (m, 2H, C—CH$_2$-Ph H-6), 3.91 (s, 3H, OMe), 7.34 (d, J=8.2 Hz, 1H, Ar), 7.38 (d, J=8.2 Hz, 2H, Ar), 7.48 (d, J=8.1 Hz, 1H, Ar), 7.99 (d, J=8.1 Hz, 2H, Ar).

Preparation of EM-5728

In a Schlenk tube, a mixture of compound 77 (100 mg, 0.22 mmol) and sodium cyanide (421 mg, 8.59 mmol) in dry methanol (5 mL) was purged with argon while stirring for 15 min. The mixture was cooled to −78° C. Methylamine (2 mL) was condensed and the tube was sealed. The mixture was stirred for 60 h at 65° C. After completion of the reaction, the mixture was cooled to −78° C. before the tube was opened. The temperature was brought back to 22° C. and the excess of methylamine was evaporated. The mixture was diluted with water and extracted with ethyl acetate (3×). The combined organic layer was washed with water and brine, dried over MgSO$_4$, filtered, and concentrated under reduced pressure. The crude compound was purified by flash chromatography (silica gel, 0-10% methanol in chloroform) to give 100 mg (quantitative) of EM-5728. $^1$H NMR (400 MHz, CDCl$_3$) δ: 0.97 (s, 3H, Me), 2.71 (m, 2H, C—CH$_2$-Ph, H-6), 3.03 (m, 5H, C—CH$_2$-Ph H-6, NH-Me), 7.37 (m, 3H, Ar), 7.49 (d, J=8.1 Hz, 1H, Ar), 7.72 (d, J=8.1 Hz, 2H, Ar).

Example 16

Synthesis of EM-9159

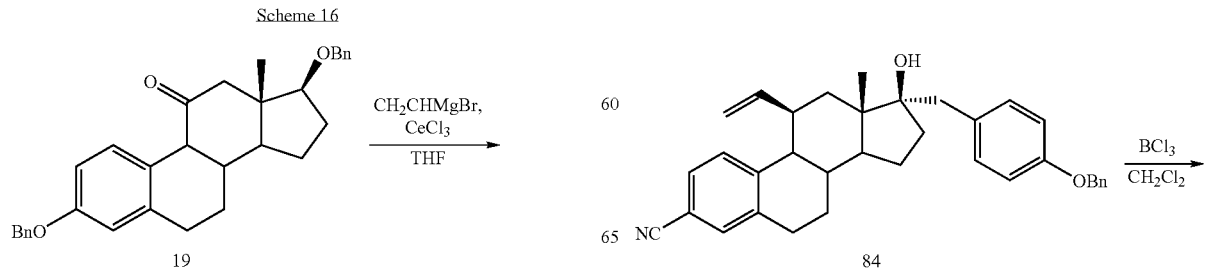

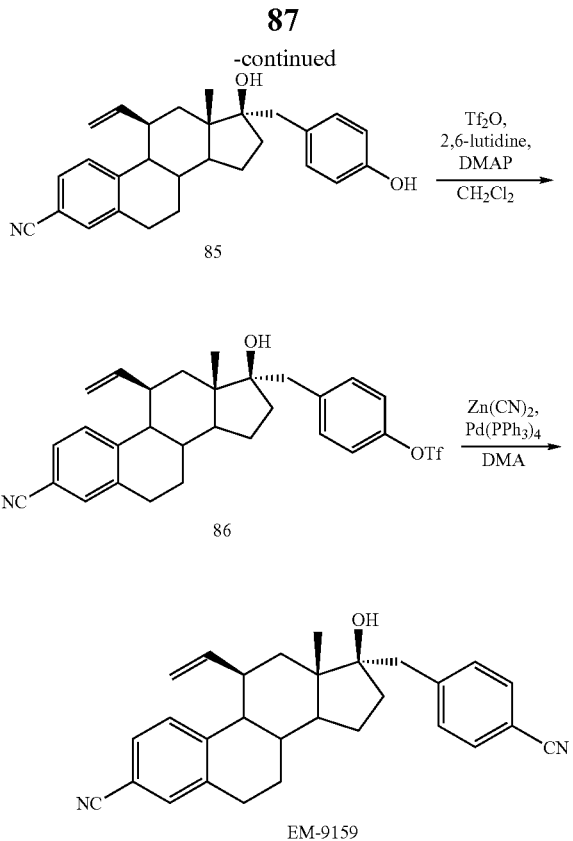

87

85

86

EM-9159

Preparation of Compound 78

Alcohol 78 was obtained as an oil from dibenzyl ketone 19 (10.0 g, 21.4 mmol) by reaction with vinylmagnesium bromide (1 M in THF, 54 mmol) and anhydrous cerium(III) chloride (54 mmol) as described for the preparation of compounds 20 and 59. The crude residue was purified by flash chromatography with 20% ethyl acetate-hexanes (9.25 g, 87%). $^1$H NMR (400 MHz, CDCl$_3$) δ: 1.12 (s, 3H, Me), 2.55 (d, J=10.6 Hz, 1H), 2.65-2.95 (m, 2H, H-6), 3.45 (t, J=8.0 Hz, 1H, H-17), 4.48 (d, J$_{gem}$=11.9 Hz, 1H, —O—CH$_2$-Ph), 4.58 (d, J$_{gem}$=12.2 Hz, 1H, —O—CH$_2$-Ph), 5.01 (s, 2H, —O—CH$_2$-Ph), 5.17 (d, J=10.5 Hz, 1H, vinyl), 5.44 (d, J=17.3 Hz, 1H, vinyl), 6.28 (dd, J=10.5 and 17.3 Hz, 1H, vinyl), 6.67 (dd, J=2.5 and 8.5 Hz, 1H, H-2), 6.73 (d, J=2.5 Hz, 1H, H-4), 7.24-7.43 (m, 10H, benzyl), 7.84 (d, J=8.5 Hz, 1H, H-1).

Preparation of Compound 79

Deoxygenation of alcohol 78 (9.20 g, 18.6 mmol) was achieved as described for the preparation of compound 21 using boron trifluoride diethyl etherate (279 mmol) and triethylsilane (93 mmol). The crude residue (8.68 g, 97%) was used directly in the next step without purification. $^1$H NMR (400 MHz, CDCl$_3$) δ: 1.12 (s, 3H, Me), 2.29 (dd, J=1.9 and 12.9 Hz, 1H), 2.46 (m, 1H), 2.70-2.92 (m, 2H, H-6), 3.30 (m, 1H), 3.46 (t, J=8.0 Hz, 1H, H-17), 4.55 (s, 2H, —O—CH$_2$-Ph), 4.96 (d, J=10.4 Hz, 1H, vinyl), 5.01 (s, 2H, —O—CH$_2$-Ph), 5.03 (d, J=18.8 Hz, 1H, vinyl), 5.73 (ddd, J=7.5, 10.5 and 18.7 Hz, 1H, vinyl), 6.67 (d, J=2.5 Hz, 1H, H-4), 6.74 (dd, J=2.5 and 8.5 Hz, 1H, H-2), 7.00 (d, J=8.5 Hz, 1H, H-1), 7.20-7.45 (m, 10H, benzyl).

Preparation of Compound 80

Debenzylation of compound 79 (8.68 g, 18.1 mmol) with sodium (126 mmol) in liquid ammonia was achieved as described for the preparation of compound 22 and gave steroid 80 (5.64 g). Compound 80 contains 1,2-diphenylethane and it was used directly in the next oxidation step without purification. $^1$H NMR (400 MHz, CDCl$_3$) δ: 0.81 (s, 3H, Me), 2.15 (dd, J=2.2 and 13.0 Hz, 1H), 2.46 (m, 1H), 2.65-2.80 (m, 2H, H-6), 3.25 (m, 1H), 3.50 (dt, J=1.8 and 7.7 Hz, 1H, H-17), 4.95 (d, J=10.4 Hz, 1H, vinyl), 4.96 (d, J=18.8 Hz, 1H, vinyl), 5.70 (ddd, J=7.5, 10.5 and 18.7 Hz, 1H, vinyl), 6.40 (d, J=2.5 Hz, 1H, H-4), 6.45 (dd, J=2.5 and 8.5 Hz, 1H, H-2), 6.83 (d, J=8.5 Hz, 1H, H-1).

Preparation of Compound 81

Oppenhauer's oxidation of crude alcohol 80 (5.64 g, 18.1 mmol) was accomplished as described for compound 23 using aluminum isopropoxide (41.7 mmol) and cyclohexanone to yield ketone 81 (3.30 g, 58%, 2 steps) as a beige solid. $^1$H NMR (400 MHz, CDCl$_3$) δ: 0.94 (s, 3H, Me), 2.49-2.55 (m, 2H), 2.65-2.83 (m, 2H, H-6), 3.31 (m, 1H), 4.98 (dd, J=10.9 Hz, 1H, vinyl), 5.04 (d, J=18.8 Hz, 1H, vinyl), 5.66 (ddd, J=7.5, 10.5 and 18.7 Hz, 1H, vinyl), 6.56 (d, J=2.5 Hz, 1H, H-4), 6.61 (dd, J=2.5 and 8.5 Hz, 1H, H-2), 6.96 (d, J=8.5 Hz, 1H, H-1).

Preparation of Compound 83

3-cyanosteroid 83 (589 mg, 45% for 2 steps) was obtained from phenol 81 (1.25 g, 4.22 mmol) via triflate 82 as described for the preparation of compound 13 except that dimethylacetamide (heated at 120° C.) was used instead of DMF. Crude product was purified by flash chromatography eluting with 1-5% ethyl acetate-toluene. $^1$H NMR (400 MHz, CDCl$_3$) δ: 0.95 (s, 3H, Me), 2.62 (m, 1H), 2.92 (m, 2H, H-6), 3.31 (m, 1H), 4.99 (d, J=10.9 Hz, 1H, vinyl), 5.01 (d, J=18.8 Hz, 1H, vinyl), 5.59 (ddd, J=7.5, 10.5 and 18.7 Hz, 1H, vinyl), 7.21 (d, J=8.5 Hz, 1H, H-1), 7.37 (s, 1H, H-4), 7.38 (d, J=8.5 Hz, 1H, H-2).

Preparation of Compound 84

3-cyanoketone 83 (725 mg, 2.21 mmol) was treated with 4-benzyloxybenzylmagnesium chloride as described for the preparation of compound 11. Crude product was purified by flash chromatography eluting with 5% acetone-hexanes to provide 17α-alkylated steroid 84 (610 mg, 55%) as an amorphous white solid. $^1$H NMR (400 MHz, CDCl$_3$) δ: 0.99 (s, 3H, Me), 2.61 (d, J$_{gem}$=13.4 Hz, 1H, —CH$_2$-Ph), 2.62 (m, 1H), 2.92 (m, 3H, H-6 and —CH$_2$-Ph), 3.42 (m, 1H), 4.99 (dd, J=1.5 and 10.9 Hz, 1H, vinyl), 5.01 (dd, J=1.4 and 18.8 Hz, 1H, vinyl), 5.06 (s, 2H, —O—CH$_2$-Ph), 5.66 (ddd, J=7.5, 10.5 and 18.7 Hz, 1H, vinyl), 6.95 (d, J=8.6 Hz, 2H, Ar), 7.21 (d, J=8.5 Hz, 2H, Ar), 7.23 (d, J=8.5 Hz, 1H, H-1), 7.33-7.45 (m, 7H, Ar).

Preparation of Compound 85

Debenzylation of compound 84 (300 mg, 0.596 mmol) with boron trichloride (1 M in dichloromethane, 1.78 mmol) was achieved as described for the preparation of compound 75. Crude product was purified by flash chromatography eluting with 5% acetone-hexanes to provide phenol 85 (161 mg, 65%) as an amorphous white solid. $^1$H NMR (400 MHz, CDCl$_3$) δ: 1.10 (s, 3H, Me), 2.50 (d, J$_{gem}$=13.3 Hz, 1H, —CH$_2$-Ph), 2.58 (d, J$_{gem}$=13.3 Hz, 1H, —CH$_2$-Ph), 2.76 (d, J=11.1 Hz, 1H), 2.86 (m, 2H, H-6), 3.42 (m, 1H), 4.99 (d, J=10.9 Hz, 1H, vinyl), 5.01 (d, J=18.8 Hz, 1H, vinyl), 5.66 (ddd, J=7.5, 10.5 and 18.7 Hz, 1H, vinyl), 6.69 (d, J=8.5 Hz, 2H, Ar), 7.01 (d, J=8.6 Hz, 2H, Ar), 7.21 (d, J=8.5 Hz, 1H, H-1), 7.37 (s, 1H, H-4), 7.38 (d, J=8.3 Hz, 1H, H-2).

Preparation of EM-9159

EM-9159 (107 mg, 66% for 2 steps) was obtained from phenol 85 (160 mg, 0.387 mmol) via triflate 86 as described for the preparation of compounds 66 and 83. Crude product was purified by flash chromatography eluting with 5% ethyl acetate-toluene. After evaporation of the solvent, the residual white solid was triturated from methanol. $^1$H NMR (400 MHz, CDCl$_3$) δ: 0.88 (s, 3H, Me), 2.60 (m, 1H), 2.67 (d, $J_{gem}$=13.2 Hz, 1H, —CH$_2$-Ph), 2.90 (m, 2H, H-6), 3.01 (d, $J_{gem}$=13.2 Hz, 1H, —CH$_2$-Ph), 3.42 (m, 1H), 4.98 (d, J=10.8 Hz, 1H, vinyl), 5.01 (d, J=17.6 Hz, 1H, vinyl), 5.66 (ddd, J=7.5, 10.5 and 17.8 Hz, 1H, vinyl), 7.22 (d, J=8.5 Hz, 1H, H-1), 7.37 (s, 1H, H-4), 7.38 (d, J=8.3 Hz, 1H, H-2), 7.44 (d, J=8.2 Hz, 2H, Ar), 7.60 (d, J=8.2 Hz, 2H, Ar).

Example 17

Synthesis of EM-9013

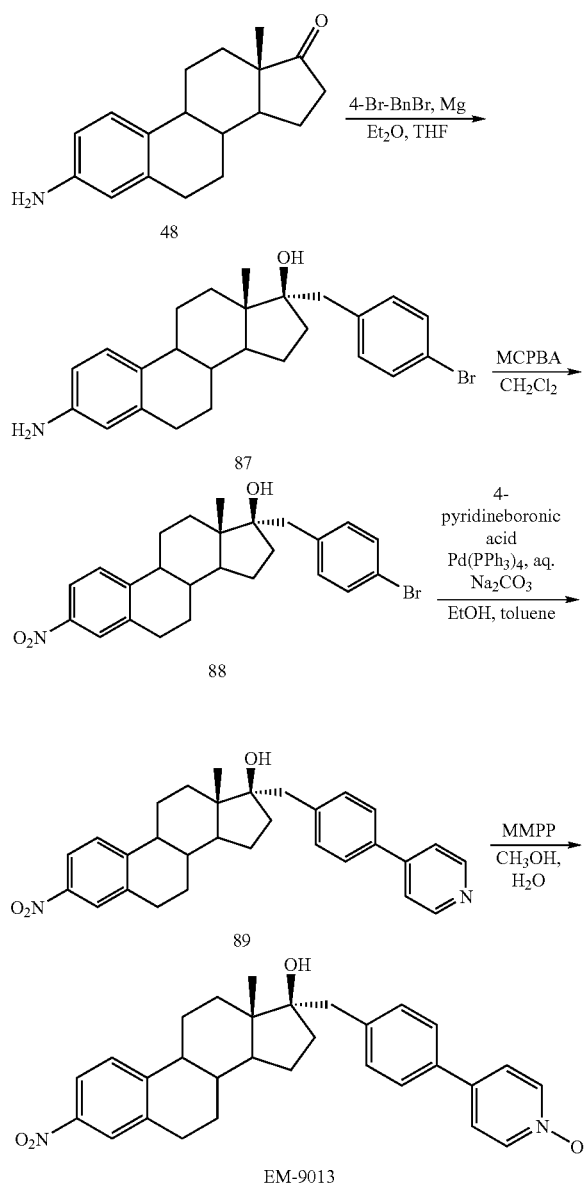

Preparation of Compound 87

After the addition of magnesium powder (432 mg, 18 mmol) in a dry 3-neck round-bottom flask equipped with a magnetic stirrer, under an argon atmosphere, the system was flame dried. After cooling, dry diethyl ether (2 mL) was added. The suspension was stirred vigorously while a 4-bromobenzyl bromide (1.5 g, 6.0 mmol) solution in diethyl ether (6 mL) was added dropwise until the temperature rose to 30° C. The temperature was kept below 30° C. with an ice bath during the rest of the addition. The mixture was stirred at room temperature for 30 min. To the freshly prepared Grignard solution (0.6 M) cooled at 0° C. was added a solution of compound 48 (170 mg, 0.63 mmol) (from Radu, I.-I., Poirier, D., Provencher, L. Tetrahedron Lett. 2002, 43, 7617) in THF (3 mL). The mixture was stirred for 2 h at room temperature. After completion of the reaction (TLC), the reaction was quenched by addition of aqueous saturated ammonium chloride. The mixture was extracted with ethyl acetate (3×). The combined organic layer was washed with aqueous saturated sodium bicarbonate and brine, dried over MgSO$_4$, filtered, and concentrated under reduced pressure. The crude compound was purified by flash chromatography (silica gel, 0-100% ethyl acetate in hexanes) to give 91 mg (35%) of compound 87. $^1$H NMR (400 MHz, CDCl$_3$) δ: 0.96 (s, 3H, Me), 2.63 (d, J=13.4 Hz, 1H, CH$_2$-Ph), 2.82 (m, 2H, H-6), 2.89 (d, J=13.3 Hz, 1H, CH$_2$-Ph), 6.47 (s, 1H, Ar), 6.54 (d, J=8.2 Hz, 1H, Ar), 7.12 (d, J=8.3 Hz, 1H, Ar), 7.20 (d, J=8.3 Hz, 2H, Ar), 7.45 (d, J=8.3 Hz, 2H, Ar).

Preparation of Compound 88

To a solution of compound 87 (91 mg, 0.21 mmol) in anhydrous dichloromethane (9 mL) was added 3-chloroperoxybenzoic acid (420 mg, 1.7 mmol). The mixture was stirred for 2 h under reflux. After completion of the reaction (TLC), the mixture was diluted with aqueous saturated sodium bicarbonate and extracted with dichloromethane (3×). The combined organic layer was washed with aqueous saturated sodium bicarbonate and brine, dried over MgSO$_4$, filtered, and concentrated under reduced pressure. The crude compound was purified by reverse-phase semi-preparative HPLC (40-100% methanol in water) to give 34 mg (35%) of compound 88. $^1$H NMR (400 MHz, CDCl$_3$) δ: 0.98 (s, 3H, Me), 2.62 (d, J=13.4 Hz, 1H, CH$_2$-Ph), 2.89 (d, J=13.1 Hz, 1H, CH$_2$-Ph), 2.99 (m, 2H, H-6), 7.19 (d, J=8.3 Hz, 2H, Ar), 7.45 (m, 3H, Ar), 7.98 (m, 2H, Ar).

Preparation of Compound 89

Compound 89 was prepared from compound 88 (34 mg, 0.072 mmol) and 4-pyridineboronic acid (16 mg, 0.13 mmol) using the procedure described for EM-8420. The crude compound was purified by reverse-phase semi-preparative HPLC (5-100% methanol in water) to give 20 mg (61%) of compound 89. $^1$H NMR (400 MHz, CDCl$_3$) δ: 1.01 (s, 3H, Me), 2.74 (d, J=13.3 Hz, 1H, CH$_2$-Ph), 2.99 (m, 3H, CH$_2$-Ph, H-6), 7.45 (m, 3H, Ar), 7.53 (bs, 2H, Pyr), 7.62 (d, J=8.1 Hz, 2H, Ar), 7.97 (m, 2H, Ar), 8.65 (bs, 2H, Pyr).

Preparation of EM-9013

To a suspension of compound 89 (20 mg, 0.043 mmol) in methanol-water/3:1 (4 mL) was added magnesium monoperoxyphthalate (50 mg, 0.080 mmol). The solution was stirred under reflux for 2 h. After completion of the reaction (TLC), the mixture was diluted with aqueous saturated sodium bicarbonate and extracted with ethyl acetate (3×). The combined organic layer was washed with aqueous saturated sodium carbonate and brine, dried over MgSO$_4$, filtered, and concentrated under reduced pressure. The crude compound was purified by reverse-phase semi-preparative HPLC (5-100% methanol in water) to give 5.0 mg (25%) of EM-9013. $^1$H NMR (400 MHz, CDCl$_3$) δ: 1.00 (s, 3H, Me), 2.73 (d, J=13.4 Hz, 1H, CH$_2$-Ph), 2.99 (m, 3H, CH$_2$-Ph, H-6), 7.45 (m, 3H, Ar), 7.54 (m, 4H, Ar, Pyr), 7.98 (m, 2H, Ar), 8.25 (d, J=7.2 Hz, 2H, Pyr).

Example 18

Synthesis of EM-3585

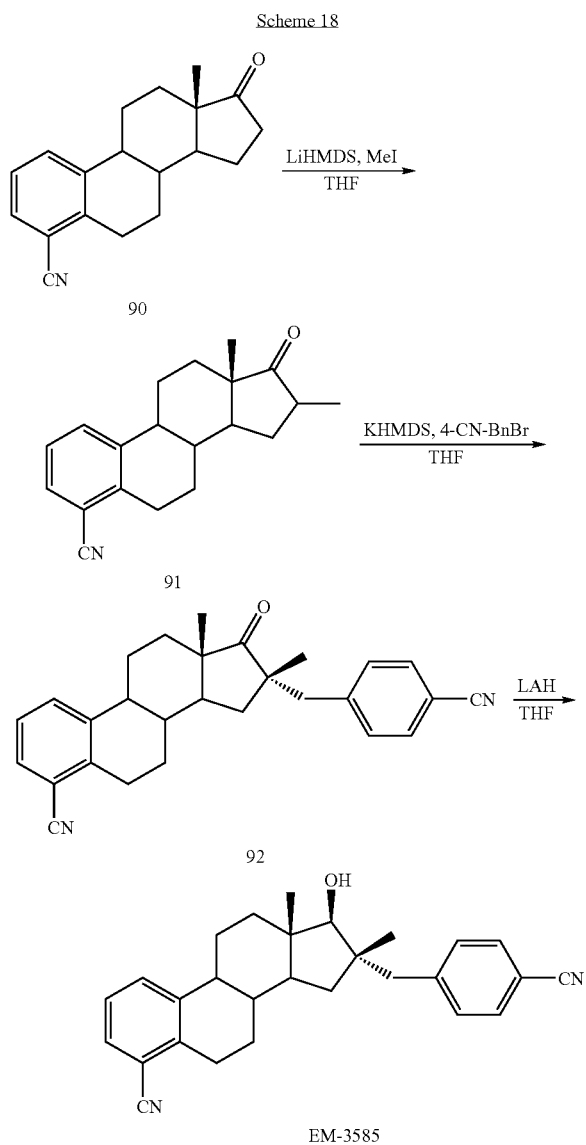

Scheme 18

Preparation of Compound 91

To a stirred solution of 90 (650 mg, 2.32 mmol) (from Labrie, F., Provencher, L., Gauthier, S. WO 2004/089971) in dry THF (25 mL) at 0° C. was dropwise added LiHMDS (1.0 M in THF, 2.45 mL, 2.45 mmol) under an argon atmosphere. The solution was stirred at room temperature for 30 min then cooled down to −78° C. for the addition of iodomethane (159 µL, 2.55 mmol). The solution was then stirred at room temperature for 2 h. The reaction was quenched with ice/water and extracted with ethyl acetate. The combined organic phase was washed with aqueous saturated ammonium chloride, aqueous sodium sulfite 1 M, water and brine, dried over $MgSO_4$, filtered, then rotary evaporated to give a crude solid. Purification by flash chromatography (hexanes-ethyl acetate/19:1 to hexanes-ethyl acetate/4:1) gave the compound 91 (910 mg, 52%) as a solid. The ratio α/β isomer is 5/1; pure α-methyl isomer: $^1$H NMR (300 MHz, $CDCl_3$) δ: 0.95 (s, 3H, Me), 1.16 (d, J=7.7 Hz, 3H, Me-16), 3.01-3.16 (m, 2H, H-6), 7.24 (m, 1H, Ar), 7.48 (d, J=7.5 Hz, 1H, Ar), 7.53 (d, J=8.0 Hz, 1H, Ar).

Preparation of Compound 92

To a stirred solution of 91 (289 mg, 0.986 mmol) in dry THF (8 mL) at 0° C. was dropwise added KHMDS (0.5 M in toluene, 2.9 mL, 1.45 mmol) under an argon atmosphere. The solution was stirred at room temperature for 30 min then cooled down to −78° C. for the addition of a solution of 4-(bromomethyl)benzonitrile (290 mg, 1.48 mmol) in THF (2 mL). The solution was then stirred at −78° C. for 30 min and allowed to rise to room temperature for 2 h. The reaction was quenched with ice/water and extracted with ethyl acetate. The combined organic phase was washed with aqueous saturated ammonium chloride, aqueous sodium sulfite 1 M, water and brine, dried over $MgSO_4$, filtered, then rotary evaporated. The crude solid was purified by flash chromatography (hexanes-ethyl acetate/19:1 to hexanes-ethyl acetate/9:1) and recrystallized in hexanes-dichloromethane/19:1. The mother liquors were chromatographed (hexanes-dichloromethane/1:1), then the solids were combined to afford compound 92 (214 mg, 53%). $^1$H NMR (300 MHz, $CDCl_3$) δ: 0.94 (s, 3H, Me), 1.28 (s, 3H, Me-16), 2.60 (d, J=12.8 Hz, 1H, $CH_2$-Ph), 2.90 (m, 1H, H-6), 3.02 (d, J=12.9 Hz, 1H, $CH_2$-Ph), 3.16 (m, 1H, H-6), 7.24 (m, 3H, Ar), 7.45 (m, 2H, Ar), 7.57 (d, J=8.1 Hz, 2H, Ar).

Preparation of EM-3585

To the ketone 92 (154 mg, 0.376 mmol) in dry THF (8 mL) was added dropwise $LiAlH_4$ (1.0 M in THF, 413 µL, 0.413 mmol) at −78° C. The solution was stirred for 1 h, then quenched with sodium sulfate decahydrate (605 mg, 1.88 mmol), and stirred overnight. The suspension was filtered and concentrated under reduced pressure. The crude product was then purified by flash chromatography (hexanes-ethyl acetate/9:1 to hexanes-ethyl acetate/4:1) to give EM-3585 (140 mg, 90%). $^1$H NMR (300 MHz, $CDCl_3$) δ: 0.82 (s, 3H, Me), 1.02 (s, 3H, Me-16), 2.68 (d, J=12.8 Hz, 1H, $CH_2$-Ph), 2.76 (d, J=12.8 Hz, 1H, $CH_2$-Ph), 2.92 (m, 1H, H-6), 3.11 (m, 1H, H-6), 3.53 (s, 1H, H-17), 7.23 (m, 1H, Ar), 7.33 (d, J=8.1 Hz, 2H, Ar), 7.49 (m, 2H, Ar), 7.60 (d, J=8.2 Hz, 2H, Ar).

PHARMACEUTICAL COMPOSITION EXAMPLES

Set forth below, by way of example and not of limitation, are several pharmaceutical compositions utilizing a preferred active antiandrogen EM-5985 for systemic use. Other antiandrogens or SARMs of the invention or combination thereof, may be used in place of (or in addition to) EM-5985. The concentration of active ingredient may be varied over a wide range as discussed herein. The amounts and types of other ingredients that may be included are well known in the art.

Example A

| Composition suitable for injection | |
|---|---|
| Ingredient | Weight % (by weight of total composition) |
| EM-5985 | 5.0 |
| Ethanol | 6.4 |
| NaCl | 0.8 |
| Water | 86.9 |
| Benzyl alcohol | 0.9 |

Example B

| Tablet | |
|---|---|
| Ingredient | Weight % (by weight of total composition) |
| EM-5985 | 20.0 |
| Gelatin | 5.0 |
| Lactose | 47.5 |
| Starch | 27.5 |

Example C

| Gelatin capsule | |
|---|---|
| Ingredient | Weight % (by weight of total composition) |
| EM-5985 | 20.0 |
| Lactose hydrous | 62.0 |
| Starch | 4.8 |
| Cellulose microcrystalline | 12.8 |
| Magnesium stearate | 0.4 |

Other antiandrogens (i.e. EM-5854, EM-8505 or EM-8454) or SARMs (i.e. EM-8420 or EM-9017) may be substituted for EM-5985 in the above formulations. For combination therapies, 5alpha reductase inhibitors, 17beta-hydroxysteroid dehydrogenase type 5 inhibitors and 17b-hydroxysteroid dehydrogenase inhibitors type 13 could be added at weight % (with prorata reduction of other components).

Example D

| Composition suitable for injection | |
|---|---|
| Ingredient | Weight % (by weight of total composition) |
| EM-5985 | 5.0 |
| Finasteride | 0.4 |
| Ethanol | 6.0 |
| NaCl | 0.8 |
| Water | 86.9 |
| Benzyl alcohol | 0.9 |

Example E

| Tablet | |
|---|---|
| Ingredient | Weight % (by weight of total composition) |
| EM-5985 | 20.0 |
| Finasteride | 1.0 |
| Gelatin | 5.0 |
| Lactose | 46.5 |
| Starch | 27.5 |

Example F

| Gelatin capsule | |
|---|---|
| Ingredient | Weight % (by weight of total composition) |
| EM-5985 | 20.0 |
| Finasteride | 1.0 |
| Lactose hydrous | 61.0 |
| Starch | 4.8 |
| Cellulose microcystalline | 12.8 |
| Magnesium stearate | 0.4 |

Example G

| Composition suitable for injection | |
|---|---|
| Ingredient | Weight % (by weight of total composition) |
| EM-5985 | 5.0 |
| EM-1404 | 5.0 |
| Ethanol | 6.0 |
| NaCl | 0.8 |
| Water | 82.3 |
| Benzyl alcohol | 0.9 |

Example H

| Tablet | |
|---|---|
| Ingredient | Weight % (by weight of total composition) |
| EM-5985 | 20.0 |
| EM-1404 | 20.0 |
| Gelatin | 5.0 |
| Lactose | 27.5 |
| Starch | 27.5 |

Example I

| Gelatin capsule | |
|---|---|
| Ingredient | Weight % (by weight of total composition) |
| EM-5985 | 20.0 |
| EM-1404 | 20.0 |
| Lactose hydrous | 42.0 |
| Starch | 4.8 |
| Cellulose microcrystalline | 12.8 |
| Magnesium stearate | 0.4 |

Example J

| Composition suitable for injection | |
|---|---|
| Ingredient | Weight % (by weight of total composition) |
| EM-5985 | 5.0 |
| EM-1791 | 0.4 |
| Ethanol | 6.0 |
| NaCl | 0.8 |
| Water | 86.9 |
| Benzyl alcohol | 0.9 |

Example K

| Tablet | |
|---|---|
| Ingredient | Weight % (by weight of total composition) |
| EM-5985 | 20.0 |
| EM-1791 | 20.0 |
| Starch | 27.5 |
| Gelatin | 5.0 |
| Lactose | 27.5 |

Example L

| Gelatin capsule | |
|---|---|
| Ingredient | Weight % (by weight of total composition) |
| EM-5985 | 20.0 |
| EM-1791 | 20.0 |
| Lactose hydrous | 42.0 |
| Cellulose microcrystalline | 12.8 |
| Magnesium stearate | 0.4 |
| Starch | 4.8 |

The invention has been described in terms of preferred embodiments and examples, but is not limited thereby. Those of skill in the art will readily recognize the broader applicability and scope of the invention which is limited only by the patent claims that issue from this application or any patent application claiming priority (directly or indirectly) hereto.

What is claimed is:

1. A compound, a salt or an N-oxide thereof, having the following molecular formula:

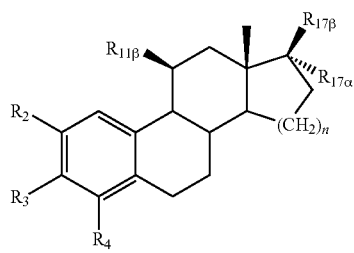

wherein n is an integer from 1 to 2;

wherein $R_2$ is selected from the group consisting of hydrogen and fluoro;

wherein $R_3$ is selected from the group consisting of hydrogen, cyano, chloro, methoxy, ethoxy, nitro, and propynyl;

wherein $R_4$ is selected from the group consisting of hydrogen, fluoro, chloro, bromo, cyano, amino, cyclopropyl, and $C_1$ alkyl;

wherein said cyclopropyl and $C_1$ alkyl in $R_4$ are optionally substituted with fluoro;

wherein $R_{11\beta}$, is selected from the group consisting of hydrogen, fluoro, $C_1$-$C_2$ alkyl, and $C_2$ alkenyl;

wherein $R_{17\alpha}$ and $R_{17\beta}$ are independently selected from the group consisting of hydroxyl, methoxy and -A-A'-Ar A and A' being spacer groups independently selected from the group consisting of absent —$CH_2$—, —CHF—, —CH($CH_3$)—, propynylene, and

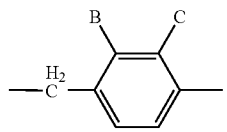

(B and C being independently selected from the group consisting of hydrogen, fluoro, and methyl), and Ar being selected from the group consisting of:

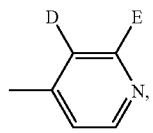

(D being selected from the group consisting of hydrogen, fluoro, chloro, bromo, methyl, ethyl and methoxy and E being selected from the group consisting of hydrogen, cyano and methyl);

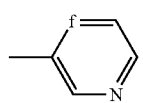

(f is CH or nitrogen);
and

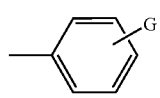

(G being selected from the group consisting of cyano, —$CONR^1R^2$ ($R^1$ and $R^2$ are independently selected from the group consisting of hydrogen and methyl) and —$SOCH_3$ wherein when $R_{17\alpha}$ is hydroxyl or methoxy, $R_{17\beta}$ is -A-A'-Ar, and when $R_{17\beta}$ is hydroxyl or methoxy, $R_{17\alpha}$ is -A-A'-Ar.

2. The compound, a salt or an N-oxide thereof, of claim 1, having the following molecular formula:

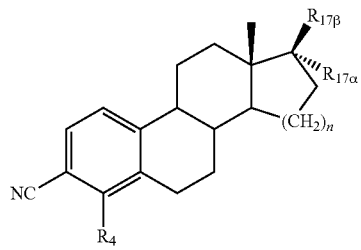

wherein n is an integer from 1 to 2;

wherein $R_4$ is selected from the group consisting of fluoro, chloro, and methyl;

wherein $R_{17\alpha}$ and $R_{17\beta}$ are independently selected from the group consisting of hydroxyl and —CH$_2$—Ar Ar being selected from the group consisting of:

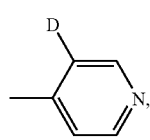

(D being selected from the group consisting of hydrogen, fluoro, and methyl);

wherein when $R_{17\alpha}$ is hydroxyl or methoxy, $R_{17\beta}$ is —CH$_2$—Ar, and when $R_{17\beta}$ is hydroxyl or methoxy, $R_{17\alpha}$ is —CH$_2$—Ar.

3. An antiandrogenic compound having a molecular formula selected from the group consisting of:

EM-5854

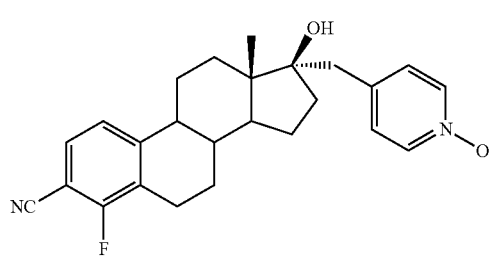

EM-5985

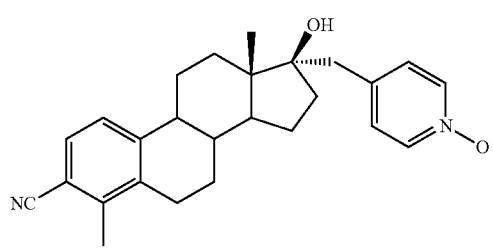

EM-8454

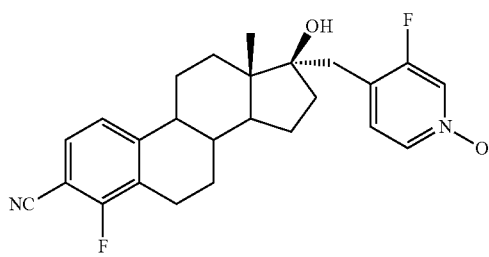

EM-8505

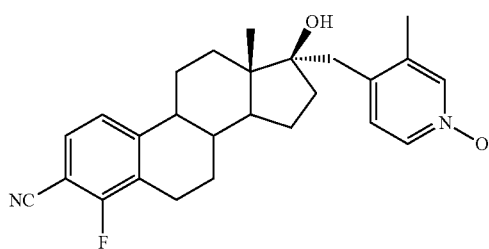

EM-5945

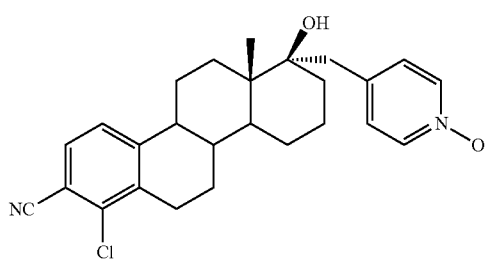

EM-9140

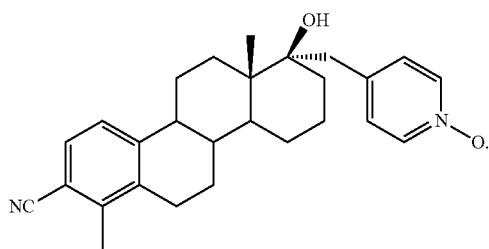

4. A Selective Androgen Receptor Modulator having a molecular formula selected from the group consisting of:

EM-8419

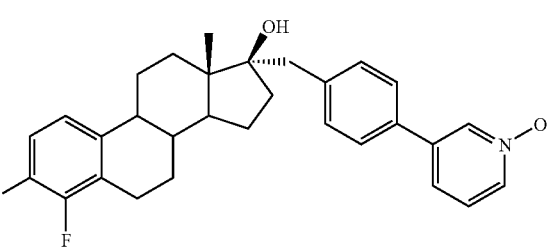

EM-8420

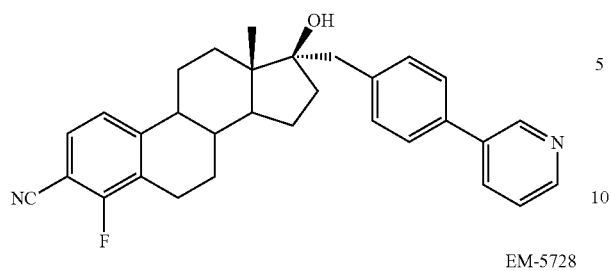

EM-5728

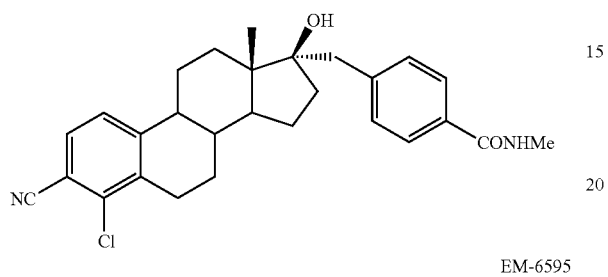

EM-6595

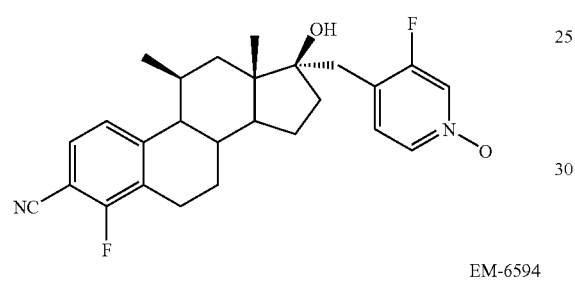

EM-6594

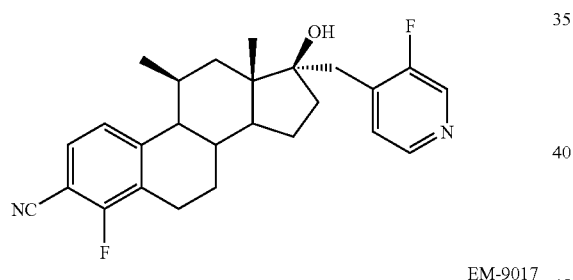

EM-9017

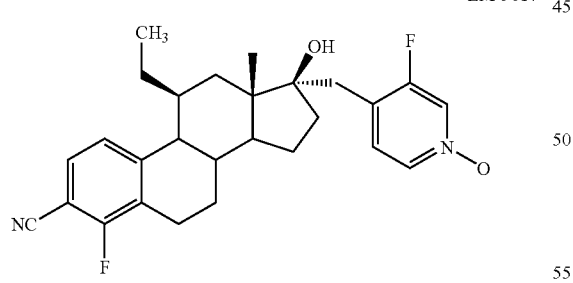

EM-9016

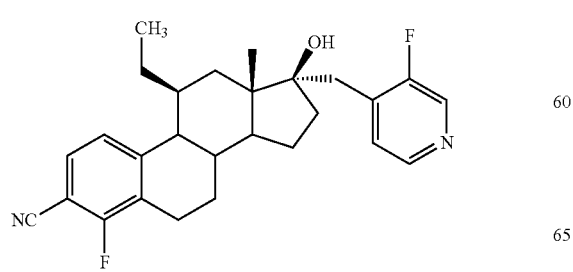

EM-6583

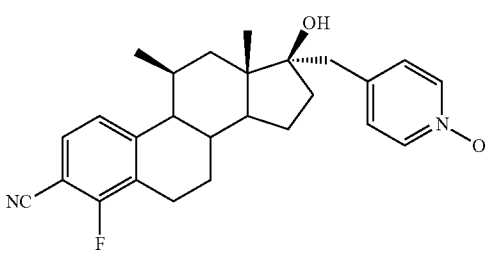

EM-6582

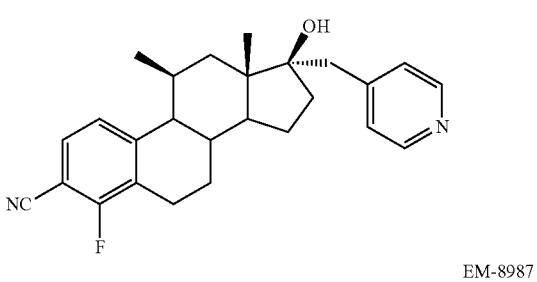

EM-8987

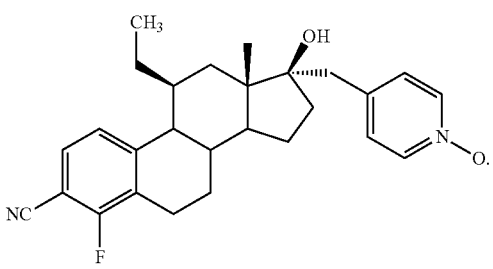

5. A pharmaceutical composition comprising a pharmaceutically acceptable diluent or carrier and a therapeutically effective amount of at least one compound, or a salt or an N-oxide thereof, having the following molecular formula:

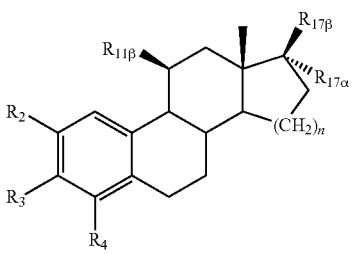

wherein n is an integer from 1 to 2;

wherein $R_2$ is selected from the group consisting of hydrogen and fluoro;

wherein $R_3$ is selected from the group consisting of hydrogen, cyano, chloro, methoxy, ethoxy, nitro, and propynyl;

wherein $R_4$ is selected from the group consisting of hydrogen, fluoro, chloro, bromo, cyano, amino, cyclopropyl, and $C_1$ alkyl, wherein said cyclopropyl and $C_1$ alkyl are optionally-substituted with fluoro;

wherein $R_{11\beta}$, is selected from the group consisting of hydrogen, fluoro, $C_1$-$C_2$ alkyl, and $C_2$ alkenyl;

wherein $R_{17\alpha}$ and $R_{17\beta}$ are independently selected from the group consisting of hydroxyl, methoxy and -A-A'-Ar A and A' being spacer groups independently selected from the group consisting of absent —CH$_2$—, —CHF—, —CH(CH$_3$)—, propynylene, and

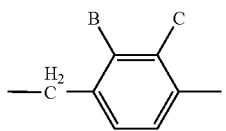

(B and C being independently selected from the group consisting of hydrogen, fluoro, and methyl), and Ar being selected from the group consisting of:

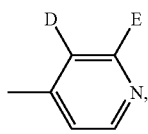

(D being selected from the group consisting of hydrogen, fluoro, chloro, bromo, methyl, ethyl and methoxy and E being selected from the group consisting of hydrogen, cyano and methyl);

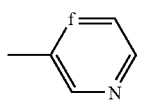

(f is CH or nitrogen); and

(G being selected from the group consisting of cyano, —CONR$^1$R$^2$ (R$^1$ and R$^2$ are independently selected from the group consisting of hydrogen and methyl) and —SOCH$_3$
wherein when R$_{17\alpha}$ is hydroxyl or methoxy, R$_{17\beta}$ is -A-A'-Ar, and when R$_{17\beta}$ is hydroxyl or methoxy, R$_{17\alpha}$ is -A-A'-Ar.

6. The pharmaceutical composition of claim 5 wherein the compound, a salt or an N-oxide thereof, has the following molecular formula:

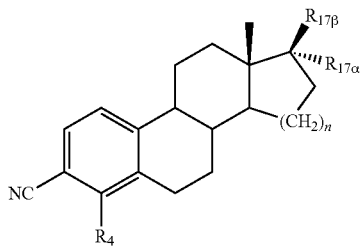

wherein n is an integer from 1 to 2;
wherein R$_4$ is selected from the group consisting of fluoro, chloro, and methyl;

wherein R$_{17\alpha}$ and R$_{17\beta}$ are independently selected from the group consisting of hydroxyl and —CH$_2$—Ar
Ar being selected from the group consisting of:

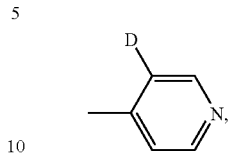

(D being selected from the group consisting of hydrogen, fluoro, and methyl);
wherein when R$_{17\alpha}$ is hydroxyl or methoxy, R$_{17\beta}$ is —CH$_2$—Ar, and when R$_{17\beta}$ is hydroxyl or methoxy, R$_{17\alpha}$ is —CH$_2$—Ar.

7. A pharmaceutical composition comprising a pharmaceutically acceptable diluent or carrier and a therapeutically effective amount of at least one antiandrogenic compound having a molecular formula selected from the group consisting of:

EM-5854

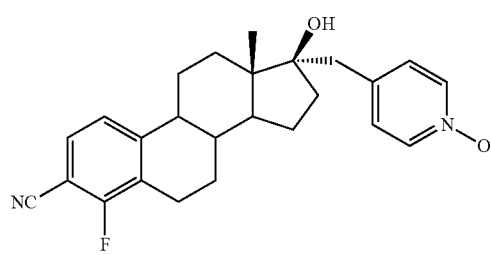

EM-5985

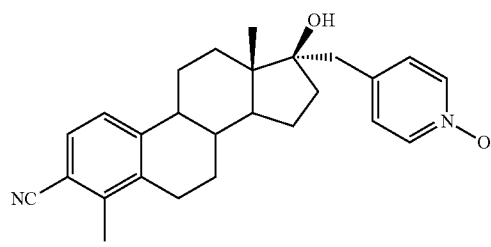

EM-8454

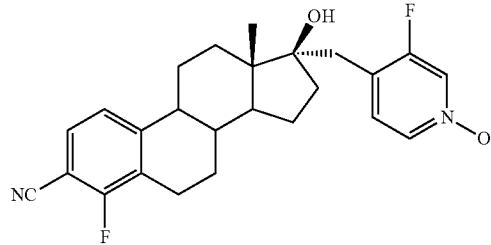

EM-8505

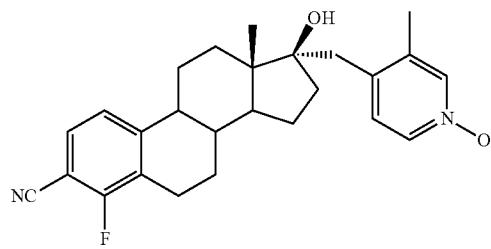

EM-5945
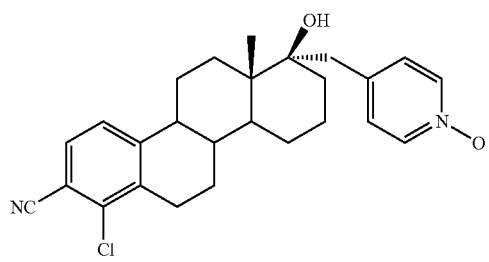
EM-9140
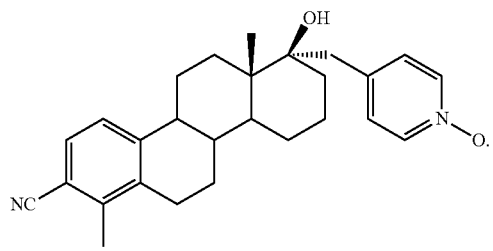
8. A pharmaceutical composition comprising a pharmaceutically acceptable diluent or carrier and a therapeutically effective amount of at least one Selective Androgen Receptor Modulator having a molecular formula selected from the group consisting of:
EM-8419
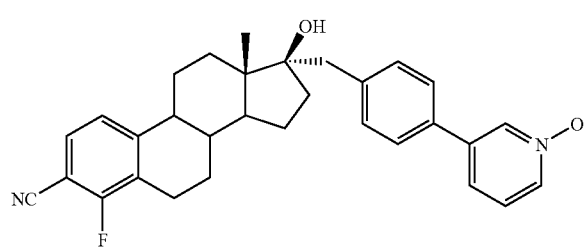
EM-8420
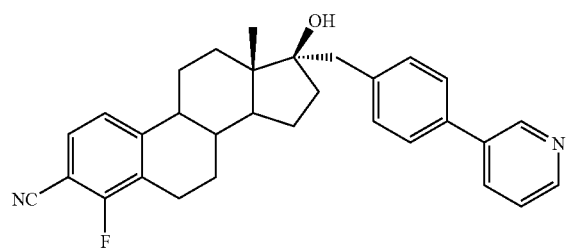
EM-5728
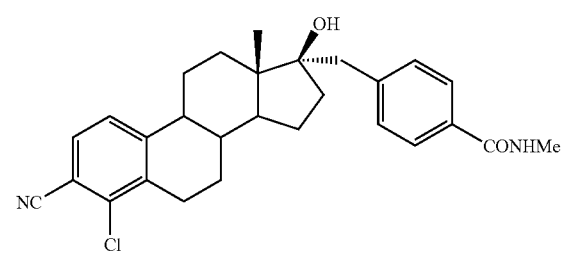
EM-6595
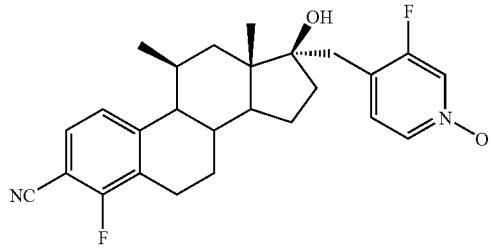
EM-6594
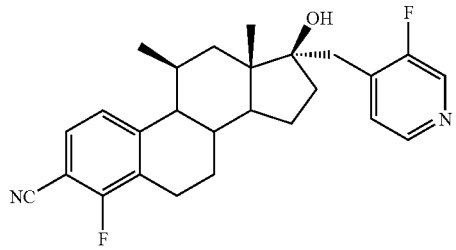
EM-9017
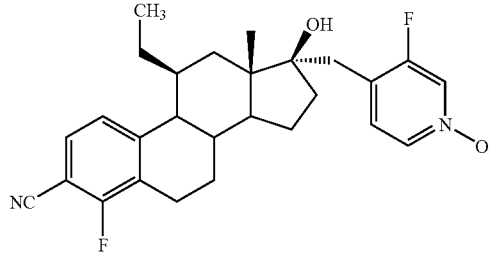
EM-9016
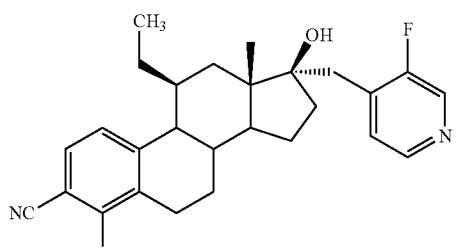
EM-6583
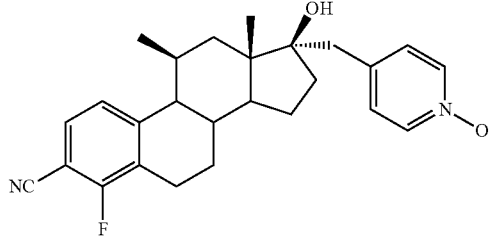
EM-6582
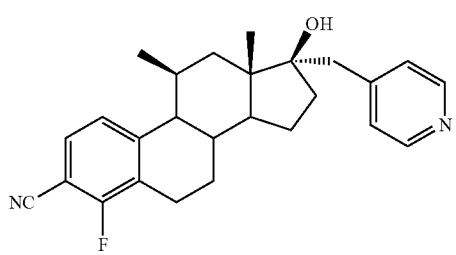

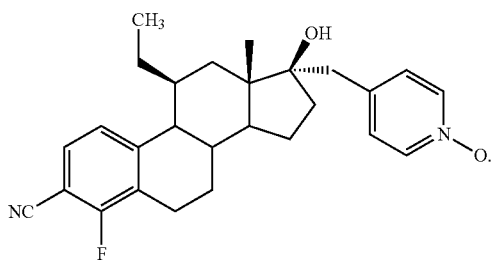

EM-8987

9. A method of treating prostate cancer, comprising administering to a patient in need of such treatment a therapeutically effective amount of the compound or pharmaceutical composition of any one of claims 1 and 5.

10. The method of claim 9 further comprising orchiectomy or administering an LHRH agonist or antagonist.

11. A method of treating benign prostatic hyperplasia comprising administering to a patient in need of such treatment, a therapeutically effective amount of the compound or pharmaceutical composition of any one of claims 1 and 5.

12. A method of treating polycystic ovarian syndrome comprising administering to a patient in need of such treatment a therapeutically effective amount of the compound or pharmaceutical composition of any one of claims 1 and 5.

13. A method of treating acne, seborrhea, hirsutism or androgenic alopecia comprising administering to a patient in need of such treatment a therapeutically effective amount of the compound or pharmaceutical composition of any one of claims 1 and 5.

14. A method of treating precocious puberty comprising administering to a male or female patient in need of such treatment a therapeutically effective amount of the compound or pharmaceutical composition of any one of claims 1 and 5.

15. The method of claim 14 comprising administering to a male patient a therapeutically effective amount of an LHRH agonist or antagonist.

16. The compound of claim 1 possessing a tissue-specific antiandrogenic activity and a tissue-specific androgenic activity.

17. The pharmaceutical composition of claim 5 wherein the active compound possesses a tissue-specific antiandrogenic activity and a tissue-specific androgenic activity.

18. A method of treating diseases related to loss of androgenic stimulation, selected from muscle atrophy and weakness, skin atrophy, bone loss, anemia, arteriosclerosis, cardiovascular disease, loss of energy, type 2 diabetes and abdominal fat accumulation comprising administering to a patient in need of such treatment a therapeutically effective amount of the compound or pharmaceutical composition of any one either of claim 1 or 5.

* * * * *